(12) United States Patent
DeKelver et al.

(10) Patent No.: US 11,401,512 B2
(45) Date of Patent: Aug. 2, 2022

(54) ENGINEERED TARGET SPECIFIC NUCLEASES

(71) Applicant: Sangamo Therapeutics, Inc., Richmond, CA (US)

(72) Inventors: Russell DeKelver, Richmond, CA (US); Ivan Krivega, Richmond, CA (US); Jeffrey C. Miller, Richmond, CA (US); Lei Zhang, Richmond, CA (US)

(73) Assignee: Sangamo Therapeutics, Inc., Brisbane, CA (US)

( * ) Notice: Subject to any disclaimer, the term of this patent is extended or adjusted under 35 U.S.C. 154(b) by 495 days.

(21) Appl. No.: 16/271,250

(22) Filed: Feb. 8, 2019

(65) Prior Publication Data

US 2019/0241877 A1 Aug. 8, 2019

Related U.S. Application Data

(60) Provisional application No. 62/628,016, filed on Feb. 8, 2018, provisional application No. 62/728,226, filed on Sep. 7, 2018, provisional application No. 62/758,786, filed on Nov. 12, 2018, provisional application No. 62/795,937, filed on Jan. 23, 2019, provisional application No. 62/802,092, filed on Feb. 6, 2019.

(51) Int. Cl.
| | |
|---|---|
| *C12N 9/22* | (2006.01) |
| *C12N 7/00* | (2006.01) |
| *A61K 38/46* | (2006.01) |
| *A61K 48/00* | (2006.01) |
| *C12N 9/64* | (2006.01) |
| *C12N 9/16* | (2006.01) |
| *C12N 9/24* | (2006.01) |
| *A61K 38/47* | (2006.01) |
| *A61K 38/48* | (2006.01) |

(52) U.S. Cl.
CPC .............. *C12N 9/22* (2013.01); *A61K 38/465* (2013.01); *A61K 38/47* (2013.01); *A61K 38/4846* (2013.01); *A61K 48/0066* (2013.01); *C12N 7/00* (2013.01); *C12N 9/16* (2013.01); *C12N 9/2402* (2013.01); *C12N 9/644* (2013.01); *C12Y 301/06013* (2013.01); *C12Y 302/01076* (2013.01); *C12Y 304/21022* (2013.01); *C12N 2750/14343* (2013.01); *C12N 2800/80* (2013.01)

(58) Field of Classification Search
CPC .............................. C12N 9/22; C07K 2319/81
See application file for complete search history.

(56) References Cited

U.S. PATENT DOCUMENTS

| | | |
|---|---|---|
| 5,356,802 A | 10/1994 | Chandrasegaran |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,794,136 B1 | 9/2004 | Eisenberg et al. |
| 6,824,978 B1 | 11/2004 | Cox, III et al. |
| 6,903,185 B2 | 6/2005 | Kim et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,153,949 B2 | 12/2006 | Kim et al. |
| 7,163,824 B2 | 1/2007 | Cox, III et al. |
| 7,253,273 B2 | 8/2007 | Collingwood |
| 7,262,054 B2 | 8/2007 | Jamieson et al. |
| 7,361,635 B2 | 4/2008 | Miller et al. |
| 7,419,829 B2 | 9/2008 | Mitrophanous et al. |
| 7,888,121 B2 | 2/2011 | Urnov et al. |
| 7,914,796 B2 | 3/2011 | Miller et al. |

(Continued)

FOREIGN PATENT DOCUMENTS

| | | |
|---|---|---|
| GB | 2338237 A | 12/1999 |
| WO | WO 95/19431 A1 | 7/1995 |

(Continued)

OTHER PUBLICATIONS

Alves, et al., "Characterization of the Nuclear Localization Signal of the Hepatitis Delta Virus Antigen," *Virology* 370(1):12-21 (2008).
Araujo, et al., "Before It Gets Started: Regulating Translation at the 5' UTR," *Comp and Funct Genom* doi:10.1155/2012/475731 (2012).
Beerli, et al., "Engineering Polydactyl Zinc-Finger Transcription Factors," *Nature Biotechnology* 20:135-141 (2002).
Bejerano, et al., "Ultraconserved Elements in the Human Genome," *Science* 302(5675): 1321-1325 (2004).
Bitinaite, et al., "Foki Dimerization is Required for DNA Cleavage," *Proc. Natl. Acad Sci USA* 95:10,570-10,575 (1998).

(Continued)

*Primary Examiner* — Karen Cochrane Carlson
(74) *Attorney, Agent, or Firm* — Foley & Lardner LLP

(57) ABSTRACT

Described herein are engineered nucleases comprising mutations in the cleavage domain (e.g., FokI or homologue thereof) and/or DNA binding domain (zinc finger protein, TALE, single guide RNA) such that on-target specificity is increased.

33 Claims, 27 Drawing Sheets

Specification includes a Sequence Listing.

(56) References Cited

U.S. PATENT DOCUMENTS

| | | | |
|---|---|---|---|
| 7,951,925 B2 | 5/2011 | Ando et al. | |
| 7,972,854 B2 | 7/2011 | Miller et al. | |
| 8,034,598 B2 | 10/2011 | Miller | |
| 8,110,379 B2 | 2/2012 | DeKelver et al. | |
| 8,409,861 B2 | 4/2013 | Guschin et al. | |
| 8,563,314 B2 | 10/2013 | Gregory et al. | |
| 8,586,526 B2 | 11/2013 | Gregory et al. | |
| 8,597,912 B2 | 12/2013 | Collingwood et al. | |
| 8,623,618 B2 * | 1/2014 | Doyon | C07K 7/06 435/91.53 |
| 8,703,489 B2 | 4/2014 | Wang | |
| 8,771,985 B2 | 7/2014 | Cui et al. | |
| 8,772,453 B2 | 7/2014 | Paschon et al. | |
| 8,945,868 B2 | 2/2015 | Collingwood et al. | |
| 8,956,828 B2 | 2/2015 | Bonini et al. | |
| 8,962,281 B2 | 2/2015 | Doyon et al. | |
| 9,005,973 B2 | 4/2015 | Cost et al. | |
| 9,045,763 B2 | 6/2015 | DeKelver et al. | |
| 9,200,266 B2 | 12/2015 | Wang | |
| 9,234,187 B2 | 1/2016 | Rebar et al. | |
| 9,255,250 B2 | 2/2016 | Gregory et al. | |
| 9,394,545 B2 | 7/2016 | Rebar | |
| 9,458,205 B2 | 10/2016 | Gregory et al. | |
| 9,567,609 B2 | 2/2017 | Paschon et al. | |
| 9,877,988 B2 | 1/2018 | Rebar | |
| 9,956,247 B2 | 5/2018 | Rebar | |
| 10,081,661 B2 * | 9/2018 | Miller | A61P 7/04 |
| 2003/0232410 A1 | 12/2003 | Liljedahl et al. | |
| 2005/0026157 A1 | 2/2005 | Baltimore et al. | |
| 2005/0064474 A1 | 3/2005 | Urnov et al. | |
| 2005/0208489 A1 | 9/2005 | Carroll et al. | |
| 2005/0267061 A1 | 12/2005 | Martin | |
| 2006/0063231 A1 | 3/2006 | Li et al. | |
| 2006/0188987 A1 | 8/2006 | Guschin et al. | |
| 2007/0218528 A1 | 9/2007 | Miller | |
| 2008/0131962 A1 | 6/2008 | Miller | |
| 2008/0159996 A1 | 7/2008 | Ando et al. | |
| 2009/0305346 A1 | 12/2009 | Miller | |
| 2010/0218264 A1 | 8/2010 | Cui et al. | |
| 2011/0201055 A1 | 8/2011 | Doyon et al. | |
| 2011/0265198 A1 | 10/2011 | Gregory et al. | |
| 2012/0017290 A1 | 1/2012 | Cui et al. | |
| 2012/0040398 A1 | 2/2012 | Miller | |
| 2012/0060230 A1 | 3/2012 | Collingwood et al. | |
| 2013/0122591 A1 | 5/2013 | Cost et al. | |
| 2013/0137104 A1 | 5/2013 | Cost et al. | |
| 2013/0177960 A1 | 7/2013 | Rebar | |
| 2013/0177983 A1 | 7/2013 | Rebar | |
| 2015/0056705 A1 | 2/2015 | Conway et al. | |
| 2015/0159172 A1 * | 6/2015 | Miller | C07K 14/47 514/44 R |
| 2015/0166615 A1 | 6/2015 | Xia et al. | |
| 2016/0326548 A1 | 11/2016 | Cost | |
| 2017/0119906 A1 | 5/2017 | Riley et al. | |
| 2018/0087072 A1 | 3/2018 | Miller et al. | |
| 2018/0185516 A1 | 7/2018 | Ansell et al. | |

FOREIGN PATENT DOCUMENTS

| | | | |
|---|---|---|---|
| WO | WO 96/06166 A1 | 2/1996 | |
| WO | WO 98/37186 A1 | 8/1998 | |
| WO | WO 98/53057 A1 | 11/1998 | |
| WO | WO 98/53058 A1 | 11/1998 | |
| WO | WO 98/53059 A1 | 11/1998 | |
| WO | WO 98/53060 A1 | 11/1998 | |
| WO | WO 98/54311 A1 | 12/1998 | |
| WO | WO 00/27878 A1 | 5/2000 | |
| WO | WO 01/27293 A1 | 4/2001 | |
| WO | WO 01/60970 A2 | 8/2001 | |
| WO | WO 01/88197 A2 | 11/2001 | |
| WO | WO 02/016536 A1 | 2/2002 | |
| WO | WO-02/44376 A2 | 6/2002 | |
| WO | WO 02/099084 A2 | 12/2002 | |
| WO | WO 03/016496 A2 | 2/2003 | |
| WO | WO 2007/014275 A2 | 2/2007 | |
| WO | WO-2010/079430 A1 | 7/2010 | |
| WO | WO-2014036219 A2 * | 3/2014 | C12N 9/22 |
| WO | WO 2014/097113 A2 | 6/2014 | |
| WO | WO 2017/106537 A2 | 6/2017 | |
| WO | WO 2017/123757 | 7/2017 | |
| WO | WO 2018/039440 A1 | 3/2018 | |
| WO | WO-2020/033525 | 2/2020 | |

OTHER PUBLICATIONS

Burrow, et al., "Review of the Use of Idursulfase in the Treatment of Mucopolysaccharidosis II," *Biologics*. 2(2):311-320 (2008).

Burton, et al., "Diagnosing Hunter Syndrome in Pediatric Practice: Practical Considerations and Common Pitfalls," *Eur J Pediatr*. 171(4):631-639 (2012).

Choi, et al., "Optimization of AAV Expression Cassettes To Improve Packaging Capacity and Transgene Expression in Neurons," *Mol Brain* 7:17 (2014).

Choo, et al., "Advances in Zinc Finger Engineering," *Current Opinion in Structural Biology* 10:411-416 (2000).

Dang, et al., "Identification of the Human C-MYC Protein Nuclear Translocation Signal," *Mol Cell Biol* 8(10):4048-4054 (1988).

Dingwall, et al., "The Nucleoplasmin Nuclear Location Sequence is Larger and More Complex Than That of SV-40 Large T Antigen," *J Cell Biol* 107(3):841-849 (1988).

Donello, et al., "Woodchuck Hepatitis Virus Contains a Tripartite Posttranscriptional Regulatory Element," *J Virol* 72(6):5085-5092 (1998).

Elrod-Erickson, et al., "High-Resolution Structures of Variant ZIF268-DNA Complexes: Implications for Understanding Zinc Finger-DNA Recognition," *Structure* 6(4): 451-464 (1998).

Falcone, et al., "Both The 5' Untranslated Region and the Sequences Surrounding the Start Site Contribute To Efficient Initiation of Translation In Vitro," *Molecular and Cellular Biology* 11(5): 2656-2664 (1991).

Flajolet, et al., "Woodchuck Hepatitis Virus Enhancer I and Enhancer II Are Both Involved in N-MYC2 Activation in Woodchuck Liver Tumors," *J Virol* 72(7):6175-6180 (1998).

Galibert, et al., "Nucleotide Sequence of a Cloned Woodchuck Hepatitis Virus Genome: Comparison With the Hepatitis B Virus Sequence," *J Virol* 41(1): 51-65 (1982).

Guillinger, et al., "Fusion of Catalytically Inactive CAS9 To FokI Nuclease Improves the Specificity of Genome Modification," *Nature Biotech*. 32(6):577-582 (2014).

Guo, et al., "Directed Evolution of an Enhanced and Highly Efficient FokI Cleavage Domain for Zinc Finger Nucleases," *J. Mol. Biol*. 400(1):96-107 doi.10.1016/j.jmb.2010.04.060 (2010).

Höhne, et al., "Malignant Transformation of Immortalized Transgenic Hepatocytes After Transfection With Hepatitis B Virus DNA," *EMBO J* 9(4):1137-1145 (1990).

Isalan, et al., "A Rapid, Generally Applicable Method To Engineer Zinc Fingers Illustrated By Targeting the HIV-1 Promoter," *Nat Biotechnol*. 19(7):656-660 (2001).

Kalderon, et al., "Sequence Requirements for Nuclear Location of Simian Virus 40 Large-T Antigen," *Nature* 311(5981):33-38 (1984).

Kim, et al., "Hybrid Restriction Enzymes: Zinc Finger Fusions To Fok I Cleavage Domain," *Proc Nat'l Acad Sci USA* 93(3):1156-1160 (1996).

Kim, et al., "Insertion and Deletion Mutants Of FokI Restriction Endonuclease," *Journal of Biological Chemistry* 269(50):31978-31982 (1994).

Kim, et al., "Highly Efficient RNA-Guided Genome Editing in Human Cells Via Delivery of Purified CAS9 Ribonucleoproteins" *Genome Research* 24(6): 1012-1019 (2014).

Krieg, et al., "Functional Messenger RNAs Are Produced By SP6 In Vitro Transcription of Cloned CDNAs," *Nuc Acid Res* 12(18):7057-7070 (1984).

Laoharawee, et al., "Dose-Dependent Prevention of Metabolic and Neurologi Cisease in Murine MPS II By ZFN-Mediated In Vivo Genome Editing," *Molecular Therapy* 26(4): 1127-1136 (2018).

(56) References Cited

OTHER PUBLICATIONS

Li, et al., "Alteration of the Cleavage Distance Of Fok I Restriction Endonuclease By Insertion Mutagenesis," *Proc. Natl. Acad. Sci. U.S.A.* 90:2764-2768 (1993).
Li, et al., "Functional Domains In Fok I Restriction Endonuclease," *Proc. Natl. Acad. Sci. U.S.A.* 89:4275-4279 (1992).
Loeb, et al., "Enhanced Expression of Transgenes From Adeno-Associated Virus Vectors With the Woodchuck Hepatitis Virus Posttranscriptional Regulatory Element: Implications for Gene Therapy," *Hum Gene Ther* 10(14):2295-2305 (1999).
McCaffery, et al., "CRISPR-CAS9 D10A Nickase Target-Specific Fluorescent Labeling of Double Strand DNA for Whole Genome Mapping and Structural Variation Analysis," *Nucleic Acids Res.* 44(2):e11.doi:10.1093/nar/gkv878. (2016).
Mignone, et al., "Untranslated Regions of MRNAs," *Genome Biol* 3(3): PMCID: PMC139023 (2002).
Miller, et al., "An Improved Zinc-Finger Nuclease Architecture for Highly Specific Genome Editing," *Nat Biotechnology* 25:778-785 (2007).
Muenzer, et al., "Mucopolysaccharidosis I: Management and Treatment Guidelines," *Pediatrics* 123(1):19-29 (2009).
Okuyama, et al., "Liver-Directed Gene Therapy: A Retroviral Vector With a Complete LTR and the Apoe Enhancer-Alpha 1-Antitrypsin Promoter Dramatically Increases Expression of Human Alpha 1-Antitrypsin In Vivo," *Hum Gen Ther* 7(5):637-645 (1996).
Pabo, et al., "Design and Selection of Novel CYS2-HIS2 Zinc Finger Proteins," *Ann. Rev. Biochem.* 70:313-340 (2001).
Perez, et al., "Establishment of HIV-1 Resistance in CD4+ T Cells By Genome Editing Using Zinc-Finger Nucleases," *Nature Biotechnology* 26(7):808-816 (2008).
Ran, et al., "In Vivo Genome Editing Using *Staphylococcus aureus* CAS9," *Nature* 520:186 (2015).
Richardson, et al., "Nuclear Location Signals in Polyoma Virus Large-T," *Cell* 44(1):77-85 (1986).
Roberts, et al., "Rebase: Restriction Enzymes and Methyltransferases" *Nucleic Acids Res.* 31(1):418-420 (2003).
Schwesinger, et al., "Intrachoroidal Neovascularization in Transgenic Mice Overexpressing Vascular Endothelial Growth Factor in the Retinal Pigment Epithelium," *American Journal of Pathology* 158(3):1161-1172 (2001).
Segal, et al., "Custom DNA-Binding Proteins Come of Age: Polydactyl Zinc-Finger Proteins," *Current Opinion Biotechnology* 12:632-637 (2001).
Shachter, et al., "Localization of a Liver-Specific Enhancer in the Apolipoprotein E/C-I/C-II Gene Locus," *J Lipid Res* 34(10): 1699-1707 (1993).
Sharma, et al., "In Vivo Genome Editing of the Albumin Locus as a Platform for Protein Replacement Therapy," *Blood* 126(15): 1777-1784 (2015).
Siomi, et al., "A Nuclear Localization Domain in the HNRNP A1 Protein," *J Cell Biol* 129(3):551-560 (1995).
Siomi, et al., "Sequence Requirements for Nucleolar Localization of Human T Cell Leukemia Virus Type I PX Protein, Which Regulates Viral RNA Processing," *Cell* 55(2):197-209 (1988).
Sukegawa-Hayasaka, et al., "Effect of Hunter Disease (Mucopolysaccharidosis Type II) Mutations on Molecular Phenotypes of Iduronate-2-Sulfatase: Enzymatic Activity, Protein Processing and Structural Analysis," *J Inherit Metab Dis* 29(6):755-761 (2006).
Swarts, et al., "DNA-Guided DNA Interference By a Prokaryotic Argonaute," *Nature* 507(7491):258-261 (2014).
Urnov, et al., "Highly Efficient Endogenous Human Gene Correction Using Designed Zinc-Finger Nucleases," *Nature* 435(7042):646-651 (2005).
Vislovukh, et al., "Role of 3'-Untranslated Region Translational Control in Cancer Development, Diagnostics and Treatment," *World J Biol Chem* 5(1):40-57 (2014).
Wah, et al., "Structure of the Multimodular Endonuclease FokI Bound To DNA," *Nature* 388:97-100 (1997).
Woychik, et al., "Requirement for the 3' Flanking Region of the Bovine Growth Hormone Gene for Accurate Polyadenylylation," *Proc Natl Acad Sci* 81(13):3944-3948 (1984).
Yin, et al., "Therapeutic Genome Editing By Combined Viral and Non-Viral Delivery of CRISPR System Components In Vivo," *Nat Biotech* 34(3):328 (2016).
Young, et al., "A Clinical and Genetic Study of Hunter's Syndrome. 2 Differences Between the Mild and Severe Forms," *Med Genet.* 19(6):408-411 (1982).
Zanta-Boussif, et al., "Validation of a Mutated Pre Sequence Allowing High and Sustained Transgene Expression While Abrogating WHV-X Protein Synthesis: Application to the Gene Therapy of WAS," *Gene Ther* 16(5):605-619 (2009).
International Search Report and Written Opinion on PCT Appl. Ser. No. PCT/US2019/017273 dated Jul. 2, 2019 (12 pages).
Extended European Search Report mailed in EP 19751240.3 dated Oct. 28, 2021 (7 pages).

\* cited by examiner

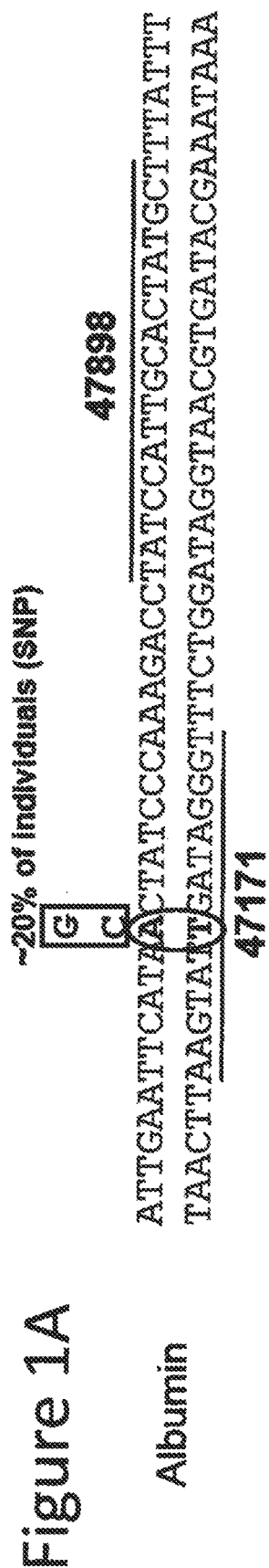
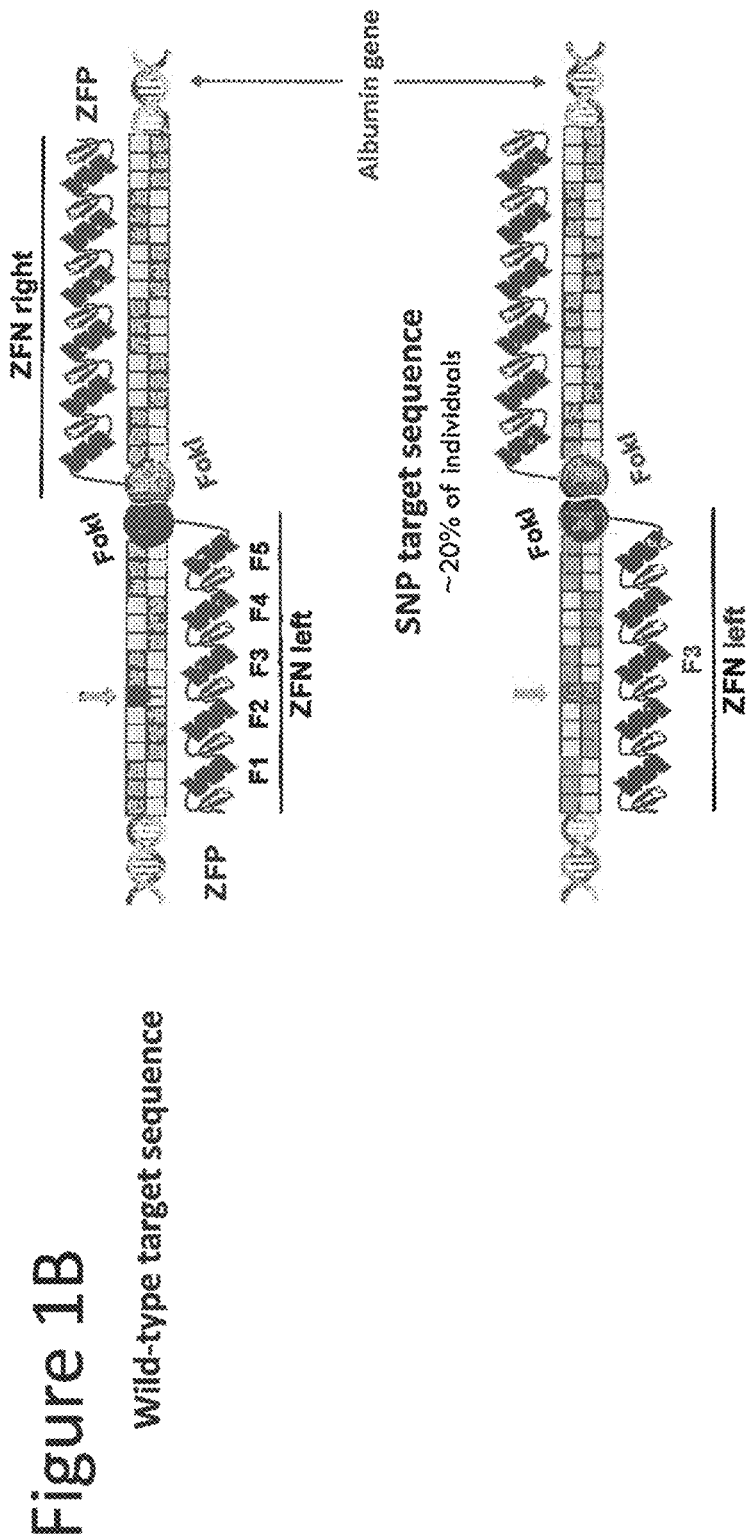
Figure 1A
Figure 1B

Figure 3A

| ZFN1 | | ZFN2 | | Albumin %indels | | | | SMCHD1 |
|---|---|---|---|---|---|---|---|---|
| | | | | 2000 ng | 62.5 ng | 31.25 ng | 15.6 ng | 2000 ng |
| 71545 | 42875-F1F3Q-R416H | 71673 | 47898-F3Q-R416H | 82.4 | 39.8 | 6.1 | 0.8 | 0.017 |
| 71545 | 42875-F1F3Q-R416H | 71721 | 47874-F3Q-R416H | 82.7 | 44.5 | 9.2 | 2.0 | 0.018 |
| 71545 | 42875-F1F3Q-R416H | 71739 | 47874-F1F3Q-341BP | 84.2 | 63.3 | 19.6 | 2.8 | 0.011 |
| 71545 | 42875-F1F3Q-R416H | 71741 | 47874-F1F3Q-L424F | 85.1 | 61.1 | 23.9 | 4.5 | 0.017 |
| 71557 | 42875-F1F3Q-N542D | 71721 | 47874-F3Q-R416H | 80.8 | 46.8 | 8.9 | 1.8 | 0.018 |
| 71557 | 42875-F1F3Q-N542D | 71728 | 47874-F3Q-P478S | 80.9 | 53.9 | 20.6 | 4.6 | 0.012 |
| 71639 | 42908-F1F3Q-WT | 71696 | 47898-F1F3Q-P478S | 70.3 | 16.6 | 1.0 | 0.1 | 0.012 |
| 71641 | 42908-F1F3Q-R416H | 71673 | 47898-F3Q-R416H | 72.6 | 12.9 | 0.8 | 0.1 | 0.008 |
| 71641 | 42908-F1F3Q-R416H | 71741 | 47874-F1F3Q-L424F | 69.3 | 38.3 | 6.5 | 0.5 | 0.009 |
| 71653 | 42908-F1F3Q-N542D | 71673 | 47898-F3Q-R416H | 67.4 | 11.5 | 0.8 | 0.0 | 0.014 |
| 71653 | 42908-F1F3Q-N542D | 71721 | 47874-F3Q-R416H | 86.4 | 19.9 | 2.5 | 0.2 | 0.018 |
| 71653 | 42908-F1F3Q-N542D | 71741 | 47874-F1F3Q-L424F | 87.7 | 37.9 | 4.8 | 0.3 | 0.011 |
| 47171 | Parent | 47898 | Parent | 78.9 | 21.1 | 1.9 | 0.2 | |

GFP

| 0.098 | Albumin Plate 1 |
| 0.033 | Albumin Plate 2 |
| 0.008 | SMCHD1 |

Figure 3C

| | Gene/ Location | Capture events | K562 % indels | HepG2 % indels |
|---|---|---|---|---|
| | ALS (on-target) | | 97.7% | 98.9% |
| 1 | SKA2 | 18 | ns | ns |
| 2 | Chr5 (intergenic) | 12 | ns | ns |
| 3 | Chr9 (intergenic) | 11 | ns | ns |
| 4 | AC079807.4 | 10 | ns | ns |
| 5 | Chr1 (intergenic) | 9 | ns | ns |
| 6 | CSMD3 | 9 | ns | ns |
| 7 | Chr18 (intergenic) | 9 | ns | ns |
| 8 | Chr19 (intergenic) | 9 | ns | ns |
| 9 | Chr1 (intergenic) | 8 | ns | 0.08^ |
| 10 | HECTD4 | 8 | ns | ns |
| 11 | Chr17 (intergenic) | 8 | ns | ns |
| 12 | Chr4 (intergenic) | 8 | ND | ND |
| 13 | CSMD3 | 8 | ns | ns |
| 14 | Chr11 (intergenic) | 8 | ns | ns |
| 15 | Chr1 (intergenic) | 7 | ns | ns |
| 16 | AKAP6 | 7 | ND | ND |
| 17 | Chr19 (intergenic) | 7 | ns | ns |
| 18 | OS9PL8 | 7 | ns | ns |
| 19 | QPCT | 7 | ns | ns |
| 20 | RP11-269F21.3 | 7 | ns | ns |
| 21 | LPHN3 | 7 | ns | ns |
| 22 | CYFIP2 | 7 | ns | ns |
| 23 | AUTS2 | 7 | ns | ns |
| 24 | COL4A6 | 7 | ns | ns |
| 25 | ChrX (intergenic) | 7 | ns | ns |
| 26 | ACAN | 7 | ns | ns |

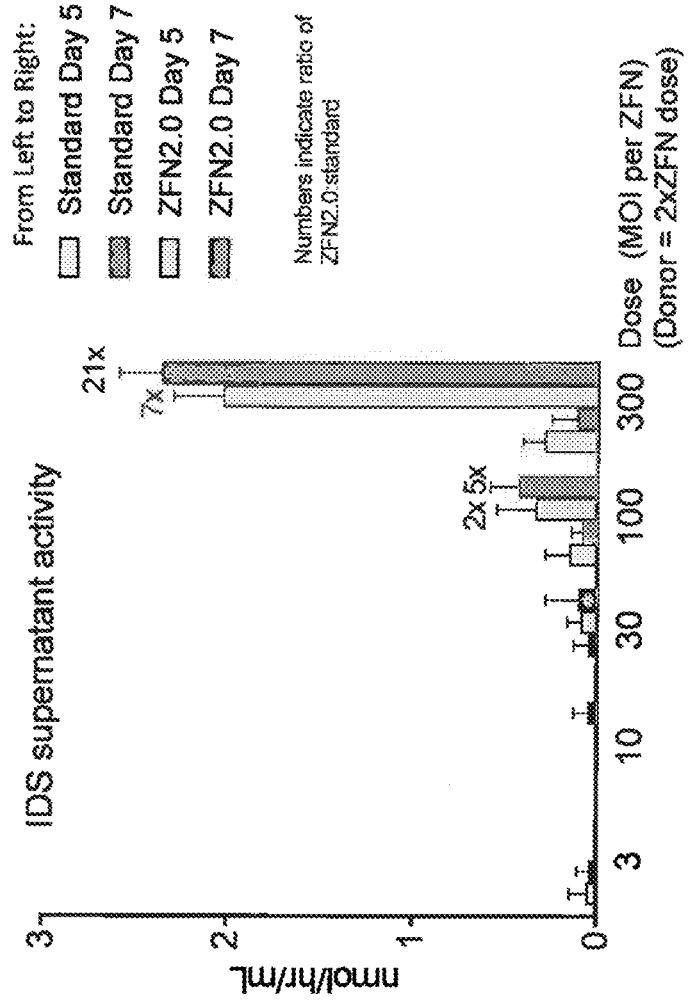
Figure 3E(ii)

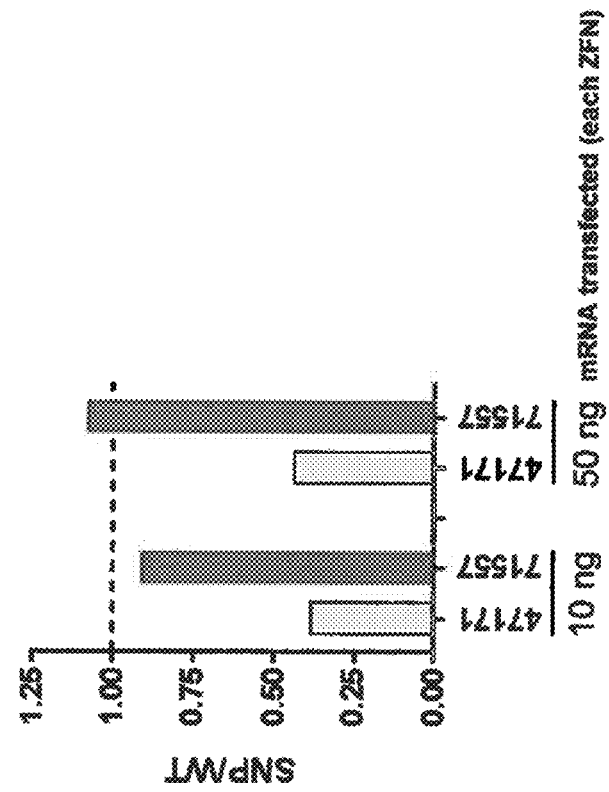
Figure 3F(i)
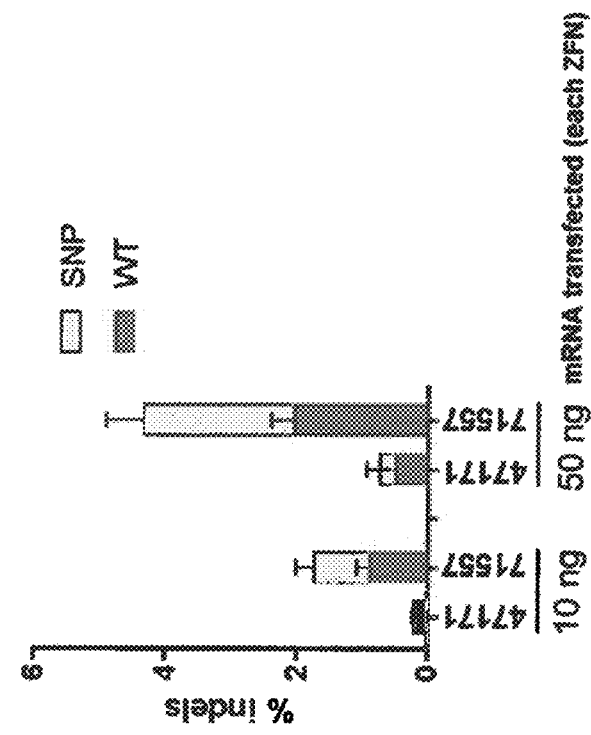
Figure 3F(ii)

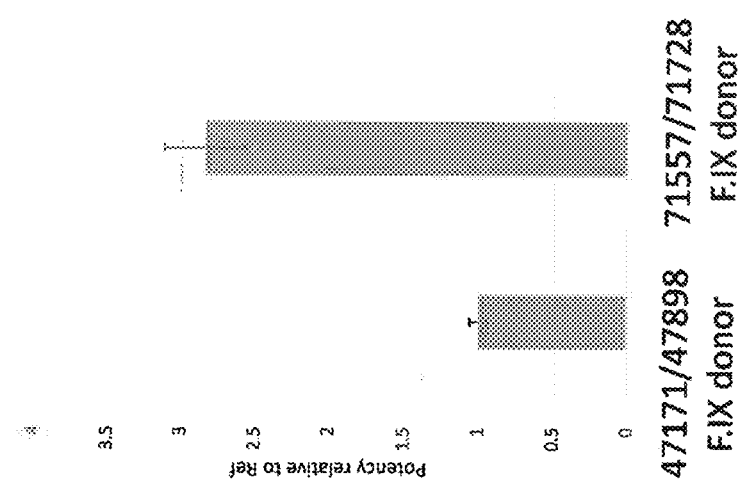

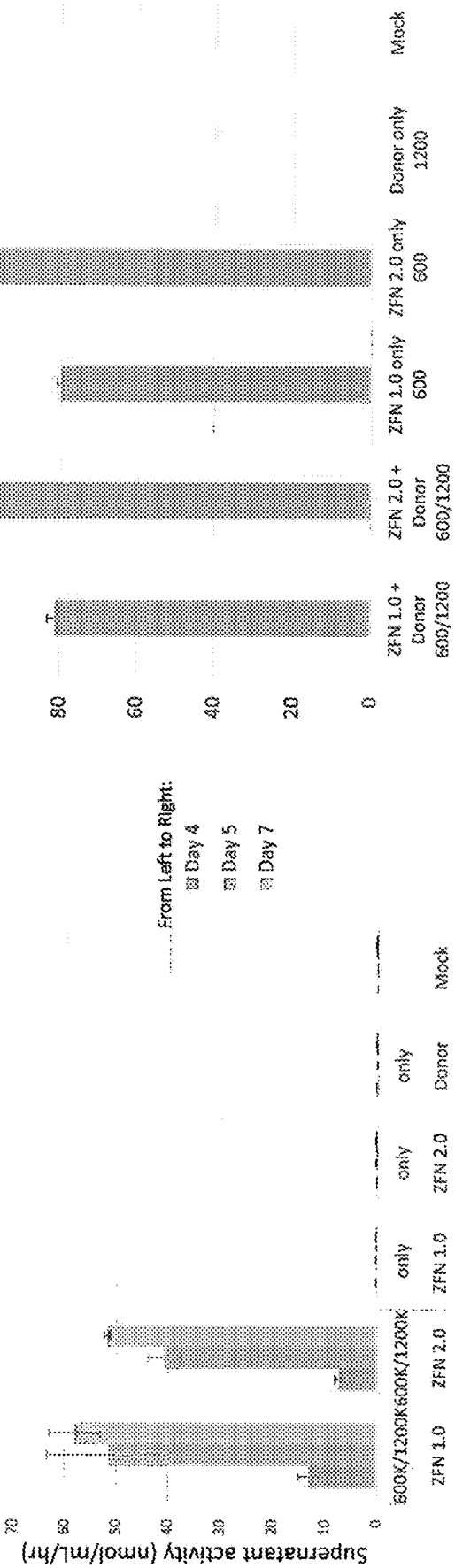

ENGINEERED TARGET SPECIFIC NUCLEASES

CROSS-REFERENCE TO RELATED APPLICATIONS

The present application claims the benefit of U.S. Provisional Application No. 62/628,016, filed Feb. 8, 2018; U.S. Provisional Application No. 62/728,226, filed Sep. 7, 2018; U.S. Provisional Application No. 62/758,786, filed Nov. 12, 2018; U.S. Provisional Application No. 62/795,937, filed Jan. 23, 2019; and U.S. Provisional Application No. 62/802,092, filed Feb. 6, 2019, the disclosures of which are hereby incorporated by reference in their entireties.

STATEMENT OF RIGHTS TO INVENTIONS MADE UNDER FEDERALLY SPONSORED RESEARCH

Not applicable.

SEQUENCE LISTING

The instant application contains a Sequence Listing which has been submitted electronically in ASCII format and is hereby incorporated by reference in its entirety. Said ASCII copy, created on Jan. 29, 2019, is named 83250169SL.txt and is 54,299 bytes in size.

TECHNICAL FIELD

The present disclosure is in the fields of polypeptide and genome engineering and homologous recombination.

BACKGROUND

Artificial nucleases, such as engineered zinc finger nucleases (ZFN), transcription-activator like effector nucleases (TALENs), the CRISPR/Cas system with an engineered crRNA/tracr RNA ('single guide RNA'), also referred to as RNA guided nucleases, and/or nucleases based on the Argonaute system (e.g., from *T. thermophilus*, known as 'TtAgo', (Swarts et al (2014) *Nature* 507(7491): 258-261), comprise DNA binding domains (nucleotide or polypeptide) associated with or operably linked to cleavage domains, and have been used for targeted alteration of genomic sequences. For example, nucleases have been used to insert exogenous sequences, inactivate one or more endogenous genes, create organisms (e.g., crops) and cell lines with altered gene expression patterns, and the like. See, e.g., U.S. Pat. Nos. 9,255,250; 9,200,266; 9,045,763; 9,005,973; 8,956,828; 8,945,868; 8,703,489; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 201000218264; 20120017290; 20110265198; 20130137104; 20130122591; 20130177983 and 20130177960 and 20150056705. For instance, a pair of nucleases (e.g., zinc finger nucleases, TALENs, dCas-Fok fusions) may be used to cleave genomic sequences. Each member of the pair generally includes an engineered (non-naturally occurring) DNA-binding protein linked to one or more cleavage domains (or half-domains) of a nuclease. When the DNA-binding proteins bind to their target sites, the cleavage domains that are linked to those DNA binding proteins are positioned such that dimerization and subsequent cleavage of the genome can occur.

With regards to zinc finger proteins, the specificity of a ZFP for a target DNA sequence is dependent upon sequence specific contacts between the zinc finger domains and specific DNA bases. In addition, the zinc finger domains also comprise amino acid residues that take part in non-specific ion pair interactions with the phosphates of the DNA backbone. Elrod-Erickson et al ((1996) *Structure* 4:1171) demonstrated through co-crystallization of a zinc finger protein and its cognate DNA target that there are specific amino acids capable of interacting with the phosphates on the DNA backbone through formation of hydrogen bonds. Zinc finger proteins that employ the well-known Zif268 backbone typically have an arginine as the amino terminal residue of their second strand of β-sheet, which is also the second position carboxyl-terminal to the second invariant cysteine. This position can be referred to as (−5) within each zinc finger domain, as it is $5^{th}$ residue preceding the start of the α-helix. The arginine at this position can interact with a phosphate on the DNA backbone via formation of a charged hydrogen bond with its side-chain guanidinium group. Zinc finger proteins in the Zif268 backbone also frequently have a lysine at a position that is 4 residues amino-terminal to the first invariant cysteine. This position can be referred to as (−14) within each finger, as it is $14^{th}$ residue preceding the start of the α-helix for zinc fingers with two residues between the zinc coordinating cysteine residues. The lysine can interact with a phosphate on the DNA backbone via formation of a water-mediated charged hydrogen bond with its side-chain amino group. Since phosphate groups are found all along the DNA backbone, this type of interaction between the zinc finger and a DNA molecule is generally considered to be non-sequence specific (J. Miller, Massachusetts Institute of Technology Ph.D. Thesis, 2002).

To decrease off-target cleavage events, engineered obligate heterodimeric cleavage half-domains have been developed. See, e.g., U.S. Pat. Nos. 7,914,796; 8,034,598; 8,962,281 and 8,623,618; U.S. Patent Publication Nos. 20080131962 and 20120040398. These obligate heterodimers dimerize and cleave their targets only when the differing engineered cleavage domains are positioned at the appropriate target site by the ZFPs, thereby reducing and/or eliminating monomeric off-target cleavage.

Another area that may be explored for producing the most efficient artificial nuclease is in the non-coding sequences that may be included in a gene encoding an artificial nuclease. For example, 3' untranslated regions ("UTR") in an mRNA molecule can play an important role in the regulation of gene expression at the post-transcriptional level. The 3' UTR controls the expression of an mRNA by orchestrated interactions between the structural components of mRNAs and specific trans-acting RNA binding proteins and non-coding RNAs (Vislovukh et al (2014) *World J Biol Chem* 5(1): 40-57), and also comprises the polyadenylation sequences. Examples of commonly used 3' UTRs are the SV40 virus polyA fragment, the poly A region from bovine growth hormone (BGH) gene and the rabbit beta-globin UTR (Ludwig, Dale (2006) *BioProcess International*, supplement). 5' UTRs can be 100-200 bp in length in higher eukaryotes and comprise a high GC content (often >60%). These sequences can include elements such as a Kozak consensus sequence for ribosome binding and sequences for cap attachment. The high GC content can result in complex hairpin structures (known as cis-acting regulatory sequences) which can affect translation efficiency and are known as internal ribosome entry sites (IRES). 5' UTRs can also have sequences for binding gene-specific regulatory proteins (iron regulatory proteins for example) for regulating expression and can also play a role in other functions such as providing interaction with the translation machinery (Araujo et al (2012) *Comp and Funct Genom* (2012) doi: 10.1155/2012/475731). An example of a commonly used 5'UTR sequences is the beta-globin 5'UTR. UTR can also have a role in the spatial control of gene regulation at the post-transcriptional level, often mediated by cis acting elements in the 3' UTR (Mignone et al (2002) *Genome Biol* 3(3): PMCID: PMC139023).

However, there remains a need for additional methods and compositions to engineered nuclease cleavage systems to provide enhanced transcription/translation efficiency and to increase nuclease activity and/or specificity.

SUMMARY

The present disclosure provides methods and compositions to increase expression of an artificial nuclease, as well as increase the efficiency (activity) and/or specificity of a nuclease (e.g., nuclease pair) for its intended target. Thus, described herein are polynucleotides (e.g., DNA expression vector or mRNA) for expressing artificial nucleases (e.g., zinc finger nucleases (ZFNs), TALENs, CRISPR/Cas nucleases) comprising engineered promoters comprising elements in the 5' and/or 3' untranslated sequences that enhance expression of the artificial nucleases. Optionally, the nuclease-encoding polynucleotides further comprise sequences encoding small peptides (including but not limited to polycationic peptides such as peptide tags and/or nuclear localization sequences), and/or comprise mutations in one or more of the DNA binding domain regions (e.g., the backbone of a zinc finger protein or TALE) and/or one or more mutations in a FokI nuclease cleavage domain or cleavage half domain. When these polynucleotide components are used individually or in any combination (e.g., peptide sequence such as FLAG (e.g., 3× FLAG), NLS, WPRE and/or poly A signal in any combination), the methods and compositions of the invention provide surprising and unexpected increases in expression of artificial nucleases with increased efficiency of cleavage and/or targeted integration of a transgene (e.g., 2, 3, 4, 5, 6, 7, 8, 9, 10, 11, 12, 13, 14, 15, 16, 17, 18, 19, 20 or more fold cleavage as compared to nucleases without the sequences/modifications described herein) in vitro or in vivo and/or targeting specificity (reduced off-target effects). The disclosure also provides methods of using these compositions for targeted cleavage of cellular chromatin in a region of interest and/or integration of a transgene via targeted integration at a predetermined region of interest in cells.

Thus, described herein is a polynucleotide (mRNA, plasmid, viral vector such as AAV) encoding a nuclease (e.g., ZFN, TALEN, CRISPR/Cas nuclease, etc.), the polynucleotide further comprising at least one, two, three, four, five, six, seven or eight of any combination of the following elements: (i) a sequence encoding a polycationic sequence (e.g., a 3× FLAG sequence), optionally 5' to the nuclease-encoding sequence; (ii) a 5'UTR sequence (e.g., a *Xenopus* beta-globin sequence such as shown in SEQ ID NO:1), optionally 5' to the nuclease-encoding sequence; (iii) a WPRE sequence, 3' and/or 5' to the nuclease coding sequence; (iv) modifications to the sequence encoding backbone (non-DNA binding residues) of the nuclease domain (e.g., phosphate backbone residues of a ZFN); (v) modifications to the cleavage domain sequence of the nuclease (e.g., engineered FokI domains); (vi) a tissue specific promoter and/or enhancer (e.g., hAAT, ApoE, etc.), optionally operably linked to the sequence encoding the nuclease; (vii) a NLS sequence (5' or 3' to the nuclease encoding sequence); and/or (viii) a polyA sequence. In certain embodiments, the polynucleotide is mRNA. In other embodiments, the polynucleotide is an AAV vector, further optionally comprising an ITR, for example an AAV vector as shown in any of the constructs the appended Figures and/or Tables. A single polynucleotide may encode some or all components of the nuclease, e.g., a pair of ZFNs, a single guide RNA, etc. Alternatively, separate polynucleotides (of the same or different types) may encode components of the nuclease, for example, separate nucleotides each encoding one ZFN or TALEN of a ZFN or TALEN pair. Thus, provided herein are one or more polynucleotides (e.g., AAV vectors) encoding one or more nucleases (e.g., ZFNs). The polynucleotides described herein can be used for in vitro, ex vivo and/or in vivo methods for targeted cleavage and/or integration of at least one donor and may increase nuclease activity (cleavage and/or integration) and/or specificity (on-target as compared to off-target activity) by 1-50 fold (or any value therebetween, including 1, 2, 3, 4, 5, 6, 7, 8, 9, 10, 11, 12, 13, 14, 15, 16, 17, 18. 19, 20, etc. fold).

In one aspect, the invention describes a polynucleotide comprising a tissue specific promoter for expressing an artificial nuclease in a desired tissue. In some embodiments, the tissue specific promoter is a liver-specific promoter. In further embodiments, the liver specific promoter is a humanal anti-trypsin promoter (hAAT) or a transthyretin minimal promoter (see U.S. Patent publication 20170119906). In some instances, the liver specific promoter comprises an ApoE enhancer sequence (Shachter et al. (1993) *J Lipid Res* 34(10):1699-707). In some embodiments, the liver specific promoter comprises one or more ApoE enhancer sequences (e.g., 1, 2, 3 and/or 4; see Okuyama et al. (1996) *Hum Gen Ther* 7(5):637-45). In further embodiments, the promoter is linked to an intron. In preferred embodiments, the intron is an HGG-IGG chimeric intron comprising the 5' donor site from the first intron of the human β-globin gene and the branch and 3' acceptor site from the intron of an immunoglobulin gene heavy chain variable region. The polynucleotides described herein may be cDNA constructs (for example carried on a viral vector such as AAV), mRNA, plasmid DNA, or part of an expression cassette for insertion into a genome.

Thus, in one aspect, described herein is an mRNA or AAV vector encoding a nuclease, the mRNA or AAV vector comprising elements for increasing transcriptional and translational efficiency. In some embodiments, the elements comprise untranslated sequences such as natural or artificial 5' and/or 3' UTR sequences. In some aspects, a 5' UTR sequence is included in an expression cassette, while in others, a 3' UTR sequence is used. In preferred embodiments, an mRNA or AAV encoding an artificial nuclease comprises both a 5' UTR and a 3' UTR. In one embodiment, the 5' UTR is a *Xenopus* β-globin UTR (see Falcone and Andrews (1991) Mol Cell Bio 11(5): 2656-2664; Krieg and Melton (1994) *Nuc Acid Res* 12(18):7057). In preferred embodiments, the DNA sequence encoding the *Xenopus* β-globin UTR is 5' [TG] CTTGTTCTTTTTGCAGAAGCTCAGAATAAACGCT-CAACTTTGGCAGAT (SEQ ID NO:1) (where TG is optional). In some aspects, the mRNA or AAV encoding the nuclease comprises a 3' WPRE sequence (see U.S. Patent publication 20160326548). In further embodiments, the WPRE element is a mutated in the 'X' region to prevent expression of Protein X (see U.S. Pat. No. 7,419,829). In some embodiments, the mutated WPRE sequence is a truncated WPRE element. In some embodiments the mutated WPRE sequence is mutated in the X region of the J02442 or J04514 woodchuck hepatitis virus (Galibert et al (1982) *J. Virol* 41(1): 51-65; Zanta-Boussif et al. (2009) *Gene Ther* 16(5):605-619). Non-limiting examples of WPRE sequences that may be used in the polynucleotides described herein are shown below in the Examples. In further aspects, the 3' UTR comprises a poly A signal sequence. The poly A signal may be 3' or 5' to the WPRE sequence when these elements are used in combination. In preferred embodiments, the poly A signal sequence is the bovine Growth Hormone signal sequence (see Woychik et al (1984) *Proc Natl Acad Sci* 81(13):3944-8). The nuclease-encoding polynucleotides (mRNA, AAV vectors) as described herein may further include modifications to the nuclease encoding sequence, for example modifications to the backbone region of a ZFP DNA-binding domain of the nuclease and/or modifications to the cleavage domain (or cleavage half-domain) of the nuclease(s).

In another aspect, described herein is an engineered nuclease cleavage half domain comprising one or more mutations as compared to a parental (e.g., wild-type) cleavage domain from which these mutants are derived and/or a polynucleotide (mRNA) comprising these cleavage domains. Mutations as described herein, include but are not limited to, mutations that change the charge of the cleavage domain, for example mutations of positively charged residues to non-positively charged residues (e.g., mutations of K and R residues (e.g., mutated to S); N residues (e.g., to D), and Q residues (e.g., to E); mutations to residues that are predicted to be close to the DNA backbone based on molecular modeling and that show variation in FokI homologs; and/or mutations at other residues (e.g., U.S. Pat. No. 8,623,618 and Guo et al, (2010) *J. Mol. Biol.* 400(1): 96-107).

In certain embodiments, the engineered cleavage half domains are derived from FokI or FokI homologues and comprise a mutation in one or more of amino acid residues 416, 422, 447, 448, and/or 525, numbered relative to the wild-type full length FokI as shown in SEQ ID NO:2 or corresponding residues in FokI homologues In other embodiments, the cleavage half domains derived from FokI comprises a mutation in one or more of amino acid residues 414-426, 443-450, 467-488, 501-502, and/or 521-531, including one or more of 387, 393, 394, 398, 400, 416, 418, 422, 427, 434, 439, 441, 442, 444, 446, 448, 472, 473, 476, 478, 479, 480, 481, 487, 495, 497, 506, 516, 523, 525, 527, 529, 534, 542, 559, 569, 570, and/or 571, numbered relative to wild-type FokI or corresponding residues in any FokI homologue. The mutations may include mutations to residues found in natural restriction enzymes homologous to FokI at the corresponding positions. In certain embodiments, the mutations are substitutions, for example substitution of the wild-type residue with any different amino acid, for example alanine (A), cysteine (C), aspartic acid (D), glutamic acid (E), histidine (H), phenylalanine (F), glycine (G), asparagine (N), serine (S) or threonine (T). In certain embodiments, the FokI nuclease domain comprises a mutation at one or more of 416, 422, 447, 479 and/or 525 (numbered relative to wild-type, SEQ ID NO:2). The nuclease domains may also comprise one or more mutations at positions 418, 432, 441, 448, 476, 481, 483, 486, 487, 490, 496, 499, 523, 527, 537, 538 and 559, including but not limited to ELD, KKR, ELE, KKS. See, e.g., U.S. Pat. No. 8,623,618. In still further embodiments, the cleavage domain includes mutations at one or more of the residues (e.g., 419, 420, 425, 446, 447, 470, 471, 472, 475, 478, 480, 492, 500, 502, 521, 523, 526, 530, 536, 540, 545, 573 and/or 574). In certain embodiments, the variant cleavage domains described herein include mutations to the residues involved in nuclease dimerization (dimerization domain mutations), and one or more additional mutations; for example to phosphate contact residues: e.g. dimerization mutants (such as ELD, KKR, ELE, KKS, etc.) in combination with one, two, three, four, five, six or more mutations at amino acid positions outside of the dimerization domain, for example in amino acid residues that may participate in phosphate contact. In a preferred embodiment, the mutation at positions 416, 422, 447, 448 and/or 525 comprise replacement of a positively charged amino acid with an uncharged or a negatively charged amino acid. In other embodiments, mutations at positions 446, 472 and/or 478 (and optionally additional residues for example in the dimerization or catalytic domains) are made. In certain embodiments, the engineered cleavage half-domain comprises a mutation at position 542 (e.g., N542D) and/or 478 (e.g., P478S). Also described are heterodimers of engineered cleavage domains, for example, a first (left) nuclease comprising one engineered cleavage domain (e.g., N542D) and a second nuclease comprising a different engineered cleavage domain (e.g., P478S).

Any of the engineered cleavage half domains described above may be incorporated into artificial nucleases (and polynucleotides expressing these artificial nucleases), for example by associating them with a DNA-binding domain, including but not limited to zinc finger nucleases, TALENs, CRISPR/Cas nucleases, and the like. The zinc finger proteins of the zinc finger nucleases may comprise non-canonical zinc-coordinating residues (e.g. CCHC rather than the canonical C2H2 configuration, see U.S. Pat. No. 9,234,187).

In another aspect, fusion molecules comprising a DNA binding domain and an engineered FokI or homologue thereof cleavage half-domain as described herein that produce an artificial nuclease are provided. In certain embodiments, the DNA-binding domain of the fusion molecule is a zinc finger binding domain (e.g., an engineered zinc finger binding domain). In other embodiments, the DNA-binding domain is a TALE DNA-binding domain. In still further embodiments, the DNA binding domain comprises a DNA binding molecule (e.g. guide RNA) and a catalytically inactive Cas9 or Cfp1 protein (dCas9 or dCfp1). In some embodiments, the engineered fusion molecules form a nuclease complex with a catalytically inactive engineered cleavage half-domain such that the dimeric nuclease is only capable of cleaving only one strand of a double-stranded DNA molecule, forming a nickase (see U.S. Pat. No. 9,200,266).

The methods and compositions of the invention can also include mutations to one or more amino acids within the DNA binding domain outside the residues that recognize the nucleotides of the target sequence (e.g., one or more mutations to the 'ZFP backbone' (outside the DNA recognition helix region) or to the 'TALE backbone' (outside of the RVDs)) that can interact non-specifically with phosphates on the DNA backbone. Thus, in certain embodiments, the invention includes mutations of cationic amino acid residues in the ZFP backbone that are not required for nucleotide target specificity. In some embodiments, these mutations in the ZFP backbone comprise mutating a cationic amino acid residue to a neutral or anionic amino acid residue. In some embodiments, these mutations in the ZFP backbone comprise mutating a polar amino acid residue to a neutral or non-polar amino acid residue. In preferred embodiments, mutations at made at position (−5), (−9) and/or position (−14) relative to the DNA binding helix. In some embodiments, a zinc finger may comprise one or more mutations at (−5), (−9) and/or (−14). In further embodiments, one or more zinc fingers in a multi-finger zinc finger protein may comprise mutations in (−5), (−9) and/or (−14). In some embodiments, the amino acids at (−5), (−9) and/or (−14) (e.g. an arginine (R) or lysine (K)) are mutated to an alanine (A), leucine (L), Ser (S), Asp (N), Glu (E), Tyr (Y) and/or glutamine (Q). See, e.g., U.S. Publication No. US-2018-0087072.

In another aspect, polynucleotides encoding any of the engineered cleavage half-domains or fusion molecules (including artificial nucleases) as described herein are provided. Non-limiting examples of suitable polynucleotides include mRNA, cDNA, viral vectors (AAV, Ad, LV), and/or non-viral vectors (plasmid vectors).

In some aspects, the methods and compositions of the invention include the use of sequences encoding exogenous peptide sequences fused to eukaryotic transgene sequences. In some embodiments, exogenous peptides are fused to protein sequences post-translationally, and in other embodiments, the sequences encoding the exogenous peptides are linked in frame (3' and/or 5') to sequences encoding the artificial nuclease (e.g., a fusion protein). The exogenous peptides may encode sequences useful for purification or labeling, e.g. affinity purification or immunohistochemistry. Examples of such peptides are polyhistidine tags ("His tag", Hochuli et al (1988), *Bio/Technol* 6(11):1321-5) or cationic peptide tags such as Flag tags (Hopp et al (1988) *Bio/Technol* 6(10):1204-10; Hernan et al. (2000) *BioTechniques* 28(4), 789-793). One or more (1, 2, 3, 4, 5 or more) of these peptide tag sequences can be used in any combinations. In some embodiments, the sequence encoding an exogenous Flag peptide comprising the sequence N-term DYKDDDK (SEQ ID NO:3) is fused in frame at the C-terminus or N-terminus of a sequence encoding an artificial nuclease. In preferred embodiments, a sequence encoding 3 FLAG sequences (3× FLAG peptide) is used (see U.S. Pat. No. 6,379,903), wherein the amino acid sequence is N-term (M)DYKDHDG-DYKDHDI-DYKDDDDK (SEQ ID NO:4), where an N-terminal methionine (M) is optional. Inclusion of one or more of such peptide sequences (e.g., polycationic sequences such as 3× FLAG) can increase nuclease (cleavage) activity by 2, 3, 4, 5, 6, 7, 8, 9, 10, 11 or more fold) as compared to nucleases without the peptide sequences.

In some aspects, the mRNA encoding an artificial nuclease comprises a nuclear localization peptide sequence (NLS). In some embodiments, the NLS comprises the sequence PKKKRKV (SEQ ID NO:5) from the SV40 virus large T gene (see Kalderon et al (1984) *Nature* 311(5981): 33-8) while in others, the NLS comprises the sequence PAAKRVKLD (SEQ ID NO:6) from the c-myc protein (see Dang and Lee (1988) *Mol Cell Biol* 8(10):4048-54). In some embodiments, the NLS comprises the sequence EGAP-PAKRAR (SEQ ID NO:7) from the hepatitis delta virus (see Alves et al (2008) Virology 370: 12-21) or VSRKRPRP (SEQ ID NO:8) from the polyoma T protein (Richardson et al (1986) *Cell* 44(1):77-85). In other embodiments, the NLS comprises the sequence KRPAATKKAGQAKKKKLD (SEQ ID NO:9), derived from the nucleoplasmin carboxy tail (see Dingwall (1988) *J Cell Biol* 107:841-849 and Robbins et al (1991) *Cell* 64(3):615-23), while in some embodiments, the NLS comprises the sequence NQSSNFGPMKGGNFGGRSSGPYGGGGQYFAK-PRNQGGY (SEQ ID NO:10) first described by Siomi and Dreyfuss (Siomi and Dreyfus (1995) *J Cell Biol* 129(3):551-560). In further embodiments, the NLS comprises the sequence PKTRRRPRRSQRKRPPT (SEQ ID NO:11) from the Rex protein in HTLV-1 (Siomi et al (1988) *Cell* 55(2): 197-209). Inclusion of one or more of NLS sequences as described herein can increase nuclease (cleavage) activity by 2, 3, 4, 5, 6, 7, 8, 9, 10, 11 or more fold) as compared to nucleases without the peptide sequences.

In yet another aspect, cells comprising any of the nucleases, polypeptides (e.g., fusion molecules or fusion polypeptides) and/or polynucleotides as described herein are also provided. In one embodiment, the cells comprise a pair of fusion polypeptides, one fusion polypeptide comprising, in addition to one or more mutations in amino acid residues 393, 394, 398, 416, 421, 422, 442, 444, 447, 448, 473, 480, 530 and/or 525, an ELD or ELE cleavage half-domain and one fusion polypeptide comprising, in addition to one or more mutations at residues 393, 394, 398, 416, 421, 422, 442, 444, 446, 447, 448, 472, 473, 478, 480, 530 and/or 525, a KKK or KKR cleavage half-domain (see U.S. Pat. No. 8,962,281). In some embodiments, one fusion protein comprises a mutation in residue 542 of FokI (residue 159 of the cleavage domain) such as N542D and one fusion polypeptide comprises a mutation in residue 478 of FokI (residue 95 of the cleavage domain) such as P478S.

In any of these fusion polypeptides described herein, the ZFP partners may further comprise mutations in the zinc finger DNA binding domain in the (−5), (−9) and/or (−14) positions. In some embodiments, the Arg (R) at position −5 is changed to a Tyr (Y), Asp (N), Glu (E), Leu (L), Gln (Q), or Ala (A). In other embodiments, the Arg (R) at position (−9) is replaced with Ser (S), Asp (N), or Glu (E). In further embodiments, the Arg (R) at position (−14) is replaced with Ser (S) or Gln (Q). In other embodiments, the fusion polypeptides can comprise mutations in the zinc finger DNA binding domain where the amino acids at the (−5), (−9) and/or (−14) positions are changed to any of the above listed amino acids in any combination.

Also provided herein are cells that have been modified by the polypeptides and/or polynucleotides of the invention, including cells descended and/or differentiated from cells comprising one or more artificial nucleases as described herein. In some embodiments, the cells comprise a nuclease-mediated insertion of a transgene, or a nuclease-mediated knock out of a gene. The modified cells, and any cells derived from the modified cells do not necessarily comprise the nucleases of the invention more than transiently, but the genomic modifications mediated by such nucleases remain.

In yet another aspect, methods for targeted cleavage of cellular chromatin in a region of interest; methods of causing homologous recombination to occur in a cell; methods of treating infection; and/or methods of treating disease are provided. These methods maybe practiced in vitro, ex vivo or in vivo or a combination thereof. The methods involve cleaving cellular chromatin at a predetermined region of interest in cells using one or more artificial nucleases as described herein. In certain embodiments, a pair of fusion polypeptides as described herein (i.e., a pair of fusion polypeptides in which one or both fusion polypeptide(s) comprises the engineered cleavage half-domains as described herein). In certain embodiments, the targeted cleavage of the on-target site is increased by at least 50 to 200% (or any value therebetween) or more, including 50%-60% (or any value therebetween), 60%-70% (or any value therebetween), 70%-80% (or any value therebetween), 80%-90% (or any value therebetween, 90% to 200% (or any value therebetween), as compared to cleavage domains without the mutations as described herein. Similarly, using the methods and compositions as described herein, off-target site cleavage is reduced by 1-100 or more-fold, including but not limited to 1-50-fold (or any value therebetween). In certain embodiments, the targeted cleavage of the nuclease activity is increased by at least 50 to 200% (or any value therebetween) or more, including 50%-60% (or any value therebetween), 60%-70% (or any value therebetween), 70%-80% (or any value therebetween), 80%-90% (or any value therebetween, 90% to 200% (or any value therebetween) or by 1-100 or more-fold, including but not limited to 1-50-fold (or any value therebetween), as compared to when constructs encoding the nucleases described herein do not include the modifications (enhancements).

The artificial nucleases (and polynucleotides encoding the same) described herein can be used in methods for targeted cleavage of cellular chromatin in a region of interest and/or homologous recombination at a predetermined region of interest in cells. Cells include cultured cells, cell lines, cells in an organism, cells that have been removed from an organism for treatment in cases where the cells and/or their descendants will be returned to the organism after treatment, and cells removed from an organism, modified using the fusion molecules of the invention, and then returned to the organism in a method of treatment (cell therapy). A region of interest in cellular chromatin can be, for example, a genomic sequence or portion thereof. Compositions include fusion molecules or polynucleotides encoding fusion molecules that comprise a DNA binding molecule (e.g., an engineered zinc finger or TALE binding domain or an engineered CRISPR guide RNA) and a cleavage half domain as described.

A fusion molecule can be expressed in a cell, e.g., by delivering the fusion molecule to the cell as a polypeptide, or by delivering a polynucleotide encoding the fusion molecule to a cell, wherein the polynucleotide, if DNA, is transcribed and is translated, to generate the fusion molecule. Further, if the polynucleotide is an mRNA encoding the fusion molecule (or component thereof), following delivery of the mRNA to the cell, the mRNA is translated, thus generating the fusion molecule.

In other aspects of the invention are provided methods and compositions for increasing engineered nuclease specificity. In one aspect, methods are provided for increasing overall on-target cleavage specificity by decreasing off-target cleavage activity. In some embodiments, the component engineered cleavage half-domain-containing partners of an engineered nuclease complex are used to contact a cell, where each partner of the complex is given in a ratio to the other partner other than one to one. In some embodiments, the ratio of the two partners (half cleavage domains) is given at a 1:2, 1:3, 1:4, 1:5, 1:6, 1:8, 1:9, 1:10 or 1:20 ratio, or any value therebetween. In other embodiments, the ratio of the two partners is greater than 1:30. In other embodiments, the two partners are deployed at a ratio that is chosen to be different from 1:1. In some aspects, each partner is delivered to the cell as an mRNA or is delivered in a viral or non-viral vector where different quantities of mRNA or vector encoding each partner are delivered. In further embodiments, each partner of the nuclease complex may be comprised on a single viral or non-viral vector, but is deliberately expressed such that one partner is expressed at a higher or lower value that the other, ultimately delivering the cell a ratio of cleavage half domains that is other than one to one. In some embodiments, each cleavage half domain is expressed using different promoters with different expression efficiencies. In other embodiments, the two cleavage domains are delivered to the cell using a viral or non-viral vector where both are expressed from the same open reading frame, but the genes encoding the two partners are separated by a sequence (e.g. self-cleaving 2A sequence or IRES) that results in the 3' partner being expressed at a lower rate, such that the ratios of the two partners are 1:2, 1:3, 1:4, 1:5, 1:6, 1:8, 1:9, 1:10 or 1:20 ratio, or any value therebetween. In other embodiments, the two partners are deployed at a ratio that is chosen to be different from 1:1.

Accordingly, in another aspect, a method for cleaving cellular chromatin in a region of interest can comprise (a) selecting a first sequence in the region of interest; (b) engineering a first DNA-binding molecule to specifically bind to the first sequence; (c) expressing a first fusion molecule in the cell, the first fusion molecule comprising the first DNA-binding molecule (e.g., zinc finger, TALE, sgRNA), and a cleavage domain (or half-domain); and (d) expressing a second fusion protein in the cell, the second fusion molecule comprising a second DNA-binding domain, and a second cleavage domain (or half-domain), wherein at least one of the fusion molecules comprises a linker as described herein, and further wherein the first fusion molecule binds to the first sequence, and the second fusion molecule binds to a second sequence located between 2 and 50 nucleotides from the first sequence, such that an active nuclease complex can form and cellular chromatin is cleaved in the region of interest. In certain embodiments, both fusion molecules comprise a linker as described herein between the DNA binding domain and the catalytic nuclease domain.

Also provided are methods of altering a region of cellular chromatin (e.g., an endogenous gene), for example to introduce targeted mutations. In certain embodiments, methods of altering cellular chromatin comprise introducing into the cell one or more targeted nucleases to create a double-stranded break in cellular chromatin at a predetermined site, and a donor polynucleotide, having homology to the nucleotide sequence of the cellular chromatin in the region of the break. Cellular DNA repair processes are activated by the presence of the double-stranded break and the donor polynucleotide is used as a template for repair of the break, resulting in the introduction of all or part of the nucleotide sequence of the donor into the cellular chromatin. Thus, a sequence in cellular chromatin can be altered and, in certain embodiments, can be converted into a sequence present in a donor polynucleotide. One or more targets may be altered using the methods and compositions described herein.

Targeted alterations include, but are not limited to, point mutations (i.e., conversion of a single base pair to a different base pair), substitutions (i.e., conversion of a plurality of base pairs to a different sequence of identical length), insertions or one or more base pairs, deletions of one or more base pairs and any combination of the aforementioned sequence alterations. Alterations can also include conversion of base pairs that are part of a coding sequence such that the encoded amino acid is altered.

The donor polynucleotide can be DNA or RNA, can be linear or circular, and can be single-stranded or double-stranded. It can be delivered to the cell as naked nucleic acid, as a complex with one or more delivery agents (e.g., liposomes, nanoparticles, poloxamers) or contained in a viral delivery vehicle, such as, for example, an adenovirus, lentivirus or an Adeno-Associated Virus (AAV). Donor sequences can range in length from 10 to 1,000 nucleotides (or any integral value of nucleotides therebetween) or longer. In some embodiments, the donor comprises a full-length gene flanked by regions of homology with the targeted cleavage site. In some embodiments, the donor lacks homologous regions and is integrated into a target locus through homology independent mechanism (i.e. NHEJ). In other embodiments, the donor comprises a smaller piece of nucleic acid flanked by homologous regions for use in the cell (i.e. for gene correction). In some embodiments, the donor comprises a gene encoding a functional or structural component such as a shRNA, RNAi, miRNA or the like. In other embodiments, the donor comprises sequences encoding a regulatory element that binds to and/or modulates expression of a gene of interest. In other embodiments, the donor is a regulatory protein of interest (e.g. ZFP TFs, TALE TFs or a CRISPR/Cas TF) that binds to and/or modulates expression of a gene of interest.

In certain of the methods and compositions described herein, the nuclease and donor are delivered using one or more mRNAs and/or AAV vectors. Any dose of mRNA (ng) or AAV vector (vg/dose) can be used. In embodiments in which mRNA is deliver the nuclease(s) and/or optional donor, dosages of mRNA typically range between 10 and 5000 ng/cell or subject (e.g., 2000 ng, 62.5 ng, 31.3 ng, 15.6 ng). In embodiments in which AAV vectors are used to carry the nucleases and/or optional donor, dosages typically range between 1.00E+9 to 1.00E+13 vg/subject or cell for each nuclease (e.g., left and right ZFNs) and the optional donor is given at 1.00E+10 to 1.00E+13. In certain embodiments, each nuclease of a pair is carried on a separate AAV vector and is given at 2.00E+10, 6.00E+10 or 2.00E+11 vg/cell or subject and the donor is carried on another AAV vector and is given at 1.60E+11, 4.8E+11 or 1.6E+12 vg/cell or subject.

For any of the aforementioned methods, the cellular chromatin can be in a chromosome, episome or organellar genome. Cellular chromatin can be present in any type of cell including, but not limited to, prokaryotic and eukaryotic cells, fungal cells, plant cells, animal cells, mammalian cells, primate cells and human cells.

In one aspect, described herein is a zinc finger nuclease comprising first and second (also referred to as left and right or ZFN partners) ZFNs, the first ZFN comprising the ZFN designated 71557 (comprising a ZFP having the recognition helix regions shown in Table 1 for SBS 42875 and having additional features (e.g., mutations in the FokI sequences and ZFP backbone, 5' UTR sequence, etc.) shown in Table 3 and Table 4) and the second ZFN comprising the designated 71728 (comprising a ZFP having the recognition helix regions shown in Table 1 for SBS 47874 and other features (e.g., mutations in the FokI sequences and ZFP backbone, 5' UTR sequence, etc.) shown in Table 3 and Table 5) and/or one or more polynucleotides encoding one or both of the left and right ZFNs. In certain embodiments, the first and second (left and right) ZFNs are encoded by separate polynucleotides, which separate polynucleotides may be of the same or different types (e.g., 2 AAV vectors in which one AAV comprises sequences encoding the left ZFN and one AAV comprises sequences encoding the right ZFN, 2 mRNAs where one mRNA encodes the left ZFN and the other encodes the right ZFN, 1 AAV comprising both ZFNs linked together by a self-cleaving peptide sequence (for example 2A) and 1 mRNA encoding one ZFN used together with one AAV comprising sequences encoding the other ZFN, etc.). In certain embodiments, the vectors are AAV vectors comprising the elements (sequences) as shown in Table 4 and/or Table 5, including the complete AAV sequences designated "71557 AAV" or "SB71557 AAV" (SEQ ID NO:43) and "71728 AAV" or "SB71728 AAV" (SEQ ID NO:56) as shown herein. In other embodiments, one or more of the elements shown in Tables 4 and 5 are replaced with any analogous sequence, for example the WPRE sequence of these Tables may be replaced with WPRE sequences known in the art or set forth herein in Example 4 (e.g., SEQ ID NO:68 or SEQ ID NO:69 or other WPRE sequence in place of SEQ ID NO:53). In some embodiments, many amino acid modifications can be made to the ZFNs. In some embodiments, 3, 6, 9, 10, 11, 12, 13, 14, 15, 16, 17, 18, 19, 20 or more amino acid substitutions are made. In some embodiments, 13 combined amino acid substitutions to six of the fingers on the right and left sides are made.

Thus, described herein is a zinc finger nuclease comprising first and second ZFNs, the first ZFN comprising the ZFN designated 71557 and the second ZFN comprising the ZFN designated 71728. One or more polynucleotides comprising sequences encoding the first and second ZFNs as described herein are also provided. In certain embodiments, a single polynucleotide encodes the first and second ZFNs and in other embodiments, two separate polynucleotides comprise sequences encoding the first and second ZFNs. The one or more polynucleotides encoding the ZFN may be carried on the same or different AAV vectors. In certain embodiments, provided herein are two polynucleotides, the first polynucleotide (e.g., AAV vector) comprising sequences as shown in Table 4 or the sequence as shown in SEQ ID NO:43 and the second polynucleotide (e.g., AAV vector) comprising sequences as shown in Table 5 or the sequence as shown in SEQ ID NO:56. In some embodiments, the AAV comprising the left ZFN (SB-71557) is referred to as SB-A6P-ZL2. In some embodiments, the AAV comprising the right ZFN (SB-71728) is referred to as SB-A6P-ZR2.

In another aspect, described herein is a cell (e.g., stem cell, precursor cell or hepatic cells of a subject) comprising one or more ZFNs and/or polynucleotides (e.g., AAV vectors) as described herein. Any cell or cell line can be used, including but not limited to a stem cell, a precursor cell, a liver cell, a blood cell, or the like. Cells may further include a donor polynucleotide, typically a polynucleotide encoding an exogenous sequence such as a transgene encoding a therapeutic protein or fragment thereof, which exogenous sequence is integrated into the genome of the cell following cleavage of the endogenous albumin gene. The donor may be carried on the same vector as one or both of the ZFN partners or, alternatively, may be administered using a separate vector, which may be the same or different type than the vector(s) carrying one or both of the ZFN partners. In certain embodiments, the cells comprise 3 separate AAV vectors, the first comprising sequences encoding the left ZFN, the second comprising sequences encoding the right ZFN and the third comprising the donor polynucleotide. Daughter cells descended from cells comprising the ZFNs and donor polynucleotide, which daughter cells include genetic modifications made by the ZFNs (e.g., integrated donor polynucleotide), are also described. Such genetic modifications may be identified through standard methods known in the art, including next generation sequencing of the genomic DNA of the daughter cells wherein such sequence results are compared to wildtype cells that have not been treated with the ZFN and donor polynucleotides.

In another aspect, described herein are pharmaceutical compositions comprising one or more ZFNs, one or more polynucleotides (e.g., AAV vectors) and/or one or more cells as described herein. In certain embodiments, the pharmaceutical composition comprises 3 separate AAV vectors: a first AAV comprising ZFN 71557 (e.g., "71557 AAV"); a second AAV comprising ZFN 71728 (e.g., "71728 AAV"); and third AAV comprising a donor polynucleotide.

In another aspect, methods of using one or more of the ZFNs, one or more of the polynucleotides (e.g., AAV vectors), one or more of the cells and/or one or more of the pharmaceutical compositions (e.g., a pharmaceutical composition comprising 3 separate AAV vectors) as described herein for cleaving an endogenous albumin gene, optionally wherein the method (use) further comprises administering a donor polynucleotide comprising an exogenous sequence (e.g., carried by an AAV vector) such that the exogenous sequence is integrated into the cleaved albumin gene in the isolated cell or in a cell of a subject. In some embodiments, such one or more of the ZFNs, one or more of the polynucleotides, one or more of the cells and/or one or more of the pharmaceutical compositions described herein are used to prevent or treat a human disease.

Kits comprising one or more zinc finger nucleases, one or more polynucleotides, one or more cells and/or one or more pharmaceutical compositions as described herein as well as optional instructions for their use are also provided.

In yet another aspect, described herein is a composition (also referred to as a "FIX composition") comprising: (a) a first polynucleotide (e.g., AAV) comprising sequences encoding a first ZFN designated 71557, the first polynucleotide optionally comprising the sequences as shown in Table 4 or the sequence designated SB71557 AAV (SEQ ID NO:43); (b) a second polynucleotide (e.g., AAV) comprising sequences encoding a second ZFN designated 71728, the second polynucleotide optionally comprising sequences as shown in Table 5 or the sequence designated SB71728 AAV (SEQ ID NO:56); and (c) a donor polynucleotide (e.g., AAV) comprising a sequence encoding a Factor IX (FIX) protein. In certain embodiments, the donor comprises the sequences as shown in Table 6, optionally the sequence as shown in SEQ ID NO:59. In any of the FIX compositions described herein, the first, second and donor polynucleotides may be carried on three separate AAV vectors. Methods of using the compositions as described herein for expressing FIX in a subject in need thereof are also provided. In certain embodiments, the composition is administered to the subject such that the ZFN (71557 and 71728) cleaves an endogenous albumin gene in the subject, the FIX sequence is integrated into the cleaved albumin gene and a FIX protein is expressed in the subject. The methods and compositions described herein can be used to treat and/or prevent a hemophilia in a subject in need thereof. Kits comprising one or more of the FIX compositions and optionally instructions for their use are also provided.

In a still further aspect, described herein is a composition (also referred to as "MPS II composition" or "IDS composition") comprising: (a) a first polynucleotide (e.g., AAV) comprising sequences encoding a first ZFN designated 71557, the first polynucleotide optionally comprising the sequences as shown in Table 4 or the sequence designated SB 71557 AAV (SEQ ID NO:43); (b) a second polynucleotide (e.g., AAV) comprising sequences encoding a second ZFN designated 71728, the second polynucleotide optionally comprising sequences as shown in Table 5 or the sequence designated SB 71728 (SEQ ID NO:56); and (c) a donor polynucleotide (e.g., AAV) comprising a sequence encoding an iduronate-2-sulfatase (IDS) sequence. In certain embodiments, the donor comprises the sequences as shown in Table 7, optionally the sequence as shown in SEQ ID NO:65. In any of the MPS II compositions described herein, the first, second and donor polynucleotides may be carried on three separate AAV vectors. Methods of using the compositions as described herein for expressing IDS in a subject in need thereof are also provided. In certain embodiments, the composition is administered to the subject such that the ZFN (71557 and 71728) cleaves an endogenous albumin gene in the subject, the IDS sequence is integrated into the cleaved albumin gene and an IDS protein is expressed in the subject. The methods and compositions described herein can be used to treat and/or prevent MPS II in a subject in need thereof. Kits comprising one or more of the MPS II compositions and optionally instructions for their use are also provided.

In a still further aspect, described herein is a composition (also referred to as "MPS I composition" or "IDUA composition") comprising: (a) a first polynucleotide (e.g., AAV) comprising sequences encoding a first ZFN designated 71557, the first polynucleotide optionally comprising the sequences as shown in Table 4 or the sequence designated SB 71557 AAV (SEQ ID NO:43); (b) a second polynucleotide (e.g., AAV) comprising sequences encoding a second ZFN designated 71728, the second polynucleotide optionally comprising sequences as shown in Table 5 or the sequence designated SB SEQ ID NO:56; and (c) a donor polynucleotide (e.g., AAV) comprising a sequence encoding an alpha-L iduronidase (IDUA) sequence. In certain embodiments, the donor comprises the sequences as shown in Table 8, optionally the sequence as shown in SEQ ID NO:72. In any of the MPS I compositions described herein, the first, second and donor polynucleotides may be carried on three separate AAV vectors. Methods of using the compositions as described herein for expressing IDUA in a subject in need thereof are also provided. In certain embodiments, the composition is administered to the subject such that the ZFN (71557 and 71728) cleaves an endogenous albumin gene in the subject, the IDUA sequence is integrated into the cleaved albumin gene and an IDUA protein is expressed in the subject. The methods and compositions described herein can be used to treat and/or prevent MPS I in a subject in need thereof. Kits comprising one or more of the MPS I compositions and optionally instructions for their use are also provided.

In some embodiments, any of the compositions disclosed herein are administered to the subject in need thereof in a single dose. In other embodiments, the compositions are administered in more than one dose. In some embodiments, the compositions are administered in more than one dose with a time period in between the doses. In some embodiments, the time period comprises 1, 2, 3, 4, 5, or 6 months. In some embodiments, the time period comprises half a year, a year, two years, three years, four years, 5 years or more.

In yet another aspect, cells comprising any of the polypeptides (e.g., fusion molecules) and/or polynucleotides as described herein are also provided. In one embodiment, the cells comprise a pair of fusion molecules, each comprising a cleavage domain as disclosed herein. Cells include cultured cells, cells in an organism and cells that have been removed from an organism for treatment in cases where the cells and/or their descendants will be returned to the organism after treatment. A region of interest in cellular chromatin can be, for example, a genomic sequence or portion thereof.

In another aspect, described herein is a kit comprising a fusion protein as described herein or a polynucleotide encoding one or more zinc finger proteins, cleavage domains and/or fusion proteins as described herein; ancillary reagents; and optionally instructions and suitable containers. The kit may also include one or more nucleases or polynucleotides encoding such nucleases.

These and other aspects will be readily apparent to the skilled artisan in light of disclosure as a whole.

BRIEF DESCRIPTION OF THE DRAWINGS

FIGS. 1A and 1B depict partial sequence of a human albumin genomic sequence (SEQ ID NO:41) and show the binding sites of exemplary ZFNs 47171-FLAG and 47898-FLAG (target sites shown by underline or overline). FIG. 1A also shows (boxed) a single nucleotide polymorphism (SNP) from A/T to G/C that occurs in approximately 20% of individuals. FIG. 1B is a schematic depicting the manner in which the left and right ZFNs associate with the target albumin sequences.

FIGS. 3A through 3H show exemplary results of genomic modifications using ZFN-encoding vectors as described herein. FIG. 3A shows results of modifications (at the intended target (albumin) as compared to modifications of an off-target site (SMCHD1) under the indicated conditions using exemplary artificial nucleases as described herein (modifications indicated in name) as compared to nucleases not including the modifications described herein ("parent"). As shown, the nucleases described herein exhibit increased activity and specificity as compared to the parent nucleases. FIG. 3B shows cleavage activity (% indels as measured by deep sequencing of using the indicated parent or optimized ZFNs at the indicated dosages for the intended target ("albumin—on target") (2000 ng, 62.5 ng, 31.3 ng, 15.6 ng) or for the off-target sites ("off-target") (2000 ng). The engineered FokI domain N159D shown in the Figure is also referred to as N542D and the FokI domain designated P95S is also referred to as P478S. FIG. 3B also shows a schematic of the ZFN expression cassette with the modifications made in the improved versions. FIG. 3C shows results of activity (cleavage activity as shown by % indels and targeted integration designated "capture events") at the indicated on-target site (albumin) and off-target sites (rows 1 to 26) in K562 and HepG2 cells treated with the ZFNs described herein. "ns" refers to not significant; "ns*" refers to indels not consistent with ZFN cleavage; "^" refers to indels consistent with ZFN cleavage and a non-significant p-value; and "ND" refers to no data. FIG. 3D is a graph showing cleavage (% indels) at the indicated dosages of albumin ZFNs carried by AAV vectors and AAV donors carrying an IDS transgene (low=30/240 ZFN/Donor MOI; mid=100/800 ZFN/Donor MOI; and high=300/2400 ZFN/Donor MOI) using parent 47171/47898 ZFN pair ("ZFN Std" the left bars of each condition) or optimized 71557/71728 ZFN pair ("ZFN 2.0" the right bars of each condition). The 71557/71728 ZFN-encoding AAV constructs used in this experiment included the 5' β-globin untranslated region (UTR), 3× FLAG and Woodchuck Hepatitis Virus (WHV) Post-transcriptional Regulatory Element mutant 6 (WPREmut6). FIG. 3E(i) is a graph showing activity of the protein encoded by the donor transgene (IDS) at the indicated dosages of albumin ZFNs carried by AAV vectors and AAV donors carrying an IDS transgene (low=30/240 ZFN/Donor MOI; mid=100/800 ZFN/Donor MOI; and high=300/2400 ZFN/Donor MOI) using parent ("ZFN Std" the left bars of each condition) or optimized ZFNs ("ZFN 2.0" the right bars of each condition). FIG. 3E(ii) is a graph showing IDS activity at the indicated dosages. From left to right under each condition are shown (left to right): standard ZFN at day 5; standard ZFN at day 7; ZFN 2.0 at day 5 and ZFN 2.0 at day 7. FIGS. 3F(i) and 3F(ii) depict the results from a comparison of the 47171/47898 pair and the 71557/47898 pair. The indicated amount of ZFN-encoding mRNA was transfected in triplicate into primary human hepatocytes that are heterozygous for the WT (A:T) and SNP (G:C)-containing ZFN target sites. The 71557 ZFN-encoding mRNA used in this experiment included the 5' β-globin untranslated region (UTR) and Woodchuck Hepatitis Virus (WHV) Post-transcriptional Regulatory Element (WPRE). Levels of ZFN activity were determined 24-hr post-transfection by deep-sequencing. FIG. 3F(i) shows ZFN activity (presented as % indels) at the A:T WT allele (dark gray) and G:C SNP allele (light gray) target site. FIG. 3F(ii) shows the ratio of ZFN activity at the A:T WT allele target site versus the G:C SNP allele target site, where a value of 1.0 indicates equal cutting at each allele (47171/47898 ZFN pair in light gray, 71557/47898 ZFN pair in dark gray). FIG. 3G is a graph depicting the cleavage kinetics in primary human hepatocytes of the 47171/47898 and 71557/71728 ZFN pairs, wherein the ZFNs were delivered to the cells by AAV. The 71557/71728 ZFN-encoding AAV constructs used in this experiment included the 5' β-globin untranslated region (UTR), 3× FLAG and Woodchuck Hepatitis Virus (WHV) Post-transcriptional Regulatory Element mutant 6 (WPREmut6). FIG. 3H shows a comparison of on-target and off-target cleavage data for the 47171/47898 and 71557/71728 ZFN pairs in primary human hepatocytes. The 71557/71728 ZFN-encoding AAV constructs used in this experiment included the 5' β-globin untranslated region (UTR), 3× FLAG and Woodchuck Hepatitis Virus (WHV) Post-transcriptional Regulatory Element mutant 6 (WPREmut6). The top row shows activity of the 71557/71728 ZFN pair on the albumin locus and the SMCHD1 locus at MOI concentrations from 3K to 600K. Also indicated on the left graph at the top is the expected clinical dose range. Human primary hepatocytes transduced with AAV2/6 encoding second generation ZFNs were evaluated by MiSeq deep sequencing. NS—not statistically significant by two tailed t-test, * –p-value<0.05 by two tailed t-test. The bottom row shows a blow up of the 100 K and 600K MOI doses for both the first and second generation ZFN pair against the albumin locus compared with a separate experiment against the SMCHD1 locus. At the 100K MOI dose, the first generation ZFNs showed mean on-target activity of 17% indels and off-target activity of 0.11% indels and second generation ZFNs showed mean on-target activity of 35% and off-target activity of 0.08%. Comparing the two on-target to off-target ratios, second generation ZFNs are ~2.8-fold more selective than first generation ZFNs. At the 600K MOI dose, the first generation ZFNs showed mean on-target activity of 25% indels and off-target activity of 0.36% indels; and second generation ZFNs showed mean on-target activity of 44% and off-target activity of 0.34%. Comparing the two ratios, second generation ZFNs are ~1.9-fold more selective than first generation ZFNs. At the 100K and 600K MOI, % indels for the 47171/47898 and 71557/71728 ZFN pairs are 17% and 35%, and 25% and 44%, respectively, suggesting that the 71557/71728 ZFN pair is ~2-fold more potent than the 47171/47898 ZFN pair.

FIG. 4A is a graph showing activity (% indels) following introduction of polynucleotides encoding the artificial nuclease with (y-axis) or without (x-axis) a 3× FLAG sequence. Data points to the left of the diagonal line indicate where 3× FLAG was beneficial to nuclease activity as compared to data points to the right of the line which indicate where 3× FLAG sequences were detrimental. FIG. 4B shows the increased activity averaged over 4-fold as compared to polynucleotides without FLAG sequences. FIG. 4C is a graph showing nuclease activity (% indels, as determined by deep sequencing) in K562 cells transfected at the indicated mRNA amounts with mRNA encoding albumin-targeting ZFNs with (light shaded circles shown as "+Peptide") or without (dark shaded circles shown as "No Peptide") a FLAG peptide. Cells were assessed for ZFN activity 24 hours after transfection. The numbers above the light shaded circles (mRNA including the 5' peptide) indicate the fold increase as compared to mRNA without the 5' peptide.

FIG. 5A shows increased cleavage activity in isolated cells when the polynucleotide (mRNA) encoding the artificial nuclease included a WPRE in the 3' UTR. FIG. 5B showed increased activity using WPRE-including ZFNs in vivo (in mouse liver) following administration of the indicated mRNAs (using LNPs) to the mouse. FIG. 5B showed increased cleavage activity using WPRE-including ZFNs in vivo (in mouse liver) following administration of the indicated AAVs to the mouse.

FIG. 7A depicts V1 is the initial expression architecture and V2-V8 depict the various variant architecture. Abbreviations are as follows: "ApoE" is the Apo E enhancer; "hAAT" is the human-α1 anti-trypsin promoter; "HBB-IGG" is the human beta chimeric intron comprising the 5' donor site from the first intron of the human β-globin gene and the branch and 3' acceptor site from the intron of an immunoglobulin gene heavy chain variable region; "NLS" is the nuclear localization sequence; "polyA" is the poly A sequence; "WPRE" is the woodchuck hepatitis virus post-transcriptional regulator element; "3× FLAG" is the peptide described as SEQ ID NO:4 and/or SEQ ID NO: 71; and "β-glb" is the 5' untranslated region of the Xenopus beta-globin gene. FIG. 7B shows schematics of the AAVs comprising sequences encoding ZFNs 47171, 47898, 71557 and 71728.

FIGS. 10A through 10C are graphs showing cutting efficiency and ZFN expression in vivo or in vitro. FIG. 10A is a graph showing in vivo cleavage as determined by % indels in mouse liver cells 56 days post injection of the indicated ZFN constructs and FIG. 10B shows ZFN expression levels. Wild type male mice were intravenously injected with albumin ZFN-encoding AAV6 constructs without ("ZFN standard") or with the 5'UTR, FLAG peptide and WPRE sequences ("ZFN improved" or "ZFP 2.0") and IDS donor in three doses: 2.0E+11 vg/mouse (low dose), 6.0E+11 vg/mouse (mid dose) and or 2.0E+12 vg/mouse (high mouse). Liver samples were collected 56 days post injection. From left to right, shown are indels following administration of formulation buffer, low dose unmodified (standard) ZFN-encoding vectors, low dose AAV ZFN-encoding vectors modified as described herein, unmodified (standard) mid dose, mid dose AAV ZFN-encoding vectors ZFNs modified as described herein, unmodified (standard) high dose, and high dose AAV ZFN-encoding vectors ZFNs modified as described herein. As shown, AAV vectors including the modifications described herein (5'UTR, 5' peptide, WPRE) provided a 7-fold increase in cleavage efficiency as compared to unmodified AAV vectors. * –p<0.05, ** –p<0.01 by two tailed Student's t-test. FIG. 10C demonstrates the increased expression of the FIX donor using the 71557/71728 or the 47171/47898 ZFN pair. The ZFN pairs were used to treat HepG2 cells on day 1, and then one day 2, the FIX transgene was used. On day 9, the media was subject to ELISA to determine the amount of FIX protein expressed. The data demonstrates that the use of the 71557/71728 ZFN pair resulted in nearly 3 times more FIX being expressed in the media as compared to the 47171/47898 pair.

FIG. 11A is a graphical depiction of the three donors showing the elements and transgenes comprised by the donor AAVs. FIG. 11B shows the results of the modifications for editing on primary human hepatocytes (left graph) and the increased activity detected in the supernatant of the hepatocytes that have been subject to ZFN-driven targeted integration using the standard ("Current" shown as left bar under indicated dose) ZFN pair as compared with the improved ZFNs ("ZFN 2.0" shown as right bar under indicated dose). FIG. 11C is a graph showing in vivo transgene expression (IDS) of the mouse subjects treated as described in FIG. 10 and Example 7. Wild type male mice were intravenously injected with albumin ZFN-encoding AAV6 constructs without ("ZFN standard") or with the 5'UTR, FLAG peptide and WPRE sequences ("ZFN improved") and IDS donor in three doses: 2.0E+11 vg/mouse (low dose), 6.0E+11 vg/mouse (mid dose) and or 2.0E+12 vg/mouse (high mouse). Liver samples were collected 56 days post injection and relative transgene expression measured as described in the Examples. From left to right, shown are results following administration of formulation buffer, low dose unmodified (standard) ZFN-encoding vectors, low dose AAV ZFN-encoding vectors modified as described herein, unmodified (standard) mid dose, mid dose AAV ZFN-encoding vectors ZFNs modified as described herein, unmodified (standard) high dose, and high dose AAV ZFN-encoding vectors ZFNs modified as described herein. As shown, AAV vectors including the modifications described herein (5'UTR, 5' peptide, WPRE) provided an 18-fold increase in donor (IDS) expression as compared to unmodified AAV vectors.

FIGS. 14A and 14B depict insertion of the IDUA donor in HepG2 cells using the standard 47171/47898 ZFN pair or the 71557/71728 ZFN pair. FIG. 14A depicts IDUA activity over time in the supernatant of HepG2 cells treated with the ZFNs and donor. ZFN dose was at an MOI of 600K and donor was at a dose of 1200K MOI. FIG. 14B depicts the percent indels for each testing condition in the cells. The data demonstrate that both pairs of ZFNs are active and cause ZFN-directed targeted integration of the IDUA transgene.

DETAILED DESCRIPTION

Figure 2:
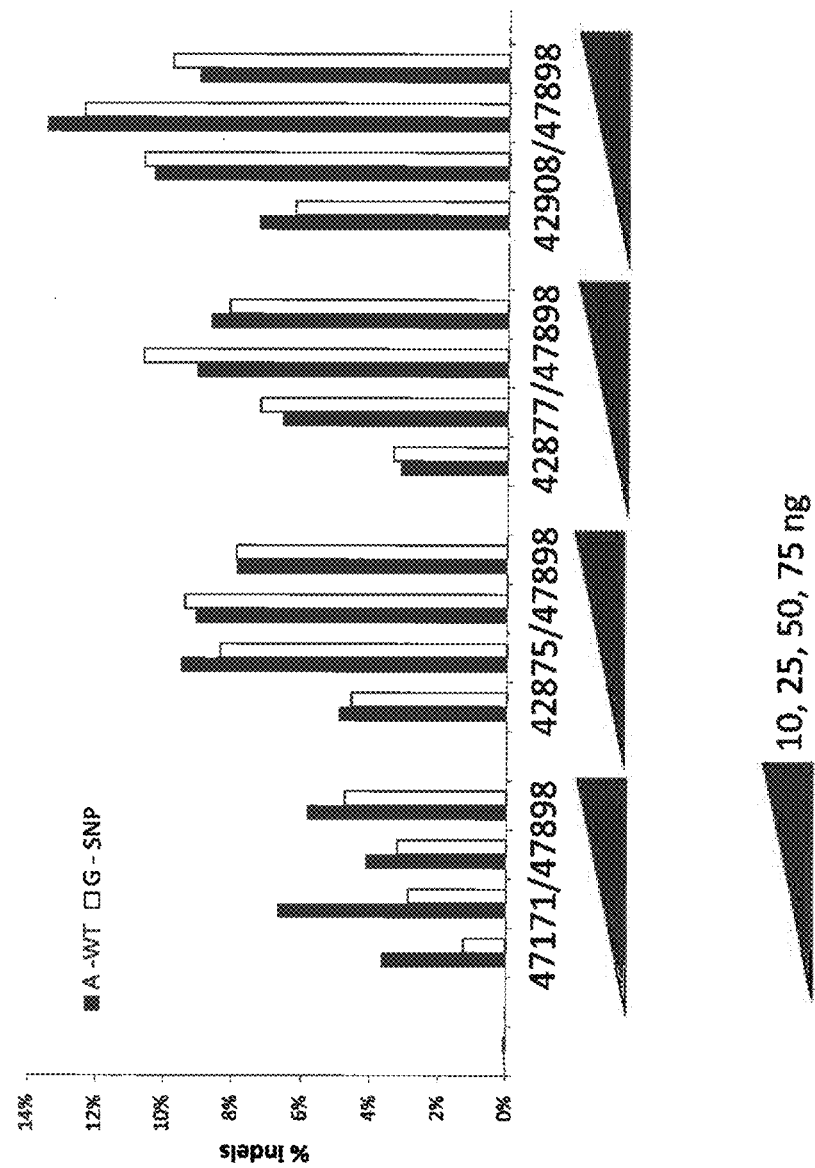
FIG. 2 is a graph showing genomic modifications (% indels) by the indicated exemplary nucleases and the indicated doses. The left bar under each condition shows modification of the wild-type A/T sequence and the right bar shows modification of the G/C SNP.

Disclosed herein are methods and compositions for increasing the efficiency (cleavage activity) of expression of an engineered nuclease, as well as increasing the specificity of on-target engineered nuclease cleavage activity. The methods involve optimizing the combination of expression elements in the nuclease expression vector and decreasing the non-specific interactions between the FokI cleavage domain and DNA and decreasing non-specific interactions between the zinc finger backbone and DNA. Further, the methods and compositions of the invention provide optimized ZFN reagents capable of cleaving a human albumin locus with high specificity, and the optimized albumin reagents are also capable of cleaving a wildtype albumin target sequence and the same target sequence comprising a SNP. The ZFN reagents described herein can be used for efficient and highly targeted cleavage of an albumin gene, including for nuclease-mediated integration of one or more therapeutic protein-encoding sequences (e.g., proteins lacking or deficient in a subject with a disease or disorder) into the cleaved albumin gene such the protein(s) are expressed in the subject and reduce, prevent, and/or treat (e.g., alleviate the symptoms) of the disease or disorder in the subject.

Hemophilia B is an X-linked recessive bleeding disorder caused by mutations in the gene encoding blood coagulation Factor IX (FIX). It is also known as Christmas disease and is the second most common form of hemophilia, after Hemophilia A or Factor VIII deficiency. It occurs in about one in 25,000 males with a prevalence of approximately 4,000 in the United States. The disease manifestation varies depending upon the level of Factor IX clotting activity. The majority of subjects with hemophilia B have a severe form of the disease (<1% FIX activity). They are usually diagnosed during the first two years of life after developing spontaneous joint or deep muscle bleeding. Those with moderate disease (1-5% FIX activity) present with prolonged or delayed bleeding after relatively minor trauma and are diagnosed before age six. By comparison, mild hemophiliacs (>5-30% FIX activity) are diagnosed later in life and do not suffer from spontaneous bleeding but will develop excessive bleeding following surgery or tooth extraction. Finally, approximately 10% of female carriers have FIX activity below 30% and are at risk of excessive bleeding after major trauma or surgery.

The current treatment of hemophilia B consists of the use of FIX concentrates, which were initially derived from donor plasma in the late 1960s. Subsequent improvements such as viral inactivation and donor screening led to more purified concentrates which culminated with the introduction of recombinant FIX in 1997. More recently, a recombinant FIX Fc fusion protein allowing for weekly or biweekly administration was approved for marketing in the United States. Increasing the levels of Factor IX to ~5% of normal (i.e. ~250 ng/mL) results in a profound improvement in symptoms and is sufficient to prevent spontaneous and life-threatening bleeding episodes. (Scriver, C R et al. *The Metabolic and Molecular Bases of Inherited Disease.* New York: McGraw-Hill (2001); Lofqvist, T et al. (1997) *J. Intern. Med.* 241(5): 395-400; Ljung, R C. (1998) *Br. J. Haematol.* 101(2): 215-219). These therapeutic advances have increased the median life expectancy from 11 years prior to the introduction of plasma derived FIX to 63 years with the recombinant protein (Darby, S C et al. (2007) *Blood.* 110(3): 815-25).

Current treatments for hemophilia B rely on chronic, repeated intravenous infusions of purified recombinant Factor IX and suffer from a number of drawbacks. This includes the need for repeated intravenous infusions, which is associated with inhibitor formation, and is prophylactic rather than curative. An alternative approach to clotting factor delivery, based on synthesis from a therapeutic transgene in situ (within the liver of the subject) offers the prospect of eliminating these concerns. The methods and compositions disclosed herein describe treating hemophilia B via a novel strategy that places a corrective FIX transgene into the genome, and under the control of the subject's own endogenous albumin locus or a highly expressed exogenous promoter, thus resulting in liver-specific synthesis of Factor IX. In particular, engineered zinc finger nucleases (ZFNs) as described herein are employed to site-specifically integrate a FIX transgene into the genome of the subject's own hepatocytes in vivo. Integration of the FIX transgene using nucleases as described herein results in stable, high level, liver-specific expression and secretion of FIX into the blood of the subject.

Mucopolysaccharidosis type I (MPS I), also referred to as Hurler/Hurler-Scheie/Scheie syndrome, is a recessive lysosomal storage disorder. According to the National Institute of Neurological Disorders and Stroke (NINDS) factsheet for MPS I, the estimated incidence is 1 in about 100,000 births for severe MPS I, 1 in about 500,000 births for attenuated MPS I, and 1 in about 115,000 births for disease that falls between severe and attenuated.

MPS I is associated with mutations in the gene encoding the iduronidase (IDUA) enzyme, which degrades glycosaminoglycans (sulfated carbohydrate polymers; GAGs). Mutations in the IDUA gene diminish or eliminate IDUA enzyme activity, which results in the accumulation of toxic GAGs in urine, plasma, and body tissues.

Depending upon the specific type of IDUA mutation (more than 100 different mutations have been described) and the levels of the resulting residual IDUA enzyme, patients will develop either Hurler syndrome (MPS I H) or the attenuated variants (MPS I H/S and MPS I S). It has been estimated that 50%-80% of all MPS I patients present with the severe form, which could be partly attributed to the relative ease of diagnosis (Muenzer et al. (2009) *Pediatrics.* 123(1): 19-29). MPS I H patients show symptoms of developmental delay before the end of their first year as well as halted growth and progressive mental decline between ages 2-4 yrs. Other symptoms include organomegaly, corneal clouding, joint stiffness and skeletal deformities (including abnormal spinal bones), coarse facial features with enlarged tongue, hearing loss and hernias. The life expectancy of these MPS I H patients is less than 10 years. Patients with the attenuated form share most of these clinical manifestations but with less severe symptoms. In addition, there is no CNS involvement and therefore they do not suffer from mental retardation.

Many of these patients can survive into adulthood but with significant morbidity. Current therapies for MPS I include hematopoietic stem cell transplant (HSCT) and enzyme replacement therapy (ERT). If patients suffering from the severe MPS I form (MPS I-H) can be diagnosed early (<2.5 yr), therapeutic intervention by HSCT (bone marrow or umbilical cord stems cells) can prevent or reverse most clinical features including neurocognition. Currently, almost all patients with MPS I H undergo HSCT. For MPS I the mortality rate after HSCT is 15% and survival rate with successful engraftment is 56% ERT with a polymorphic recombinant protein produced in Chinese Hamster Ovary cells, Aldurazyme®, has been in use since 2003. This enzyme has been shown to improve pulmonary function, hepatosplenomegaly, and exercise capacity and leads to improved health related quality of life. ERT should be instituted as early as possible. Limitations to enzyme replacement therapy includes the need for life-long treatment, development of neutralizing antibodies, inability to cross the blood brain barrier, continued cardiac, orthopedic, ocular complications and the inconvenience of weekly intravenous infusions. Together, these limitations underscore the urgent need to develop a broader array of curative therapies for MPS I.

The objective and rationale for the use of the methods and compositions disclosed herein is to abrogate or decrease the need for enzyme replacement therapy by in vivo genome editing. In particular, engineered zinc finger nucleases (ZFNs) as described herein are employed to site-specifically integrate a corrective copy of the iduronidase enzyme (hIDUA) transgene into the genome of the subject's own hepatocytes in vivo. Integration of the hIDUA transgene may be targeted to intron 1 of the albumin locus, resulting in stable, high level, liver-specific expression and secretion of iduronidase into the blood. Placement of the huIDUA transgene under the control of the highly expressed endogenous albumin locus is expected to provide permanent, liver-specific expression of iduronidase for the lifetime of an MPS I patient.

Mucopolysaccharidosis II (MPS II), also referred to as Hunter syndrome, is an X-linked, recessive, lysosomal storage disorder predominantly in males. The incidence of MPS II is reported as 0.3 to 0.71 per 100,000 live births (Burton & Giugliani (2012) *Eur J Pediatr* 171(4):631-9. doi: 10.1007/s00431-012-1703-y. Epub 2012 Mar. 1.). Applying the more conservative median life expectancy of 21.7 years for the attenuated form of the disease (the life expectancy for the severe form of the disease is 11.8 years) (Burrow & Leslie (2008) *Biologics.* 2008 June; 2(2):311-20; Young & Harper (1982) *J Med Genet.* 19(6):408-11) to the yearly incidence yields an estimated prevalence of about 629 individuals with MPS II currently living in the US.

MPS II is caused by mutations in the iduronate-2-sulfatase (IDS) gene which encodes an enzyme involved in the lysosomal degradation of the mucopolysaccharides glycosaminoglycans (GAG). This results in the accumulation of GAG in the urine, plasma and tissues and causes multisystemic, progressive disease. Hunter syndrome represents a disease spectrum spanning early onset, severe disease (two-thirds of patients) with somatic and cognitive involvement, to attenuated MPS II characterized by later onset of somatic disease and little or no central nervous system (CNS) disease. The specific type of IDS mutation (>150 gene mutations have been identified) and the levels of the resulting residual IDS enzyme most likely determine the severity of disease. The residual IDS activity in the attenuated form has been measured at 0.2-2.4% of the wildtype IDS activity and those with the severe phenotype have no activity (Sukegawa-Hayasaka et al. (2006) *J Inherit Metab Dis* 29(6): 755-61). The IDS gene is mapped to Xq28, and contains nine exons spread over 24 kb. Major deletions and rearrangements are always associated with the severe form of the disease.

Severe MPS II patients typically start to have delayed speech and developmental delay between 18 months to 3 years of age. The disease is characterized in severe MPS II patients by organomegaly, hyperactivity and aggressiveness, neurologic deterioration, joint stiffness and skeletal deformities (including abnormal spinal bones), coarse facial features with enlarged tongue, heart valve thickening, hearing loss and hernias. The life expectancy of untreated patients with severe Hunter syndrome is into the mid teenage years with death due to neurologic deterioration and/or cardiorespiratory failure. Patients with the attenuated form are typically diagnosed later than the severe patients. The somatic clinical features are similar to the severe patients, but overall disease severity in milder with, in general, slower disease progression with no or only mild cognitive impairment. Death in the untreated attenuated form is often between the ages of 20-30 years from cardiac and respiratory disease.

The only approved therapy for MPS II is enzyme replacement therapy (ERT). Intravenous (IV) ERT with recombinant IDS protein (idursulfase; Elaprase®) has been approved since 2006. ERT using idursulfase has been shown to improve hepatosplenomegaly, pulmonary function (FVC) and exercise capacity (6 minute walk) and leads to improved health related quality of life. Response to ERT depends on the subject's disease severity at the time of initiation of treatment. Limitations to ERT include the need for life-long treatment, development of neutralizing antibodies, inability of the enzyme to cross the blood brain barrier, and the inconvenience of weekly intravenous infusions. In contrast to Hurler syndrome (the severe form of MPS I), hematopoietic stem cell transplantation (HSCT) is not recommended for the severe form of MPS II. Together, these limitations underscore the urgent need to develop a broader array of curative therapies for MPS II.

Thus, the methods and compositions disclosed herein abrogate or decrease the need for enzyme replacement therapy by in vivo genome editing in subjects with MPS II. In particularly, engineered zinc finger nucleases (ZFNs) as described herein are used to site-specifically integrate a corrective copy of the enzyme iduronate-2-sulfatase (hIDS) transgene into the genome of the subject's own hepatocytes in vivo. Integration of the hIDS transgene is targeted to intron 1 of the albumin locus, resulting in stable, high level, liver-specific expression and secretion of iduronate-2-sulfatase into the blood. Placement of the hIDS transgene under the control of the highly expressed endogenous albumin locus is expected to provide permanent, liver-specific expression of iduronate-2-sulfatase for the lifetime of an MPS II patient.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6} M^{-1}$ or lower. "Affinity" refers to the strength of binding: increased binding affinity being correlated with a lower $K_d$. "Non-specific binding" refers to, non-covalent interactions that occur between any molecule of interest (e.g. an engineered nuclease) and a macromolecule (e.g. DNA) that are not dependent on-target sequence.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity. In the case of an RNA-guided nuclease system, the RNA guide is heterologous to the nuclease component (Cas9 or Cfp1) and both may be engineered.

A "DNA binding molecule" is a molecule that can bind to DNA. Such DNA binding molecule can be a polypeptide, a domain of a protein, a domain within a larger protein or a polynucleotide. In some embodiments, the polynucleotide is DNA, while in other embodiments, the polynucleotide is RNA. In some embodiments, the DNA binding molecule is a protein domain of a nuclease (e.g. the FokI domain), while in other embodiments, the DNA binding molecule is a guide RNA component of an RNA-guided nuclease (e.g. Cas9 or Cfp1).

A "DNA binding protein" (or binding domain) is a protein, or a domain within a larger protein, that binds DNA in a sequence-specific manner, for example through one or more zinc fingers or through interaction with one or more RVDs in a zinc finger protein or TALE, respectively. The term zinc finger DNA binding protein is often abbreviated as zinc finger protein or ZFP.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Artificial nucleases and transcription factors can include a ZFP DNA-binding domain and a functional domain (nuclease domain for a ZFN or transcriptional regulatory domain for ZFP-TF). The term "zinc finger nuclease" includes one ZFN as well as a pair of ZFNs (the members of the pair are referred to as "left and right" or "first and second" or "pair") that dimerize to cleave the target gene.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. Nos. 8,586,526 and 9,458,205. Artificial nucleases and transcription factors can include a TALE DNA-binding domain and a functional domain (nuclease domain for a TALEN or transcriptional regulatory domain for TALEN-TF). The term "TALEN" includes one TALEN as well as a pair of TALENs (the members of the pair are referred to as "left and right" or "first and second" or "pair") that dimerize to cleave the target gene.

Zinc finger and TALE DNA-binding domains can be "engineered" to bind to a predetermined nucleotide sequence, for example via engineering (altering one or more amino acids) of the recognition helix region of a naturally occurring zinc finger protein or by engineering of the amino acids involved in DNA binding (the "repeat variable diresidue" or RVD region). Therefore, engineered zinc finger proteins or TALE proteins are proteins that are non-naturally occurring. Non-limiting examples of methods for engineering zinc finger proteins and TALEs are design and selection. A designed protein is a protein not occurring in nature whose design/composition results principally from rational criteria. Rational criteria for design include application of substitution rules and computerized algorithms for processing information in a database storing information of existing ZFP or TALE designs and binding data. See, for example, U.S. Pat. Nos. 8,586,526; 6,140,081; 6,453,242; and 6,534,261; see also WO 98/53058; WO 98/53059; WO 98/53060; WO 02/016536 and WO 03/016496.

A "selected" zinc finger protein, TALE protein or CRISPR/Cas system is not found in nature whose production results primarily from an empirical process such as phage display, interaction trap, rational design or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970; WO 01/88197 and WO 02/099084.

"TtAgo" is a prokaryotic Argonaute protein thought to be involved in gene silencing. TtAgo is derived from the bacteria Thermus thermophilus. See, e.g. Swarts et al, ibid; G. Sheng et al., (2013) *Proc. Natl. Acad. Sci. U.S.A.* 111, 652). A "TtAgo system" is all the components required including e.g. guide DNAs for cleavage by a TtAgo enzyme.

"Recombination" refers to a process of exchange of genetic information between two polynucleotides, including but not limited to, capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In certain methods of the disclosure, one or more targeted nucleases as described herein create a double-stranded break (DSB) in the target sequence (e.g., cellular chromatin) at a predetermined site (e.g., a gene or locus of interest). The DSB mediates integration of a construct (e.g. donor) as described herein. Optionally, the construct has homology to the nucleotide sequence in the region of the break. An expression construct may be physically integrated or, alternatively, the expression cassette is used as a template for repair of the break via homologous recombination, resulting in the introduction of all or part of the nucleotide sequence as in the expression cassette into the cellular chromatin. Thus, a first sequence in cellular chromatin can be altered and, in certain embodiments, can be converted into a sequence present in an expression cassette. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional engineered nucleases can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence or via cleavage of the target sequence(s) followed by error-prone NHEJ-mediated repair that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miR-NAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize. The term "cleavage domain" is used interchangeably with the term "cleavage half-domain." The term "FokI cleavage domain" includes the FokI sequence as shown in SEQ ID NO:2 as well as any FokI homologues.

An "engineered cleavage half-domain" is a cleavage half-domain that has been modified so as to form obligate heterodimers with another cleavage half-domain (e.g., another engineered cleavage half-domain).

The term "sequence" refers to a nucleotide sequence of any length, which can be DNA or RNA; can be linear, circular or branched and can be either single-stranded or double stranded. The term "transgene" refers to a nucleotide sequence that is inserted into a genome. A transgene can be of any length, for example between 2 and 100,000,000 nucleotides in length (or any integer value therebetween or thereabove), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween).

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids, minicircles and certain viral genomes. The liver specific constructs described herein may be episomally maintained or, alternatively, may be stably integrated into the cell.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, ligases, deubiquitinases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster. Methods for the introduction of exogenous molecules into plant cells are known to those of skill in the art and include, but are not limited to, protoplast transformation, silicon carbide (e.g., WHISKERS™) *Agrobacterium*-mediated transformation, lipid-mediated transfer (i.e., liposomes, including neutral and cationic lipids), electroporation, direct injection, cell fusion, particle bombardment (e.g., using a "gene gun"), calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of fusion molecules include, but are not limited to, fusion proteins (for example, a fusion between a protein DNA-binding domain and a cleavage domain such as a ZFN or TALEN), fusions between a polynucleotide DNA-binding domain (e.g., sgRNA) operatively associated with a cleavage domain, and fusion nucleic acids (for example, a nucleic acid encoding the fusion protein).

Expression of a fusion molecule in a cell can result from delivery of the components of the fusion molecule to the cell or by delivery of one or more polynucleotide encoding one or more components of the fusion molecule to a cell, wherein the necessary polynucleotide is transcribed, and the transcript is translated, to generate the fusion molecule. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP, TALE or CRISPR/Cas system as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

A "safe harbor" locus is a locus within the genome wherein a gene may be inserted without any deleterious effects on the host cell. Most beneficial is a safe harbor locus in which expression of the inserted gene sequence is not perturbed by any read-through expression from neighboring genes. Non-limiting examples of safe harbor loci that are targeted by nuclease(s) include CCR5, HPRT, AAVS1, Rosa and albumin. See, e.g., U.S. Pat. Nos. 7,951,925; 8,771,985; 8,110,379; 7,951,925; U.S. Publication Nos. 20100218264; 20110265198; 20130137104; 20130122591; 20130177983; 20130177960; 20150056705 and 20150159172.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

A "WPRE" sequence is a woodchuck hepatitis posttranscriptional regulatory element derived from the woodchuck hepatitis virus. WPRE is a 600 bp long tripartite element containing gamma, alpha, and beta elements, in the given order (Donello et al (1992) *J Virol* 72:5085-5092) and contributes to the strong expression of transgenes in AAV systems (Loeb et al (1999) *Hum Gene Ther* 10:2295-2305). It also enhances the expression of a transgene lacking introns. In its natural form WPRE contains a partial open reading frame (ORF) for the WHV-X protein. The fully expressed WHV-X protein in the context of other viral elements like the WHV (We2) enhancer has been associated with a higher risk of hepatocarcinoma in woodchucks and mice (Hohne et. al (1990) *EMBO J* 9(4):1137-45; Flajolet et. al (1998) *J Virol* 72(7):6175-80). The WHV-X protein does not appear to be directly oncogenic, but some studies suggest that under certain circumstances it can act as a weak cofactor for the generation of liver cancers associated with infection by hepadnaviruses (hepatitis B virus for man; woodchuck hepatitis virus for woodchucks). Many times, mention of "wildtype" WPRE is referring to a 591 bp sequence (nucleotides 1094-1684 in GenBank accession number J02442) containing a portion of the WHV X protein open-reading frame (ORF) in its 3' region. In this element, there is an initial ATG start codon for WHV-X at position 1502 and a promoter region with the sequence GCTGA at position 1488. In Zanta-Boussif (ipid), a mut6WPRE sequence was disclosed wherein the promoter sequence at position 1488 was modified to ATCAT and the start codon at position 1502 was modified to TTG, effectively prohibiting expression of WHV-X. In the J04514.1 WPRE variant, the ATG WHV X start site is a position 1504, and a mut6 type variant can be made in the this J04514.1 strain. Another WPRE variant is the 247 bp WPRE3 variant comprising only minimal gamma and alpha elements from the wild type WPRE (Choi et al (2014) *Mol Brain* 7:17), which lacks the WHV X sequences.

"Eukaryotic" cells include, but are not limited to, fungal cells (such as yeast), plant cells, animal cells, mammalian cells and human cells (e.g., T-cells), including stem cells (pluripotent and multipotent).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid or protein (e.g., coding function, ability to hybridize to another nucleic acid, enzymatic activity assays) are well-known in the art.

A polynucleotide "vector" or "construct" is capable of transferring gene sequences to target cells. Typically, "vector construct," "expression vector," "expression construct," "expression cassette," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the expression cassettes of the invention can be administered. Subjects of the present invention include those with a disorder.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Cancer, monogenic diseases and graft versus host disease are non-limiting examples of conditions that may be treated using the compositions and methods described herein.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease. An "intended" or "on-target" sequence is the sequence to which the binding molecule is intended to bind and an "unintended" or "off-target" sequence includes any sequence bound by the binding molecule that is not the intended target.

DNA-Binding Molecules/Domains

Described herein are compositions comprising a DNA-binding molecule/domain that specifically binds to a target site in any gene or locus of interest. Any DNA-binding molecule/domain can be used in the compositions and methods disclosed herein, including but not limited to a zinc finger DNA-binding domain, a TALE DNA binding domain, the DNA-binding portion (guide or sgRNA) of a CRISPR/Cas nuclease, or a DNA-binding domain from a meganuclease.

In certain embodiments, the DNA binding domain comprises a zinc finger protein. Preferably, the zinc finger protein is non-naturally occurring in that it is engineered to bind to a target site of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties. In certain embodiments, the DNA-binding domain comprises a zinc finger protein disclosed in U.S. Patent Publication No. 2012/0060230 (e.g., Table 1), incorporated by reference in its entirety herein.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in U.S. Pat. No. 6,794,136.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in U.S. Pat. No. 6,794,136.

Selection of target sites; ZFPs and methods for design and construction of fusion molecules (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Usually, the ZFPs include at least three fingers. Certain of the ZFPs include four, five or six fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, which domains can be transcriptional activation or repression domains.

In some embodiments, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128.

Figure 5A:
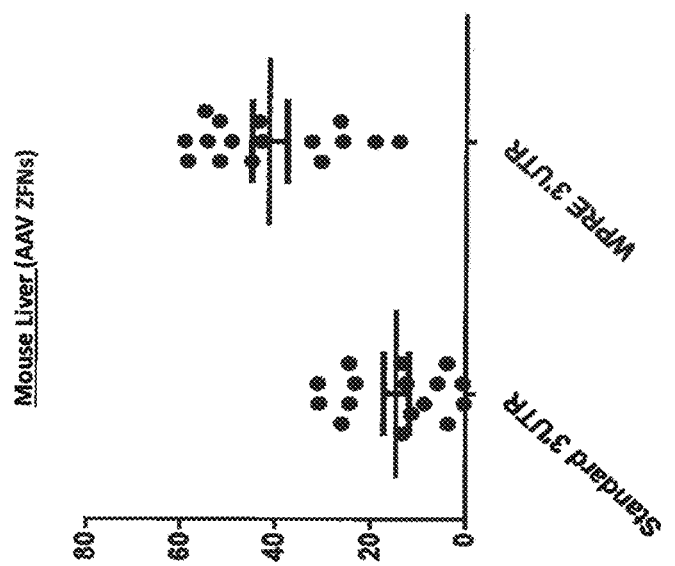
FIGS. 5A through 5C are graphs depicting increased nuclease activity (% indels, as determined by next generation sequencing) when the nucleases are expressed from polynucleotides further comprising modified 3' UTRs (e.g., WPRE sequences) as compared to unmodified 3' UTRs.

In certain embodiments, the zinc finger protein (e.g., used in a fusion molecule with a wild-type or mutant cleavage domain) as described herein comprises one or more mutations (substitutions, deletions, and/or insertions) to the backbone regions (e.g., regions outside the 7-amino acid recognition helix region numbered −1 to 6), for example at one or more of positions −14, −9 and/or −5 (see, e.g., FIG. 5A). The wild-type residue at one or more these positions may be deleted, replaced with any amino acid residue and/or include on or more additional residues. In some embodiments, the Arg (R) at position −5 is changed to a Tyr (Y), Asp (N), Glu (E), Leu (L), Gln (Q), or Ala (A). In other embodiments, the Arg (R) at position (−9) is replaced with Ser (S), Asp (N) or Glu (E). In further embodiments, the Arg (R) at position (−14) is replaced with Ser (S) or Gln (Q). In other embodiments, the fusion polypeptides can comprise mutations in the zinc finger DNA binding domain where the amino acids at the (−5), (−9) and/or (−14) positions are changed to any of the above listed amino acids in any combination.

In certain embodiments, the ZFN comprises first and second (left and right) ZFNs as described in any of the appended Tables or Figures. In certain embodiments, the first ZFN comprises the ZFN designated 71557 and the second ZFN comprises the ZFN designated 71728. In certain embodiments, the ZFN designated 71557 is carried on an AAV vector, for example an AAV vector comprising the sequences shown in Table 4 and/or the sequence as shown in SEQ ID NO:43. In other embodiments, the ZFN designated 71728 is carried on an AAV vector, for example an AAV vector comprising the sequences shown in Table 5 and/or SEQ ID NO:56.

In other embodiments, the DNA binding domain comprises an engineered domain from a Transcriptional Activator-Like (TAL) effector (TALE) similar to those derived from the plant pathogens *Xanthomonas* (see Boch et al, (2009) *Science* 326: 1509-1512 and Moscou and Bogdanove, (2009) *Science* 326: 1501) and Ralstonia (see Heuer et al (2007) *Applied and Environmental Microbiology* 73(13): 4379-4384); U.S. Patent Publication Nos. 20110301073 and 20110145940. The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like effectors (TALE) which mimic plant transcriptional activators and manipulate the plant transcriptome (see Kay et al (2007) *Science* 318:648-651). These proteins contain a DNA binding domain and a transcriptional activation domain. One of the most well characterized TALEs is AvrBs3 from *Xanthomonas campestris* pv. *Vesicatoria* (see Bonas et al (1989) *Mol Gen Genet* 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 base pairs in the repeat domain of hpx17. However, both gene products have less than 40% sequence identity with AvrBs3 family proteins of *Xanthomonas*.

Specificity of these TAL effectors depends on the sequences found in the tandem repeats. The repeated sequence comprises approximately 102 base pairs and the repeats are typically 91-100% homologous with each other (Bonas et al, ibid). Polymorphism of the repeats is usually located at positions 12 and 13 and there appears to be a one-to-one correspondence between the identity of the hypervariable diresidues (the repeat variable diresidue or RVD region) at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the natural code for DNA recognition of these TAL-effectors has been determined such that an HD sequence at positions 12 and 13 (Repeat Variable Diresidue or RVD) leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN), including TALENs with atypical RVDs. See, e.g., U.S. Pat. No. 8,586,526.

In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al., (2013) Nucl Acid Res: 1-13, doi: 10.1093/nar/gkt1224).

In still further embodiments, the nuclease comprises a compact TALEN. These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et al (2013) Nat Comm: 1-8 DOI: 10.1038/ncomms2782). In addition, the nuclease domain may also exhibit DNA-binding functionality. Any TALENs may be used in combination with additional TALENs (e.g., one or more TALENs (cTALENs or FokI-TALENs) with one or more mega-TALEs.

In addition, as disclosed in these and other references, zinc finger domains and/or multi-fingered zinc finger proteins or TALEs may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in U.S. Pat. No. 6,794,136. In certain embodiments, the DNA-binding domain is part of a CRISPR/Cas nuclease system, including a single guide RNA (sgRNA) DNA binding molecule that binds to DNA. See, e.g., U.S. Pat. No. 8,697,359 and U.S. Patent Publication Nos. 20150056705 and 20150159172. The CRISPR (clustered regularly interspaced short palindromic repeats) locus, which encodes RNA components of the system, and the cas (CRISPR-associated) locus, which encodes proteins (Jansen et al., 2002. Mol. Microbiol. 43: 1565-1575; Makarova et al., 2002. Nucleic Acids Res. 30: 482-496; Makarova et al., 2006. Biol. Direct 1: 7; Haft et al., 2005. PLoS Comput. Biol. 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

In some embodiments, the DNA binding domain is part of a TtAgo system (see Swarts et al, ibid; Sheng et al, ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) Science 344: 972-973). In contrast, prokaryotic Ago proteins bind to small single-stranded DNA fragments and likely function to detect and remove foreign (often viral) DNA (Yuan et al., (2005) Mol. Cell 19, 405; Olovnikov, et al. (2013) Mol. Cell 51, 594; Swarts et al., ibid). Exemplary prokaryotic Ago proteins include those from Aquifex aeolicus, Rhodobacter sphaeroides, and Thermus thermophilus.

One of the most well-characterized prokaryotic Ago protein is the one from T. thermophilus (TtAgo; Swarts et al. ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from Rhodobacter sphaeroides (RsAgo) has similar properties (Olivnikov et al. ibid).

Exogenous guide DNAs of arbitrary DNA sequence can be loaded onto the TtAgo protein (Swarts et al. ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37° C. Ago-RNA-mediated DNA cleavage could be used to affect a panoply of outcomes including gene knock-out, targeted gene addition, gene correction, targeted gene deletion using techniques standard in the art for exploitation of DNA breaks.

Thus, any DNA-binding molecule/domain can be used.

Fusion Molecules

Fusion molecules comprising DNA-binding domains (e.g., ZFPs or TALEs, CRISPR/Cas components such as single guide RNAs) as described herein and a heterologous regulatory (functional) domain (or functional fragment thereof) are also provided. Common domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. U.S. Patent Publication Nos.

20050064474; 20060188987 and 2007/0218528 for details regarding fusions of DNA-binding domains and nuclease cleavage domains, incorporated by reference in their entireties herein.

Suitable domains for achieving activation include the HSV VP16 activation domain (see, e.g., Hagmann et al., *J. Virol.* 71, 5952-5962 (1997)) nuclear hormone receptors (see, e.g., Torchia et al., *Curr. Opin. Cell. Biol.* 10:373-383 (1998)); the p65 subunit of nuclear factor kappa B (Bitko & Barik, *J Virol.* 72:5610-5618 (1998) and Doyle & Hunt, *Neuroreport* 8:2937-2942 (1997)); Liu et al., *Cancer Gene Ther.* 5:3-28 (1998)), or artificial chimeric functional domains such as VP64 (Beerli et al., (1998) *Proc. Natl. Acad. Sci. USA* 95:14623-33), and degron (Molinari et al., (1999) *EMBO J.* 18, 6439-6447). Additional exemplary activation domains include, Oct 1, Oct-2A, Sp1, AP-2, and CTF1 (Seipel et al., *EMBO J.* 11, 4961-4968 (1992) as well as p300, CBP, PCAF, SRC1 PvALF, AtHD2A and ERF-2. See, for example, Robyr et al. (2000) *Mol. Endocrinol.* 14:329-347; Collingwood et al. (1999) *J. Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5,-6,-7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

It will be clear to those of skill in the art that, in the formation of a fusion molecule (or a nucleic acid encoding same) between a DNA-binding domain and a functional domain, either an activation domain or a molecule that interacts with an activation domain is suitable as a functional domain. Essentially any molecule capable of recruiting an activating complex and/or activating activity (such as, for example, histone acetylation) to the target gene is useful as an activating domain of a fusion protein. Insulator domains, localization domains, and chromatin remodeling proteins such as ISWI-containing domains and/or methyl binding domain proteins suitable for use as functional domains in fusion molecules are described, for example, in U.S. Patent Publications 2002/0115215 and 2003/0082552 and in WO 02/44376.

Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion molecules (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp et al. (2000) *Proc. Natl. Acad. Sci. USA* 97:3930-3935. Furthermore, single guide RNAs of the CRISPR/Cas system associate with functional domains to form active transcriptional regulators and nucleases.

In certain embodiments, the target site is present in an accessible region of cellular chromatin. Accessible regions can be determined as described, for example, in U.S. Pat. Nos. 7,217,509 and 7,923,542. If the target site is not present in an accessible region of cellular chromatin, one or more accessible regions can be generated as described in U.S. Pat. Nos. 7,785,792 and 8,071,370. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3) (Cordingley et al. (1987) *Cell* 48:261-270; Pina et al. (1990) *Cell* 60:719-731; and Cirillo et al. (1998) *EMBO J.* 17:244-254).

The target sites for the fusion molecules (e.g., artificial nucleases) as described herein may be 9, 10, 11, 12, 13, 14, 15, 16, 17, 18, 19, 20, 21, 22, 23, 24, 25, 26, 27, 28, 29, 30 or more contiguous or non-contiguous base pairs in length.

The fusion molecule may be formulated with a pharmaceutically acceptable carrier, as is known to those of skill in the art. See, for example, Remington's Pharmaceutical Sciences, 17th ed., 1985; and U.S. Pat. Nos. 6,453,242 and 6,534,261.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

Additional exemplary functional domains are disclosed, for example, in U.S. Pat. Nos. 6,534,261 and 6,933,113.

Functional domains that are regulated by exogenous small molecules or ligands may also be selected. For example, RheoSwitch® technology may be employed wherein a functional domain only assumes its active conformation in the presence of the external RheoChem™ ligand (see for example US 20090136465). Thus, the ZFP may be operably linked to the regulatable functional domain wherein the resultant activity of the ZFP-TF is controlled by the external ligand.

Nucleases

In certain embodiments, the fusion molecules comprise a DNA-binding binding domain and cleavage (nuclease) domain to form an artificial nuclease. As such, gene modification can be achieved using a nuclease, for example an engineered nuclease. Engineered nuclease technology is based on the engineering of naturally occurring DNA-binding proteins. For example, engineering of homing endonucleases with tailored DNA-binding specificities has been described. Chames et al. (2005) *Nucleic Acids Res* 33(20): e178; Arnould et al. (2006) *J. Mol. Biol.* 355:443-458. In addition, engineering of ZFPs has also been described. See, e.g., U.S. Pat. Nos. 6,534,261; 6,607,882; 6,824,978; 6,979, 539; 6,933,113; 7,163,824; and 7,013,219.

In addition, ZFPs and/or TALEs have been fused to nuclease domains to create ZFNs and TALENs—a functional entity that is able to recognize its intended nucleic acid target through its engineered (ZFP or TALE) DNA binding domain and cause the DNA to be cut near the DNA binding site via the nuclease activity. See, e.g., Kim et al. (1996) *Proc Nat'l Acad Sci USA* 93(3):1156-1160. More recently, such nucleases have been used for genome modification in a variety of organisms. See, for example, United States Patent Publications 20030232410; 20050208489; 20050026157; 20050064474; 20060188987; 20060063231; and International Publication WO 07/014275.

Thus, the methods and compositions described herein are broadly applicable and may involve any nuclease of interest. Non-limiting examples of nucleases include meganucleases, TALENs and zinc finger nucleases. The nuclease may comprise heterologous DNA-binding and cleavage domains (e.g., zinc finger nucleases; meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site).

In certain embodiments, the ZFN comprises first and second (left and right) ZFNs as described in any of the appended Tables or Figures. In certain embodiments, the first ZFN comprises the ZFN designated 71557 and the second ZFN comprises the ZFN designated 71728. In certain embodiments, the ZFN designated 71557 is carried on an AAV vector, for example an AAV vector comprising the sequences shown in Table 4 and/or the sequence as shown in SEQ ID NO:43. In other embodiments, the ZFN designated 71728 is carried on an AAV vector, for example an AAV vector comprising the sequences shown in Table 5 and/or SEQ ID NO:56.

In any of the nucleases described herein, the nuclease can comprise an engineered TALE DNA-binding domain and a nuclease domain (e.g., endonuclease and/or meganuclease domain), also referred to as TALENs. Methods and compositions for engineering these TALEN proteins for robust, site specific interaction with the target sequence of the user's choosing have been published (see U.S. Pat. No. 8,586,526). In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al., (2013) *Nucl Acid Res:* 1-13, doi: 10.1093/nar/gkt1224). In addition, the nuclease domain may also exhibit DNA-binding functionality.

In still further embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et al (2013) *Nat Comm:* 1-8 DOI: 10.1038/ ncomms2782). Any TALENs may be used in combination with additional TALENs (e.g., one or more TALENs (cTALENs or FokI-TALENs) with one or more mega-TALs) or other DNA cleavage enzymes.

In certain embodiments, the nuclease comprises a meganuclease (homing endonuclease) or a portion thereof that exhibits cleavage activity. Naturally-occurring meganucleases recognize 15-40 base-pair cleavage sites and are commonly grouped into four families: the LAGLIDADG family ("LAGLIDADG" disclosed as SEQ ID NO: 70), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420, 032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

DNA-binding domains from naturally-occurring meganucleases, primarily from the LAGLIDADG family ("LAGLIDADG" disclosed as SEQ ID NO: 70), have been used to promote site-specific genome modification in plants, yeast, *Drosophila*, mammalian cells and mice, but this approach has been limited to the modification of either homologous genes that conserve the meganuclease recognition sequence (Monet et al. (1999), *Biochem. Biophysics. Res. Common.* 255: 88-93) or to pre-engineered genomes into which a recognition sequence has been introduced (Route et al. (1994), *Mol. Cell. Biol.* 14: 8096-106; Chilton et al. (2003), *Plant Physiology.* 133: 956-65; Puchta et al. (1996), *Proc. Natl. Acad. Sci. USA* 93: 5055-60; Rong et al. (2002), *Genes Dev.* 16: 1568-81; Gouble et al. (2006), *J. Gene Med.* 8(5):616-622). Accordingly, attempts have been made to engineer meganucleases to exhibit novel binding specificity at medically or biotechnologically relevant sites (Porteus et al. (2005), *Nat. Biotechnol.* 23: 967-73; Sussman et al. (2004), *J. Mol. Biol.* 342: 31-41; Epinat et al. (2003), *Nucleic Acids Res.* 31: 2952-62; Chevalier et al. (2002) *Molec. Cell* 10:895-905; Epinat et al. (2003) *Nucleic Acids Res.* 31:2952-2962; Ashworth et al. (2006) *Nature* 441:656- 659; Paques et al. (2007) *Current Gene Therapy* 7:49-66; U.S. Patent Publication Nos. 20070117128; 20060206949; 20060153826; 20060078552; and 20040002092). In addition, naturally-occurring or engineered DNA-binding domains from meganucleases can be operably linked with a cleavage domain from a heterologous nuclease (e.g., FokI) and/or cleavage domains from meganucleases can be operably linked with a heterologous DNA-binding domain (e.g., ZFP or TALE).

In other embodiments, the nuclease is a zinc finger nuclease (ZFN) or TALE DNA binding domain-nuclease fusion (TALEN). ZFNs and TALENs comprise a DNA binding domain (zinc finger protein or TALE DNA binding domain) that has been engineered to bind to a target site in a gene of choice and cleavage domain or a cleavage half-domain (e.g., from a restriction and/or meganuclease as described herein).

As described in detail above, zinc finger binding domains and TALE DNA binding domains can be engineered to bind to a sequence of choice. See, for example, Beerli et al. (2002) *Nature Biotechnol.* 20:135-141; Pabo et al. (2001)

*Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain or TALE protein can have a novel binding specificity, compared to a naturally-occurring protein. Engineering methods include, but are not limited to, rational design and various types of selection. Rational design includes, for example, using databases comprising triplet (or quadruplet) nucleotide sequences and individual zinc finger or TALE amino acid sequences, in which each triplet or quadruplet nucleotide sequence is associated with one or more amino acid sequences of zinc fingers or TALE repeat units which bind the particular triplet or quadruplet sequence. See, for example, U.S. Pat. Nos. 6,453,242 and 6,534,261, incorporated by reference herein in their entireties.

Selection of target sites; and methods for design and construction of fusion molecules (and polynucleotides encoding same) are known to those of skill in the art and described in detail in U.S. Pat. Nos. 7,888,121 and 8,409,861, incorporated by reference in their entireties herein.

In addition, as disclosed in these and other references, zinc finger domains, TALEs and/or multi-fingered zinc finger proteins may be linked together using any suitable linker sequences, including for example, linkers of 5 or more amino acids in length. See, e.g., U.S. Pat. Nos. 6,479,626; 6,903,185; and 7,153,949 for exemplary linker sequences 6 or more amino acids in length. The proteins described herein may include any combination of suitable linkers between the individual zinc fingers of the protein and/or between the DNA-binding domain and the nuclease domain. See, also, U.S. Pat. Nos. 8,772,453 and 9,567,609.

Thus, nucleases such as ZFNs, TALENs and/or meganucleases can comprise any DNA-binding domain and any nuclease (cleavage) domain (cleavage domain, cleavage half-domain). As noted above, the cleavage domain may be heterologous to the DNA-binding domain, for example a zinc finger or TAL-effector DNA-binding domain and a cleavage domain from a nuclease or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., 51 Nuclease; mung bean nuclease; pancreatic DNase I; micrococcal nuclease; yeast HO endonuclease; see also Linn et al. (eds.) Nucleases, Cold Spring Harbor Laboratory Press,1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion molecules are required for cleavage if the fusion molecules comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion molecules are preferably disposed, with respect to each other, such that binding of the two fusion molecules to their respective target sites places the cleavage half-domains in a spatial orientation to each other that allows the cleavage half-domains to form a functional cleavage domain, e.g., by dimerizing. Thus, in certain embodiments, the near edges of the paired target sites are separated by 5-10 nucleotides or by 15-18 nucleotides. However, any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion molecules comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is FokI. This particular enzyme is active as a dimer. Bitinaite et al. (1998) *Proc. Natl. Acad. Sci. USA* 95: 10,570-10,575. Accordingly, for the purposes of the present disclosure, the portion of the FokI enzyme used in the disclosed fusion molecules is considered a cleavage half-domain. Thus, for targeted double-stranded cleavage and/or targeted replacement of cellular sequences using zinc finger-FokI fusions, two fusion molecules, each comprising a FokI cleavage half-domain, can be used to reconstitute a catalytically active cleavage domain. Alternatively, a single polypeptide molecule containing a zinc finger binding domain and two FokI cleavage half-domains can also be used. Parameters for targeted cleavage and targeted sequence alteration using zinc finger-FokI fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises a FokI cleavage domain used to generate the crystal structures 1FOK.pdb and 2FOK.pdb (see Wah et al (1997) *Nature* 388:97-100). The sequence of the full-length FokI is shown below. The cleavage domain used in the nucleases described herein is shown in italics and underlining (positions 384 to 579 of the full-length protein) where the holo protein sequence is described below (SEQ ID NO:2):

(SEQ ID NO: 2)
MVSKIRTFGWVQNPGKFENLKRVVQVFDRNSKVHNEVKNIKIPTLVKES

KIQKELVAIMNQHDLIYTYKELVGTGTSIRSEAPCDAIIQATIADQGNK

KGYIDNWSSDGFLRWAHALGFIEYINKSDSFVITDVGLAYSKSADGSAI

EKEILIEAISSYPPAIRILTLLEDGQHLTKFDLGKNLGFSGESGFTSLP

EGILLDTLANAMPKDKGEIRNNWEGSSDKYARMIGGWLDKLGLVKQGKK

EFIIPTLGKPDNKEFISHAFKITGEGLKVLRRAKGSTKFTRVPKRVYWE

MLATNLTDKEYVRTRRALILEILIKAGSLKIEQIQDNLKKLGFDEVIET

IENDIKGLINTGIFIEIKGRFYQLKDHILQFVIPNRGVTK*QLVKSELEE*

*KKSELRHKLKYVPHEYIELIEIARNSTQDRILEAIKVMEFFMKVYGYRG*

*KHLGGSRKPDGAIYTVGSPIDYGVIVDTKAYSGGYNLPIGQADEAVRYV*

*EENQTRNKHINPNEWWKVYPSSVTEFKFLFVSGHFKGNYKAQLTRLNHI*

*TNCNGAVLSVEELLIGGEMIKAGTLTLEEVRRKFNNGEINF*

Cleavage half domains derived from FokI may comprise a mutation in one or more of amino acid residues as shown in SEQ ID NO:2. Mutations include substitutions (of a wild-type amino acid residue for a different residue, insertions (of one or more amino acid residues) and/or deletions (of one or more amino acid residues). In certain embodiments, one or more of residues 414-426, 443-450, 467-488, 501-502, and/or 521-531 (numbered relative to SEQ ID NO:2) are mutated since these residues are located close to the DNA backbone in a molecular model of a ZFN bound to its target site described in Miller et al. ((2007) Nat Biotechnol 25:778-784 Non-limiting examples of FokI mutants include one or more mutations as described herein U.S. Patent Publication No. 20180087072, including but not limited one or more residues at positions 416, 421, 422, 424, 472, 478, 480, 525 or 542 are mutated. In certain embodiments, the mutation comprises a substitution of a wild-type residue with any different residue, for example an alanine (A) residue, a cysteine (C) residue, an aspartic acid (D) residue, a glutamic acid (E) residue, a histidine (H) residue, a phenylalanine (F) residue, a glycine (G) residue, an asparagine (N) residue, a serine (S) residue or a threonine (T) residue. In other embodiments, the wild-type residue at one or more of positions 416, 418, 421, 422, 424, 446, 448, 472, 476, 478, 479, 480, 481, 525 and/or 542 are replaced with any other residues, including but not limited to, R416D, R416E, S418E, S418D, R422H, S446D, K448A, N476D, P478S, I479Q, I479T, G480D, Q481A, Q481E, K525S, K525A, N527D, N542D, R416E+R422H, R416D+R422H, R416E+K448A, R416D+R422H, K448A+I479Q, K448A+ Q481A. K448A+K525A,R416E, R416D, R416H, R416N, S418A, S418E, D421S, L424F, S446D, K448A, S472D, N476E, N476G, N476K, P478D, I479Q, I479T, G480D, Q481A, Q481C, Q481D, Q481S, Q481E Q481H, K525A, K525C, K525AE, K525I, K525S, K525T, K525V, and/or N542D.

In certain embodiments, the cleavage domain comprises one or more engineered cleavage half-domain (also referred to as dimerization domain mutants) that minimize or prevent homodimerization, as described, for example, in U.S. Pat. Nos. 7,914,796; 8,034,598 and 8,623,618; and U.S. Patent Publication No. 20110201055, the disclosures of all of which are incorporated by reference in their entireties herein. Amino acid residues at positions 446, 447, 478, 479, 483, 484, 486, 487, 490, 491, 496, 498, 499, 500, 531, 534, 537, 538 and 542 of FokI (numbered relative to SEQ ID NO:2) are all targets for influencing dimerization of the FokI cleavage half-domains. The mutations may include mutations to residues found in natural restriction enzymes homologous to FokI. In a preferred embodiment, the mutation at positions 416, 422, 447, 448, 478, 525 and/or 542 (numbered relative to SEQ ID NO:2) comprise replacement of a positively charged amino acid with an uncharged or a negatively charged amino acid. In another embodiment, the engineered cleavage half domain comprises mutations in amino acid residues 499, 496 and 486 in addition to the mutations in one or more amino acid residues 416, 422, 447, 448, or 525, all numbered relative to SEQ ID NO:2.

In certain embodiments, the compositions described herein include engineered cleavage half-domains of FokI that form obligate heterodimers as described, for example, in U.S. Pat. Nos. 7,914,796; 8,034,598; 8,962,281 and 8,623, 618; U.S. Patent Publication Nos. 20080131962 and 20120040398. Thus, in one preferred embodiment, the invention provides fusion molecules wherein the engineered cleavage half-domain comprises a polypeptide in which the wild-type Gln (Q) residue at position 486 is replaced with a Glu (E) residue, the wild-type Ile (I) residue at position 499 is replaced with a Leu (L) residue and the wild-type Asn (N) residue at position 496 is replaced with an Asp (D) or a Glu (E) residue ("ELD" or "ELE") in addition to one or more mutations at positions 416, 422, 447, 448, or 525 (numbered relative to SEQ ID NO:2). In another embodiment, the engineered cleavage half domains are derived from a wild-type FokI cleavage half domain and comprise mutations in the amino acid residues 490, 538 and 537, numbered relative to wild-type FokI (SEQ ID NO:2) in addition to the one or more mutations at amino acid residues 416, 422, 447, 448, or 525. In a preferred embodiment, the invention provides a fusion molecules, wherein the engineered cleavage half-domain comprises a polypeptide in which the wild-type Glu (E) residue at position 490 is replaced with a Lys (K) residue, the wild-type Ile (I) residue at position 538 is replaced with a Lys (K) residue, and the wild-type His (H) residue at position 537 is replaced with a Lys (K) residue or an Arg (R) residue ("KKK" or "KKR") (see U.S. Pat. No. 8,962,281, incorporated by reference herein) in addition to one or more mutations at positions 416, 422, 447, 448, or 525. See, e.g., U.S. Pat. Nos. 7,914,796; 8,034,598 and 8,623,618, the disclosures of which are incorporated by reference in its entirety for all purposes. In other embodiments, the wild-type Asn (N) residue at position 542 is replaced with an Asp (D) residue or the wild-type Pro (P) residue at position 478 is replaced with a Ser (S) residue. In other embodiments, the engineered cleavage half domain comprises the "Sharkey" and/or "Sharkey" mutations (see Guo et al, (2010) J Mol. Biol. 400(1):96-107).

In another embodiment, the engineered cleavage half domains are derived from a wild-type FokI cleavage half domain and comprise mutations in the amino acid residues 490, and 538, numbered relative to wild-type FokI or a FokI homologue in addition to the one or more mutations at amino acid residues 416, 422, 447, 448, or 525. In a preferred embodiment, the invention provides a fusion molecule, wherein the engineered cleavage half-domain comprises a polypeptide in which the wild-type Glu (E) residue at position 490 is replaced with a Lys (K) residue, and the wild-type Ile (I) residue at position 538 is replaced with a Lys (K) residue ("KK") in addition to one or more mutations at positions 416, 422, 447, 448, or 525. In a preferred embodiment, the invention provides a fusion molecule, wherein the engineered cleavage half-domain comprises a polypeptide in which the wild-type Gln (Q) residue at position 486 is replaced with an Glu (E) residue, and the wild-type Ile (I) residue at position 499 is replaced with a Leu (L) residue ("EL") (See U.S. Pat. No. 8,034,598, incorporated by reference herein) in addition to one or more mutations at positions 416, 422, 447, 448, or 525.

In one aspect, the invention provides a fusion molecule wherein the engineered cleavage half-domain comprises a polypeptide in which the wild-type amino acid residue at one or more of positions 387, 393, 394, 398, 400, 402, 416, 422, 427, 434, 439, 441, 447, 448, 469, 478, 487, 495, 497, 506, 516, 525, 529, 534, 542, 559, 569, 570, 571 in the FokI catalytic domain are mutated. Nuclease domains comprising one or more mutations as shown in any of the appended Tables and Figures are provided. In some embodiments, the one or more mutations alter the wild type amino acid from a positively charged residue to a neutral residue or a negatively charged residue. In any of these embodiments, the mutants described may also be made in a FokI domain comprising one or more additional mutations. In preferred embodiments, these additional mutations are in the dimerization domain, e.g. at positions 418, 432, 441, 481, 483, 486, 487, 490, 496, 499, 523, 527, 537, 538 and/or 559. Non-limiting examples of mutations include mutations (e.g., substitutions) of the wild-type residues of any cleavage domain (e.g., FokI or homologue of FokI) at positions 393, 394, 398, 416, 421, 422, 442, 444, 472, 473, 478, 480, 525 or 530 with any amino acid residue (e.g., K393X, K394X, R398X, R416S, D421X, R422X, K444X, S472X, G473X, 5472, P478X, G480X, K525X, A530X and/or, N542X, where the first residue depicts wild-type and X refers to any amino acid that is substituted for the wild-type residue). In some embodiments, X is E, D, H, A, K, S, T, D or N. Other exemplary mutations include S418E, S418D, S446D, K448A, P478S, I479Q, I479T, Q481A, Q481N, Q481E, A530E, A530K and/or N542D wherein the amino acid residues are numbered relative to full length FokI wild-type cleavage domain and homologues thereof. In certain embodiments, combinations may include 416 and 422, a mutation at position 416 and K448A, K448A and I479Q, K448A and Q481A and/or K448A and a mutation at position 525. In one embodiment, the wild-residue at position 416 may be replaced with a Glu (E) residue (R416E), the wild-type residue at position 422 is replaced with a His (H) residue (R422H), and the wild-type residue at position 525 is replaced with an Ala (A) residue. The cleavage domains as described herein can further include additional mutations, including but not limited to at positions 432, 441, 483, 486, 487, 490, 496, 499, 527, 537, 538 and/or 559, for example dimerization domain mutants (e.g., ELD, KKR) and or nickase mutants (mutations to the catalytic domain). The cleavage half-domains with the mutations described herein form heterodimers as known in the art.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases (e.g., ZFNs and/or TALENs) can be screened for activity prior to use, for example in a yeast-based chromosomal system as described in as described in U.S. Pat. No. 8,563,314.

In certain embodiments, the nuclease comprises a CRISPR/Cas system. The CRISPR (clustered regularly interspaced short palindromic repeats) locus, which encodes RNA components of the system, and the Cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In some embodiments, the CRISPR-Cpf1 system is used. The CRISPR-Cpf1 system, identified in *Francisella* spp, is a class 2 CRISPR-Cas system that mediates robust DNA interference in human cells. Although functionally conserved, Cpf1 and Cas9 differ in many aspects including in their guide RNAs and substrate specificity (see Fagerlund et al, (2015) *Genom Bio* 16:251). A major difference between Cas9 and Cpf1 proteins is that Cpf1 does not utilize tracrRNA, and thus requires only a crRNA. The FnCpf1 crRNAs are 42-44 nucleotides long (19-nucleotide repeat and 23-25-nucleotide spacer) and contain a single stem-loop, which tolerates sequence changes that retain secondary structure. In addition, the Cpf1 crRNAs are significantly shorter than the ~100-nucleotide engineered sgRNAs required by Cas9, and the PAM requirements for FnCpf1 are 5'-TTN-3' and 5'-CTA-3' on the displaced strand. Although both Cas9 and Cpf1 make double strand breaks in the target DNA, Cas9 uses its RuvC- and HNH-like domains to make blunt-ended cuts within the seed sequence of the guide RNA, whereas Cpf1 uses a RuvC-like domain to produce staggered cuts outside of the seed. Because Cpf1 makes staggered cuts away from the critical seed region, NHEJ will not disrupt the target site, therefore ensuring that Cpf1 can continue to cut the same site until the desired HDR recombination event has taken place. Thus, in the methods and compositions described herein, it is understood that the term "Cas" includes both Cas9 and Cfp1 proteins. Thus, as used herein, a "CRISPR/Cas system" refers both CRISPR/Cas and/or CRISPR/Cfp1 systems, including both nuclease and/or transcription factor systems.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof such as derivative Cas proteins. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein. In some embodiments, the Cas protein is a small Cas9 ortholog for delivery via an AAV vector (Ran et al (2015) *Nature* 510, p. 186).

The nuclease(s) may make one or more double-stranded and/or single-stranded cuts in the target site. In certain embodiments, the nuclease comprises a catalytically inactive cleavage domain (e.g., FokI and/or Cas protein). See, e.g., U.S. Pat. Nos. 9,200,266; 8,703,489 and Guillinger et al. (2014) *Nature Biotech.* 32(6):577-582. The catalytically inactive cleavage domain may, in combination with a catalytically active domain act as a nickase to make a single-stranded cut. Therefore, two nickases can be used in combination to make a double-stranded cut in a specific region. Additional nickases are also known in the art, for example, McCaffery et al. (2016) *Nucleic Acids Res.* 44(2):ell. doi: 10.1093/nar/gkv878. Epub 2015 Oct. 19.

In certain embodiments, the nuclease is a zinc finger nuclease comprising first and second (also referred to as "left and right" and "partner") zinc finger nucleases, each comprising a zinc finger DNA-binding domain and a cleavage domain (e.g., engineered FokI). The ZFN may be carried by one or more AAV vectors. In certain embodiments, separate AAV vectors carry the left and right ZFNs of the nuclease. The AAV vector(s) may include additional coding and/or non-coding sequences, including but not limited to a 5' ITR, one or more enhancer sequences (e.g., ApoE enhancer), one or more promoter sequences (e.g., hAAT promoter), a 5' UTR, one or more intron sequences (e.g., human β globin/IgG chimeric intron), an N-terminal peptide coding sequence, an NLS signal, one or more WPRE sequences (e.g., WPREmut6), a polyA signal and/or a 3'ITR. Exemplary nuclease AAVs are shown in Tables 4 and 5 below. It will be apparent that one or more of the listed elements (excluding the ZFN-encoding sequences) may be omitted; replaced with analogous sequences (e.g., different promoter sequences, different WPRE sequences such as those known in the art or described in Example 4), different intron sequences, etc.); and/or additional elements may be added. The AAV vector(s) encoding the nucleases may be used in systems with donors, for instant 2 ZFN AAVs (e.g., left and right ZFN AAVs as disclosed in Table 4 and 5) in combination with a donor AAV, typically encoding a therapeutic peptide. The AAV donors can include one or more of the following elements: 5' and/or 3'ITRs from any source; left and/or right homology arms (to albumin) flanking the transgene (therapeutic protein-encoding sequence of any length encoding any protein or functional fragment thereof) of any length; a splice acceptor sequence; and/or a polyadenylation (polyA) signal. In certain embodiments, the AAV donor encodes a Factor IX, IDS or IDUA protein, for example a donor as shown in Tables 6-8 below.

Delivery

The proteins (e.g., nucleases), polynucleotides and/or compositions comprising the proteins and/or polynucleotides described herein may be delivered to a target cell by any suitable means, including, for example, by injection of the protein and/or mRNA components.

Suitable cells include but not limited to eukaryotic and prokaryotic cells and/or cell lines. Non-limiting examples of such cells or cell lines generated from such cells include T-cells, COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*. In certain embodiments, the cell line is a CHO-K1, MDCK or HEK293 cell line. Suitable cells also include stem cells such as, by way of example, embryonic stem cells, induced pluripotent stem cells (iPS cells), hematopoietic stem cells, neuronal stem cells and mesenchymal stem cells.

Methods of delivering proteins comprising DNA-binding domains as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

DNA binding domains and fusion molecules comprising these DNA binding domains as described herein may also be delivered using vectors containing sequences encoding one or more of the DNA-binding protein(s). Additionally, additional nucleic acids (e.g., donors) also may be delivered via these vectors. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more DNA-binding protein-encoding sequences and/or additional nucleic acids as appropriate. Thus, when one or more DNA-binding proteins as described herein are introduced into the cell, and additional DNAs as appropriate, they may be carried on the same vector or on different vectors. When multiple vectors are used, each vector may comprise a sequence encoding one or multiple DNA-binding proteins and additional nucleic acids as desired.

Conventional viral and non-viral based gene transfer methods can be used to introduce nucleic acids encoding engineered DNA-binding proteins in cells (e.g., mammalian cells) and target tissues and to co-introduce additional nucleotide sequences as desired. Such methods can also be used to administer nucleic acids (e.g., encoding DNA-binding proteins and/or donors) to cells in vitro. In certain embodiments, nucleic acids are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, mRNA, artificial virions, and agent-enhanced uptake of DNA. Sonoporation using, e.g., the Sonitron 2000 system (Rich-Mar) can also be used for delivery of nucleic acids. In a preferred embodiment, one or more nucleic acids are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074,596 and 8,153,773, incorporated by reference herein.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386, 4,946,787; and 4,897,355) and lipofection reagents are sold commercially (e.g., Transfectam™, Lipofectin™, and Lipofectamine™ RNAiMAX). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7) p. 643).

The use of RNA or DNA viral based systems for the delivery of nucleic acids encoding engineered DNA-binding proteins, and/or donors (e.g. CARs or ACTRs) as desired takes advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS USA* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS USA* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al.,

*Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery system based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8, AAV8.2, AAV9 and AAVrh10 and pseudo-typed AAV such as AAV2/8, AAV2/5 and AAV2/6 can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion with a viral coat protein on the outer surface of the virus. The ligand is chosen to have affinity for a receptor known to be present on the cell type of interest. For example, Han et al., (*Proc. Natl. Acad. Sci. USA* 92:9747-9751 (1995)), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion molecule comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Delivery methods for CRISPR/Cas systems can comprise those methods described above. For example, in animal models, in vitro transcribed Cas encoding mRNA or recombinant Cas protein can be directly injected into one-cell stage embryos using glass needles to genome-edited animals. To express Cas and guide RNAs in cells in vitro, typically plasmids that encode them are transfected into cells via lipofection or electroporation. Also, recombinant Cas protein can be complexed with in vitro transcribed guide RNA where the Cas-guide RNA ribonucleoprotein is taken up by the cells of interest (Kim et al (2014) *Genome Res* 24(6):1012). For therapeutic purposes, Cas and guide RNAs can be delivered by a combination of viral and non-viral techniques. For example, mRNA encoding Cas may be delivered via nanoparticle delivery while the guide RNAs and any desired transgene or repair template are delivered via AAV (Yin et al (2016) *Nat Biotechnol* 34(3) p. 328).

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by re-implantation of the cells into a patient, usually after selection for cells which have incorporated the vector.

Ex vivo cell transfection for diagnostics, research, transplant or for gene therapy (e.g., via re-infusion of the transfected cells into the host organism) is well known to those of skill in the art. In a preferred embodiment, cells are isolated from the subject organism, transfected with a DNA-binding proteins nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Tad (differentiated antigen presenting cells) (see Inaba et al., *J. Exp. Med.* 176:1693-1702 (1992)).

Stem cells that have been modified may also be used in some embodiments. For example, neuronal stem cells that have been made resistant to apoptosis may be used as therapeutic compositions where the stem cells also contain the ZFP TFs of the invention. Resistance to apoptosis may come about, for example, by knocking out BAX and/or BAK using BAX- or BAK-specific ZFNs (see, U.S. Pat. No. 8,597,912) in the stem cells, or those that are disrupted in a caspase, again using caspase-6 specific ZFNs for example.

Vectors (e.g., retroviruses, adenoviruses, liposomes, etc.) containing therapeutic DNA-binding proteins (or nucleic acids encoding these proteins) can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington's Pharmaceutical Sciences, 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells, including T-cells and stem cells of any type. Suitable cell lines for protein expression are known to those of skill in the art and include, but are not limited to COS, CHO (e.g., CHO-S, CHO-K1, CHO-DG44, CHO-DUXB11), VERO, MDCK, WI38, V79, B14AF28-G3, BHK, HaK, NS0, SP2/0-Ag14, HeLa, HEK293 (e.g., HEK293-F, HEK293-H, HEK293-T), perC6, insect cells such as *Spodoptera fugiperda* (Sf), and fungal cells such as *Saccharomyces*, *Pichia* and *Schizosaccharomyces*. Progeny, variants and derivatives of these cell lines can also be used.

Applications

Use of engineered nucleases in treatment and prevention of disease is one of the most significant developments in medicine in the coming years. The methods and compositions described herein serve to increase the specificity of these novel tools to ensure that the desired target sites will be the primary place of cleavage. Minimizing or eliminating off-target cleavage will be required to realize the full potential of this technology, for all in vitro, in vivo and ex vivo applications.

Exemplary genetic diseases include, but are not limited to, achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipidius, neurofibromatosis, Neimann-Pick disease, osteogenesis imperfecta, phenylketonuria (PKU). porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted DNA cleavage and/or homologous recombination include acquired immunodeficiencies, lysosomal storage diseases (e.g., Gaucher's disease, GM1, Fabry disease and Tay-Sachs disease), mucopolysaccahidosis (e.g. MPSII (Hunter's disease), MPSI (Hurler's disease), hemoglobinopathies (e.g., sickle cell diseases, HbC, α-thalassemia, β-thalassemia) and hemophilias. See, e.g., U.S. Pat. Nos. 9,877,988 and 9,956,247. In particular, glucocerebrosidase (GBA) is deficient in Gaucher's, alpha-galactosidase (GLA) is deficient in Fabry's, iduronate-2-sulfatase deficiency (IDS) is deficient in MPS II (Hunter's), alpha-L iduronidase deficiency (IDUA) is deficient in MPS I (Hurler's), and sphingomyelin phosphodiesterase 1 deficiency (SMPD1) is deficient in Niemann-Pick's. Therefore, donors expressing one or more of the proteins lacking or deficient in these diseases can be introduced using the nucleases described herein to provide treatment and/or prevention for these diseases.

Such methods also allow for treatment of infections (viral or bacterial) in a host (e.g., by blocking expression of viral or bacterial receptors, thereby preventing infection and/or spread in a host organism) to treat genetic diseases.

Targeted cleavage of infecting or integrated viral genomes can be used to treat viral infections in a host. Additionally, targeted cleavage of genes encoding receptors for viruses can be used to block expression of such receptors, thereby preventing viral infection and/or viral spread in a host organism. Targeted mutagenesis of genes encoding viral receptors (e.g., the CCR5 and CXCR4 receptors for HIV) can be used to render the receptors unable to bind to virus, thereby preventing new infection and blocking the spread of existing infections. See, U.S. Patent Publication No. 2008/015996. Non-limiting examples of viruses or viral receptors that may be targeted include herpes simplex virus (HSV), such as HSV-1 and HSV-2, varicella zoster virus (VZV), Epstein-Barr virus (EBV) and cytomegalovirus (CMV), HHV6 and HHV7. The hepatitis family of viruses includes hepatitis A virus (HAV), hepatitis B virus (HBV), hepatitis C virus (HCV), the delta hepatitis virus (HDV), hepatitis E virus (HEV) and hepatitis G virus (HGV). Other viruses or their receptors may be targeted, including, but not limited to, Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae; lentiviruses (e.g., HTLV-I; HTLV-II; HIV-1 (also known as HTLV-III, LAV, ARV, hTLR, etc.) HIV-II); simian immunodeficiency virus (SIV), human papillomavirus (HPV), influenza virus and the tick-borne encephalitis viruses. See, e.g. Virology, 3rd Edition (W. K. Joklik ed. 1988); Fundamental Virology, 2nd Edition (B. N. Fields and D. M. Knipe, eds. 1991), for a description of these and other viruses. Receptors for HIV, for example, include CCR-5 and CXCR-4.

Thus, heterodimeric cleavage domain variants as described herein provide broad utility for improving ZFN specificity in gene modification applications. These variant cleavage domains may be readily incorporated into any existing ZFN by either site directed mutagenesis or subcloning to improve the in vivo specificity of any ZFN dimers.

As noted above, the compositions and methods described herein can be used for gene modification, gene correction, and gene disruption. Non-limiting examples of gene modification includes homology directed repair (HDR)-based targeted integration; HDR-based gene correction; HDR-based gene modification; HDR-based gene disruption; NHEJ-based gene disruption and/or combinations of HDR, NHEJ, and/or single strand annealing (SSA). Single-Strand Annealing (SSA) refers to the repair of a double strand break between two repeated sequences that occur in the same orientation by resection of the DSB by 5'-3' exonucleases to expose the 2 complementary regions. The single-strands encoding the 2 direct repeats then anneal to each other, and the annealed intermediate can be processed such that the single-stranded tails (the portion of the single-stranded DNA that is not annealed to any sequence) are be digested away, the gaps filled in by DNA Polymerase, and the DNA ends rejoined. This results in the deletion of sequences located between the direct repeats.

Compositions comprising cleavage domains (e.g., ZFNs, TALENs, CRISPR/Cas systems) and methods described herein can also be used in the treatment of various genetic diseases and/or infectious diseases.

The compositions and methods can also be applied to stem cell based therapies, including but not limited to: correction of somatic cell mutations by short patch gene conversion or targeted integration for monogenic gene therapy; disruption of dominant negative alleles; disruption of genes required for the entry or productive infection of pathogens into cells; enhanced tissue engineering, for example, by modifying gene activity to promote the differentiation or formation of functional tissues; and/or disrupting gene activity to promote the differentiation or formation of functional tissues; blocking or inducing differentiation, for example, by disrupting genes that block differentiation to promote stem cells to differentiate down a specific lineage pathway, targeted insertion of a gene or siRNA expression cassette that can stimulate stem cell differentiation, targeted insertion of a gene or siRNA expression cassette that can block stem cell differentiation and allow better expansion and maintenance of pluripotency, and/or targeted insertion of a reporter gene in frame with an endogenous gene that is a marker of pluripotency or differentiation state that would allow an easy marker to score differentiation state of stem cells and how changes in media, cytokines, growth conditions, expression of genes, expression of siRNA, shRNA or miRNA molecules, exposure to antibodies to cell surface markers, or drugs alter this state; somatic cell nuclear transfer, for example, a patient's own somatic cells can be isolated, the intended target gene modified in the appropriate manner, cell clones generated (and quality controlled to ensure genome safety), and the nuclei from these cells isolated and transferred into unfertilized eggs to generate patient-specific hES cells that could be directly injected or differentiated before engrafting into the patient, thereby reducing or eliminating tissue rejection; universal stem cells by knocking out MHC receptors (e.g., to generate cells of diminished or altogether abolished immunological identity). Cell types for this procedure include but are not limited to, T-cells, B cells, hematopoietic stem cells, and embryonic stem cells. Additionally, induced pluripotent stem cells (iPSC) may be used which would also be generated from a patient's own somatic cells. Therefore, these stem cells or their derivatives (differentiated cell types or tissues) could be potentially engrafted into any person regardless of their origin or histocompatibility.

The compositions and methods can also be used for somatic cell therapy, thereby allowing production of stocks of cells that have been modified to enhance their biological properties. Such cells can be infused into a variety of patients, independent of the donor source of the cells and their histocompatibility to the recipient.

In addition to therapeutic applications, the increased specificity provided by the variants described herein when used in engineered nucleases can be used for crop engineering, cell line engineering and the construction of disease models. The obligate heterodimer cleavage half-domains provide a straightforward means for improving nuclease properties.

The engineered cleavage half domains described can also be used in gene modification protocols requiring simultaneous cleavage at multiple targets either to delete the intervening region or to alter two specific loci at once. Cleavage at two targets would require cellular expression of four ZFNs or TALENs, which could yield potentially ten different active ZFN or TALEN combinations. For such applications, substitution of these novel variants for the wild-type nuclease domain would eliminate the activity of the undesired combinations and reduce chances of off-target cleavage. If cleavage at a certain desired DNA target requires the activity of the nuclease pair A+B, and simultaneous cleavage at a second desired DNA target requires the activity of the nuclease pair X+Y, then use of the mutations described herein can prevent the pairings of A with A, A with X, A with Y and so on. Thus, these FokI mutations decrease nonspecific cleavage activity as a result of "illegitimate" pair formation and allow the generation of more efficient orthogonal mutant pairs of nucleases (see co-owned patent U.S. Patent Publication Nos. 20080131962 and 20090305346).

EXAMPLES

Example 1

Preparation of ZFNs

ZFNs targeted to human albumin gene was designed and incorporated into plasmids vectors essentially as described in Urnov et al. (2005) *Nature* 435(7042):646-651; Perez et al (2008) *Nature Biotechnology* 26(7):808-816, and U.S. Pat. No. 9,394,545.

Example 2

Optimizing Albumin-Specific ZFNs

The binding site of the left hand ZFN partner (SBS47171-FLAG, see Table 1) comprises a SNP in 20% of humans (see FIG. 1). In the wild type sequence, the sequence comprises an AT base pair (indicated by the oval), while in the sequence comprising the SNP, there is a GC base pair in this position (indicated in rectangle above sequence). In human hepatocytes that are heterozygous for the wild type and SNP albumin sequences, the 47171-FLAG/47898-FLAG pair has a 3-4 fold preference for the wild type sequence (see FIG. 2). A second left hand partner was identified (42875) that was found to cleave the wild type albumin sequence and the SNP-containing sequence with equal activity, however the 42875/47898 pair also showed some cleavage activity at a SMCHD1 off target site.

Thus, studies were performed with additional candidate ZFNs wherein modifications were made to the phosphate contacting amino acids within the ZFP backbone. The proteins used are shown below in Table 1.

TABLE 1

Albumin-specific ZFN designs

| ZFN Name target sequence | F1 | F2 | F3 | F4 | F5 | F6 | Domain linker | other |
|---|---|---|---|---|---|---|---|---|
| SBS47171-FLAG ttTGGGAT AGTTATGA Attcaatc ttca (SEQ ID NO: 12) | QSGNLSR (SEQ ID NO: 14) | LKQNLCM (SEQ ID NO: 15) | WADNLQN (SEQ ID NO: 16) | TSGNLTR (SEQ ID NO: 17) | RQSHLCL (SEQ ID NO: 18) | N/A | 5.6 | N-term 3x FLAG |
| SBS42875-FLAG ttTGGGAT AGTTATGA Attcaatc ttca (SEQ ID NO: 12) | QSGNLAR (SEQ ID NO: 19) | LKQNLCM (SEQ ID NO: 15) | WQSNLQN (SEQ ID NO: 20) | TSGNLTR (SEQ ID NO: 17) | RRSHLTS (SEQ ID NO: 21) | N/A | 5.6 | N-term 3x FLAG |
| 42877-FLAG ttTGGGAT AGTTATGA Attcaatc ttca (SEQ ID NO: 12) | QSGNLAR (SEQ ID NO: 19) | LKQNLCM (SEQ ID NO: 15) | LITTLRN (SEQ ID NO: 22) | TSGNLTR (SEQ ID NO: 17) | RQSHLCL (SEQ ID NO: 18) | N/A | 5.6 | N-term 3x FLAG |
| 42908-FLAG ttTGGGAT AGTTATGA Attcaatc ttca (SEQ ID NO: 12) | QSGNLAR (SEQ ID NO: 19) | LKQNLCM (SEQ ID NO: 15) | WASNLQN (SEQ ID NO: 23) | TSGNLTR (SEQ ID NO: 17) | RQSHLCL (SEQ ID NO: 18) | N/A | 5.6 | N-term 3x FLAG |
| 47898-FLAG ccTATCCA TTGCACTA TGCTttat ttaa (SEQ ID NO: 13) | TPQLLDR (SEQ ID NO: 24) | LKHNLLT (SEQ ID NO: 25) | DQSNLNA (SEQ ID NO: 26) | RNFSLTM (SEQ ID NO: 27) | LRHDLDR (SEQ ID NO: 28) | HRSNLNK (SEQ ID NO: 29) | 5.6 | N-term 3x FLAG |

TABLE 1-continued

Albumin-specific ZFN designs

| ZFN Name target sequence | F1 | F2 | F3 | F4 | F5 | F6 | Domain linker | other |
|---|---|---|---|---|---|---|---|---|
| 47874-FLAG ccTATCCA TTGCACTA TGCTttat ttaa (SEQ ID NO: 13) | QSSDLSR (SEQ ID NO: 30) | LKHNLLT (SEQ ID NO: 25) | DQSNLRA (SEQ ID NO: 31) | RNFSLTM (SEQ ID NO: 27) | LRHDLER (SEQ ID NO: 32) | HRSNLNK (SEQ ID NO: 29) | 5.6 | N-term 3x FLAG |
| 47931-FLAG ccTATCCA TTGCACTA TGCTttat ttaa (SEQ ID NO: 13) | TPQLLDR (SEQ ID NO: 24) | LKWNLRT (SEQ ID NO: 33) | DQSNLNA (SEQ ID NO: 26) | RNFSLTM (SEQ ID NO: 27) | LRHDLDR (SEQ ID NO: 28) | HRSNLNK (SEQ ID NO: 29) | 5.6 | N-term 3x FLAG |

The ZFNs listed above were then modified to comprise alterations in their ZFP backbones to reduce any potential non-specific contacts between the ZFP and the DNA phosphate backbone (see U.S. Patent Publication No. US-2018-0087072-A1). In Table 2A and 2B below, exemplary ZFP backbone changes are shown under the heading of the parent ZFN from Table 1 along with the new SBS unique numeric identifiers assigned to each variant.

Table 2: Phosphate Contact Variant ZFNs

TABLE 2A

| Left partners | | | | | | | | |
|---|---|---|---|---|---|---|---|---|
| m5Q Variants | | | | | 47171-FLAG | 42875-FLAG | 42877-FLAG | 42908-FLAG |
| F1 | F2 | F3 | F4 | F5 | SBS# | SBS# | SBS# | SBS# |
|  |  |  |  |  | 70949 | 70957 | 70965 | 70973 |
| Q |  |  |  |  | 70950 | 70958 | 70966 | 70974 |
|  | Q |  |  |  | 70951 | 70959 | 70967 | 70975 |
|  |  | Q |  |  | 70952 | 70960 | 70968 | 70976 |
| Q | Q |  |  |  | 70953 | 70961 | 70969 | 70977 |
| Q |  | Q |  |  | 70954 | 70962 | 70970 | 70978 |
|  | Q | Q |  |  | 70955 | 70963 | 70971 | 70979 |
| Q | Q | Q |  |  | 70956 | 70964 | 70972 | 70980 |

TABLE 2B

| Right partners | | | | | | |
|---|---|---|---|---|---|---|
| m5Q Variants | | | | | 47898-FLAG | 47874-FLAG |
| F1 | F2 | F3 | F4 | F5 | SBS# | SBS# |
|  |  |  |  |  | 70981 | 70989 |
| Q |  |  |  |  | 70982 | 70990 |
|  | Q |  |  |  | 70983 | 70991 |
|  |  |  | Q |  | 70984 | 70992 |
| Q | Q |  |  |  | 70985 | 70993 |
| Q |  |  | Q |  | 70986 | 70994 |
|  | Q |  | Q |  | 70987 | 70995 |
| Q | Q |  | Q |  | 70988 | 70996 |

These proteins were then tested for activity against either the albumin locus (ALB) or the SMCHD1 off target, where the variants were paired with the original right (47898-FLAG)- or left-hand partner (47171-FLAG). K562 cells were electroporated with ZFN mRNA by Amaxa electroporation following manufacture's instruction. Cells were harvested 16 hours after electroporation. gDNA was extracted using QuickExtract™ DNA Extraction Solution (Lucigen) following manufacture's instruction. Percentage of indels was measured by MiSeq sequencing of PCR products obtained with primers surrounding Albumin ZFN cutting site or SMCHD1 off-target. High activity was seen in all variants and, increased specificity (comparison to off-target sites) was observed in most variants, particularly F1 and F3 variants (FIG. 3A).

Next, phosphate contacting amino acid side chain mutations made in the ELD/KKR FokI nuclease domains (see U.S. Pat. No. 8,962,281) were paired with ZFP backbone mutations described above. In these experiments, the parent ZFNs are shown in Table 1 were recapitulated comprising mutations in both the backbone and in the nuclease domain, and each was given a new unique numeric identified (see Table 3).

TABLE 3

Albumin specific ZFN variants

| SBS number | ZFN parent | Backbone mutation(s) | Fok* |
|---|---|---|---|
| 71545 | 42875-FLAG | F1m5Q, F3m5Q | ELD-R416H |
| 71557 | 42875-FLAG | F1m5Q, F3m5Q | ELD-N542D |
| 71673 | 47898-FLAG | F3m5Q | KKR-R416H |
| 71721 | 47874-FLAG | F3m5Q | KKR-R416H |
| 71739 | 47874-FLAG | F1m5Q, F3m5Q | KKR-S418P |
| 71741 | 47874-FLAG | F1m5Q, F3m5Q | KKR-L424F |
| 71721 | 47874-FLAG | F3m5Q | KKR-R416H |
| 71728 | 47874-FLAG | F3m5Q | KKR-P478S |
| 71639 | 42908-FLAG | F1m5Q, F3m5Q | ELD |
| 71641 | 42908-FLAG | F1m5Q, F3m5Q | ELD-R416H |
| 71653 | 42908-FLAG | F1m5Q, F3m5Q | ELD-N542D |
| 71696 | 47898-FLAG | F1m5Q, F3m5Q | KKR-P478S |

*FokI domains may be numbered relative to full-length as shown in the Table or with respect to cleavage domain of FokI only (e.g., N542D and N159D refer to the same engineered FokI domain and P478S and P95S refer to the same engineered FokI domain)

Pairs comprising these ZFNs were then tested in K562 cells to observe ZFN activity at the albumin locus and at the off-target site SMCHD1. Briefly, K562 cells were transfected with albumin-targeting ZFNs as indicated. Cells were assessed for ZFN activity (% indels) by deep sequencing 24 hours after transfection as described above.

Figure 3B:
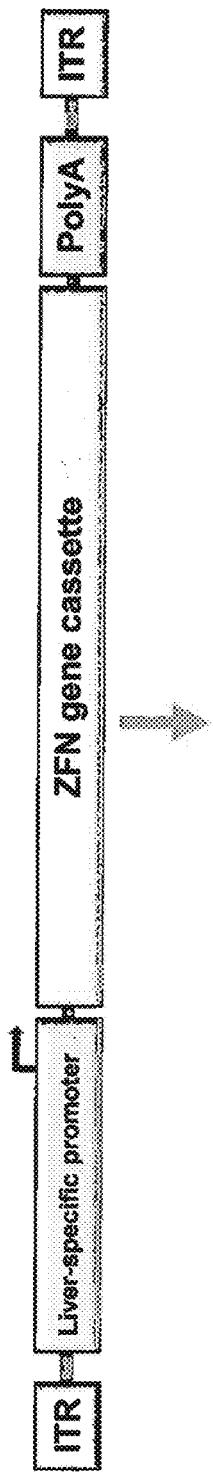

The results (shown in FIGS. 3A-3C) demonstrate that the albumin-specific activity was greatly improved while the off-target activity fell to background levels. FIGS. 3A and 3B shows results at off-target site SMCHD1. An unbiased capture assay was also used to identify potential off target loci for these ZFN pairs in both K562 cells and HepG2 cells and as shown (see FIG. 3C), the modified ZFN pairs had almost no detectable activity at these sites.

Thus, optimized human albumin-specific ZFNs were designed that maintain a high level of on target cleavage at the albumin locus while being tolerant to the A to G SNP and having a high degree of specificity.

The optimized ZFNs were also tested for activity (cleavage and targeted integration of a donor) in iPS-derived human hepatocytes. In brief, iPS-derived human hepatocytes were purchased from Cellular Dynamics international, plated and cultured following manufacture's protocol. The cells were transduced with human ZFNs AAV at day 4 post plating in the following dose: low—30 MOI, mid—100 MOI and high—300 MOI. Next day the cells were transduced with human Donor AAV: low—240 MOI, mid—800 MOI and high 2400 MOI. Cells and conditional medium were harvested for the analysis at day 7 post ZFN AAV transduction.

Figure 3D:
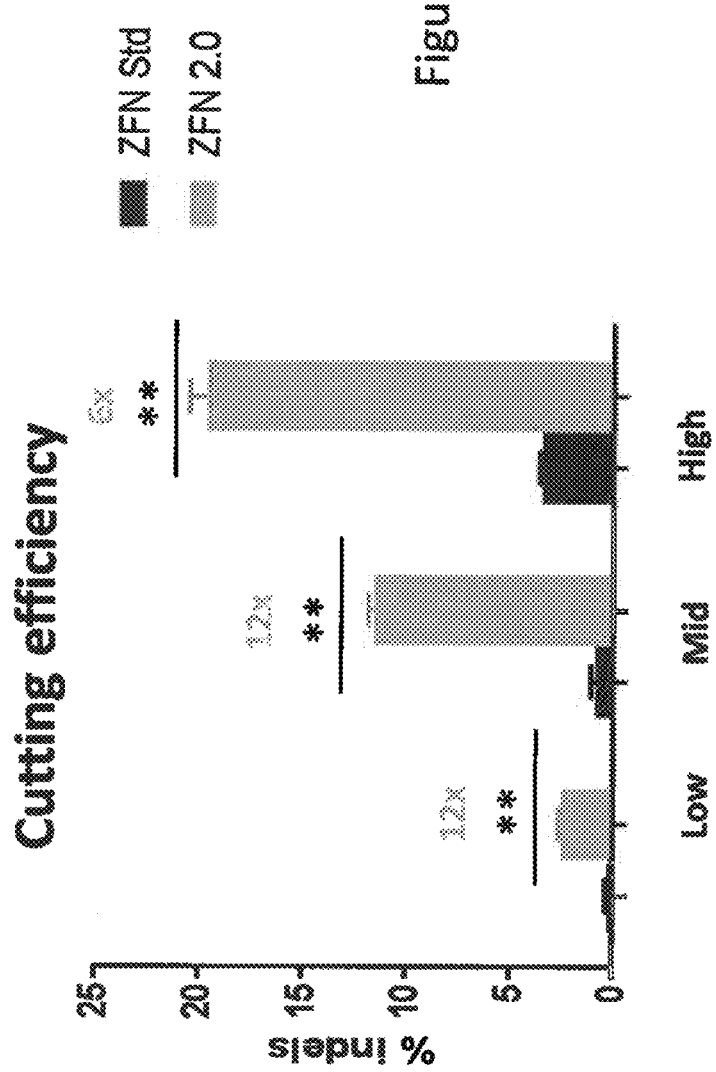
Figure 3E:
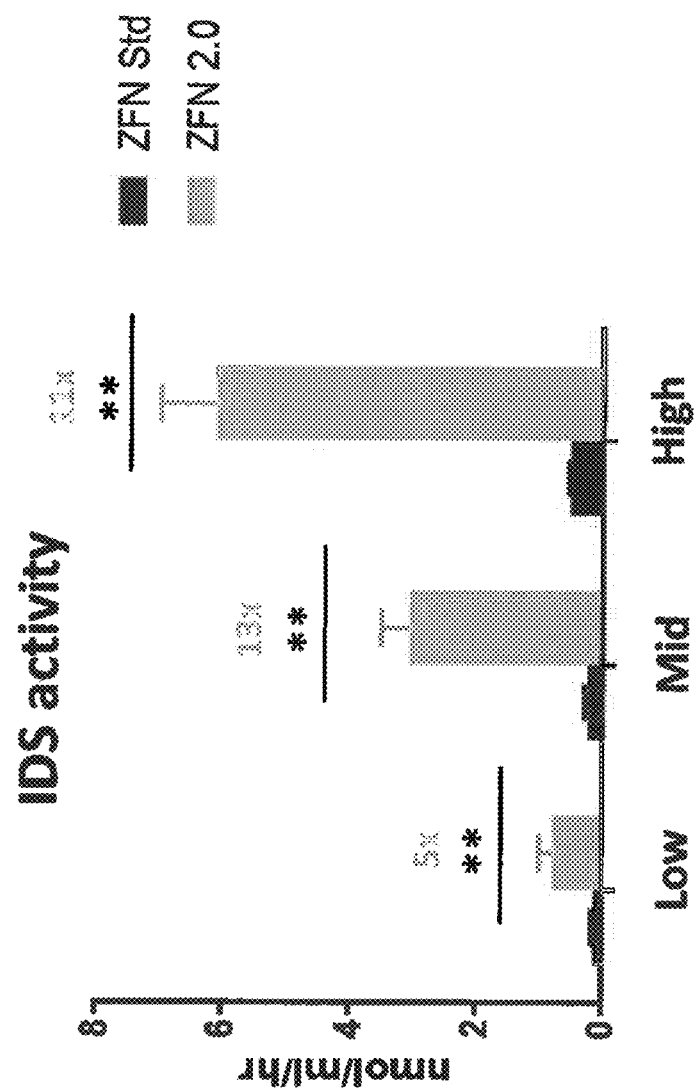

As shown in FIGS. 3D and 3E(i), optimized ZFNs showed up to 12-fold higher levels of cleavage efficiency and 13-fold higher level of transgene (IDS) production from the transgene integrated using optimized ZFNs as compared to the parent ZFNs.

Studies were carried out to evaluate the expression of a transgene captured following cleavage with the two ZFN pairs over time. In brief, human iPSC-derived hepatocytes were transduced in triplicate with rAAV2/6 vectors encoding the first (47171:47898) or second (71557:71728) generation ZFNs in combination with the human IDS transgene donor (SB-IDS). IDS enzyme activity (expressed as nmol of product per hour per mL of cell culture supernatant [nmol/hr/mL]) on Day 5 and Day 7 post-transduction was determined by IDS enzyme activity assay. ZFNs and SB-IDS donor were delivered in a left ZFN:right ZFN:Donor ratio of 1:1:2. At doses of 100:100:200 (MOI of ZFN:ZFN:Donor), treatment of the cells with the second generation ZFN pair resulted in 2-fold and 5× more IDS in the cell supernatant at days 5 and 7 respectively than treatment with the first generation pair. At doses of 300:300:600, treatment of the cells with the second generation ZFN pair resulted in 7-fold and 21-fold more IDS in the supernatant at days 5 and 7 respectively than the first generation pair (see FIG. 3E(ii)).

Next, primary human hepatocytes that were heterozygous for an A to G SNP within the left ZFN binding site were transfected with messenger RNA (mRNA) encoding the 47171/47898 or the 71557/47898 pairs at concentrations of 10 or 50 ng mRNA per ZFN. Genomic DNA was evaluated by MiSeq deep sequencing for levels of gene modification (% insertions and deletions [indels]) at the wildtype (A:T) or SNP (G:C) on-target site. The results (see FIGS. 3F(i) and 3F(ii)) demonstrated that the 71557/47898 pair had equal activity at both the SNP containing and the non-SNP containing alleles.

Figure 3G:
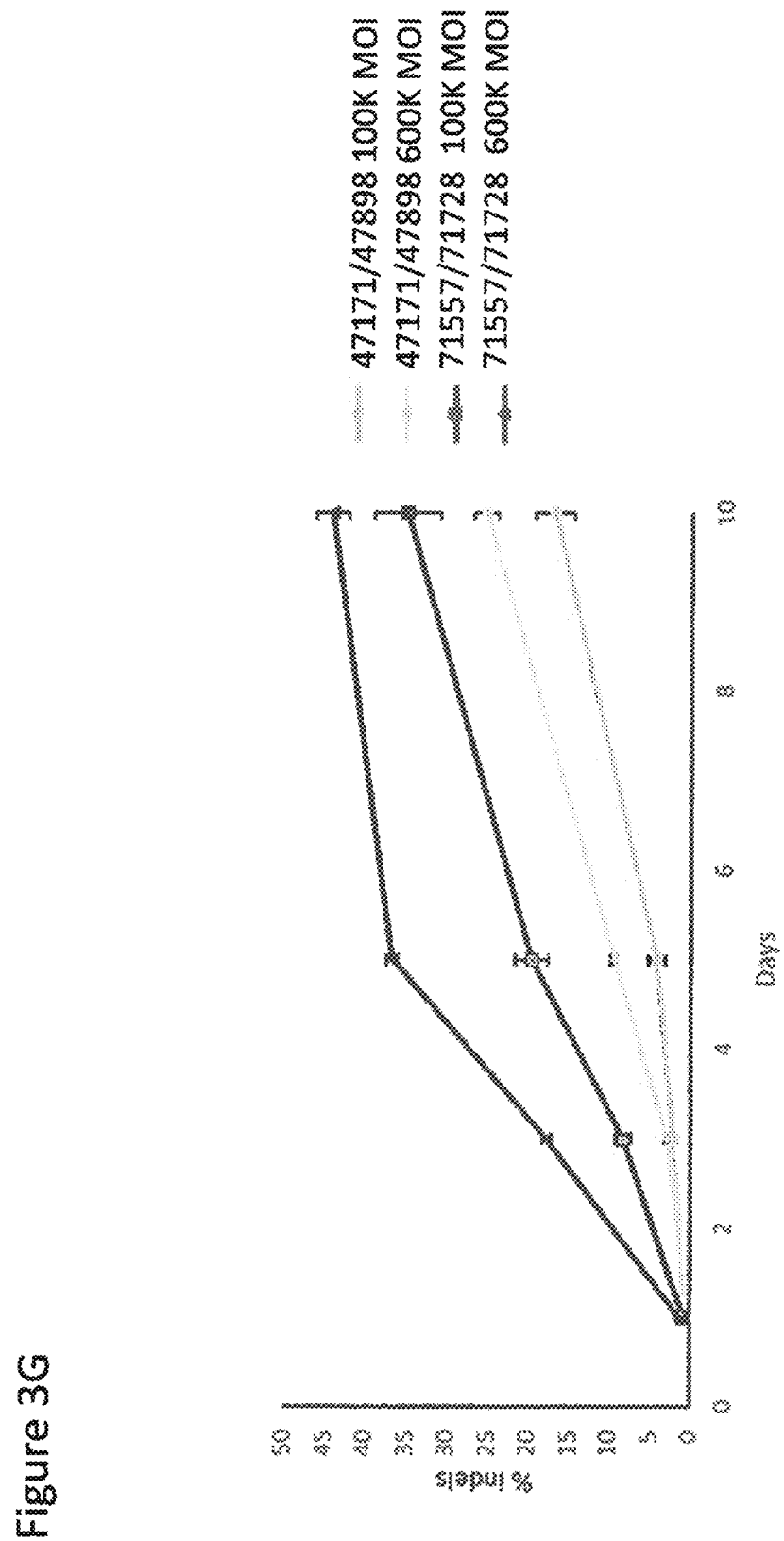

The rates of gene modification in cells in vitro were also analyzed. Gene modification levels following AAV2/6-mediated delivery of ZFNs (100K and 600K MOIs) to cells was assessed over 10 days of exposure in human primary hepatocytes in three biological replicates. Cells were harvested on Days 1, 3, 5 and 10, genomic DNA was isolated, PCR amplified and MiSeq deep sequenced. The 71557/71728 ZFN pair showed faster kinetics over 10 days compared to the 47171/47898 ZFN pair (FIG. 3G). Faster kinetics for both dose levels of the 71557/71728 ZFN pair were evident as early as Day 3 where this pair yielded 8.3% and 17.8% indels for 100K and 600K dose levels, respectively, compared to 2.2% and 3.0% indels with the 47171/47898 ZFN pair. The 71557/71728 ZFN pair appeared to reach saturation of effect above 40% indels on Day 10. Treatment with the 71557/71728 ZFN pair resulted in higher levels of gene modification over time compared to the 47171/47898 ZFN pair. Administration of the 47171/47898 ZFN pair lead to gene modification levels of 16.9% and 25.4% indels for 100K and 600K MOI dose levels, respectively, while the 71557/71728 ZFN pair yielded 35.1% and 44.2% indels, respectively. At 10 days, the 71557/71728 ZFN pair activity was 2.1- and 1.7-fold higher than 47171/47898 ZFN pair activity for the low and high dose groups, respectively. As the entire dose-response curves were not achieved during the 10-day cell culture experiment, it was not possible to calculate and compare true EC50 values. The results above, however, provide a reasonable estimation of approximate 2-fold increase in ZFN activity over 10 days with the 2nd generation ZFNs.

Evaluation studies were also carried out in human primary hepatocytes to characterize any off-target cleavage events related to the second generation ZFN pair. Off target cleavage was determined by previously disclosed methods (see PCT Publication WO2018039440). Genomic DNA was extracted using QuickExtract™ DNA Extraction Solution (Lucigen) following manufactures conditions.

Figure 3H:
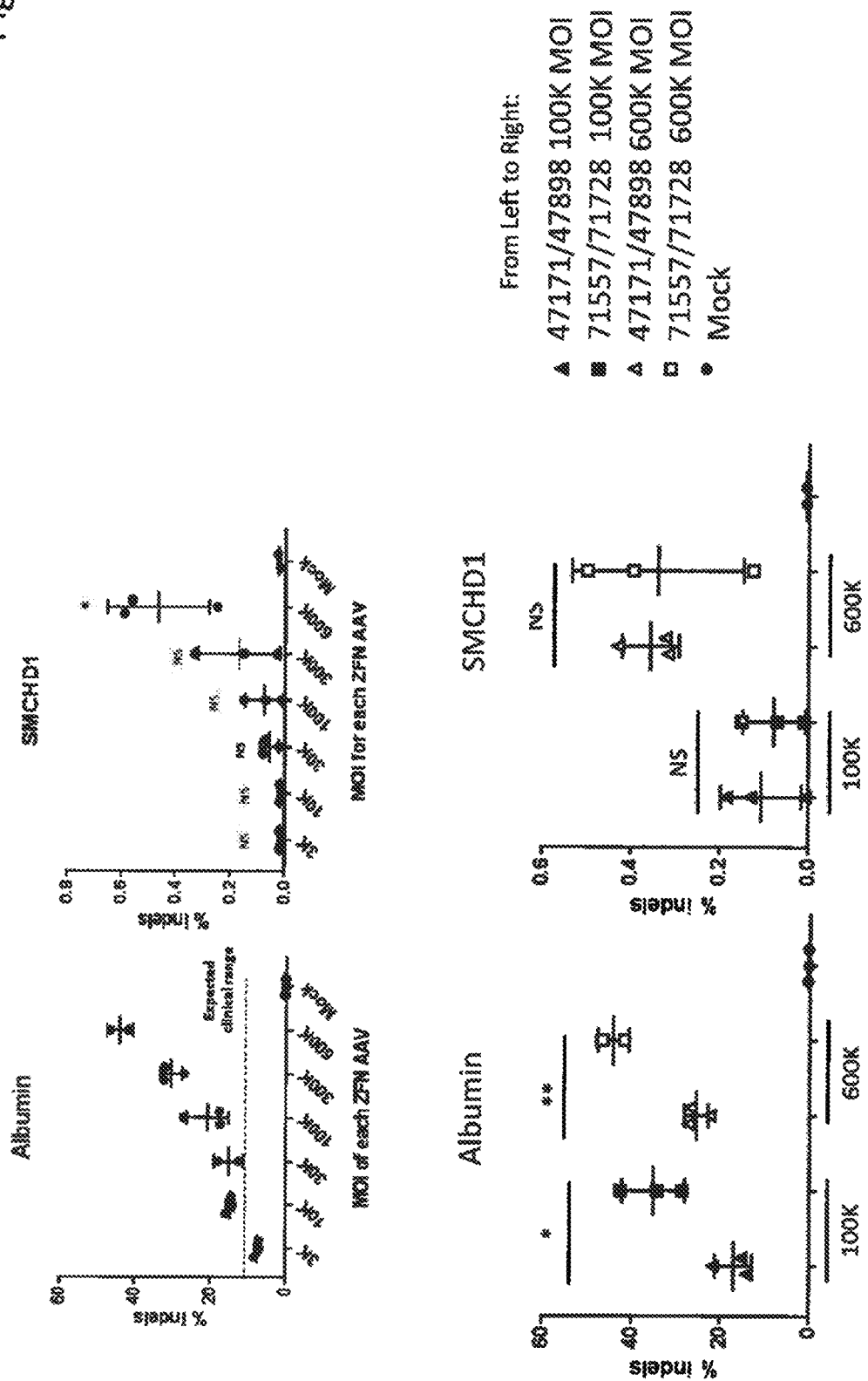

SMCHD1 has been identified as a detected off-target site for the ZFNs. Human primary hepatocytes transduced with AAV2/6 encoding the 47171/47898 or 71557/71728 ZFN pairs were evaluated by MiSeq deep sequencing. Human primary hepatocytes were treated with AAV comprising the second generation ZFN pair at the following MOI: 3K, 10K, 30K, 100K, 300K, 600K and Mock for 10 days. A dose response was observed with respect to ZFN modification at the on-target albumin site. Mean % indels at the albumin locus on Day 10 were 0.16, 7, 15, 15, 21, 30 and 44% following treatment with the 71557/71728 ZFN pair (see FIG. 3H, top row). NS—not statistically significant by two tailed t-test, * −p-value<0.05 by two tailed t-test. At the 100K MOI dose, the 47171/47898 ZFNs showed mean on-target activity of 17% indels and off-target activity of 0.11% indels (17/0.11 ratio=154); and the 71557/71728 ZFNs showed mean on-target activity of 35% and off-target activity of 0.08% (35/0.08 ratio=438). Comparing the two ratios, 2nd generation ZFNs are ~2.8-fold more selective than 1st generation ZFNs. At the 600K MOI dose, the 47171/47898 ZFNs showed mean on-target activity of 25% indels and off-target activity of 0.36% indels (25/0.36 ratio=69); and the 71557/71728 ZFNs showed mean on-target activity of 44% and off-target activity of 0.34% (44/0.34 ratio=130). Comparing the two ratios, 2nd generation ZFNs are ~1.9-fold more selective than first generation ZFNs. At the 100 K and 600K MOI, % indels for the 1st and 2nd generations ZFNs are 17% and 35%, and 25% and 44%, respectively, indicating that 2nd generation ZFN (ZFN 2.0) is ~2-fold more potent than the 1st generation ZFNs (see FIG. 3H).

In cells treated with the 1st generation left ZFN (47171), ZFN activity at the SNP-containing allele was only 39-44% as high as activity at the wild type allele. In comparison, in cells treated with the 2nd generation left ZFN (71557), ZFN activity at the SNP-containing allele was 91-108% as high as activity at the wild type allele.

Example 3

Use of a Polycationic Peptide Tag Increases ZFN Activity

The ZFNs including a polycationic peptide tag were examined for cleavage activity. The peptide used was the 3× Flag Tag (see PCT Publication No. WO2001027293), comprising the amino acid sequence Nterm—DYKDHDG-DYKDHDI-DYKDDDDK (SEQ ID NO:71). The sequence encoding the 3× Flag Tag is fused to the ZFN fusion protein at the N-terminus of the protein (see, Table 1).

ZFNs for this study were made against 7 ultra-conserved DNA targets that are conserved between mouse, NHP and human (see Bejerano et al (2004) Science 302(5675):1321-1325) to control for the cellular origin of the cells being tested. 74 ZFN pairs were made against the ultra-conserved DNA targets and were tested for activity in K562 cells either with or without the 3× Flag tag.

Figures 4A, 4B:
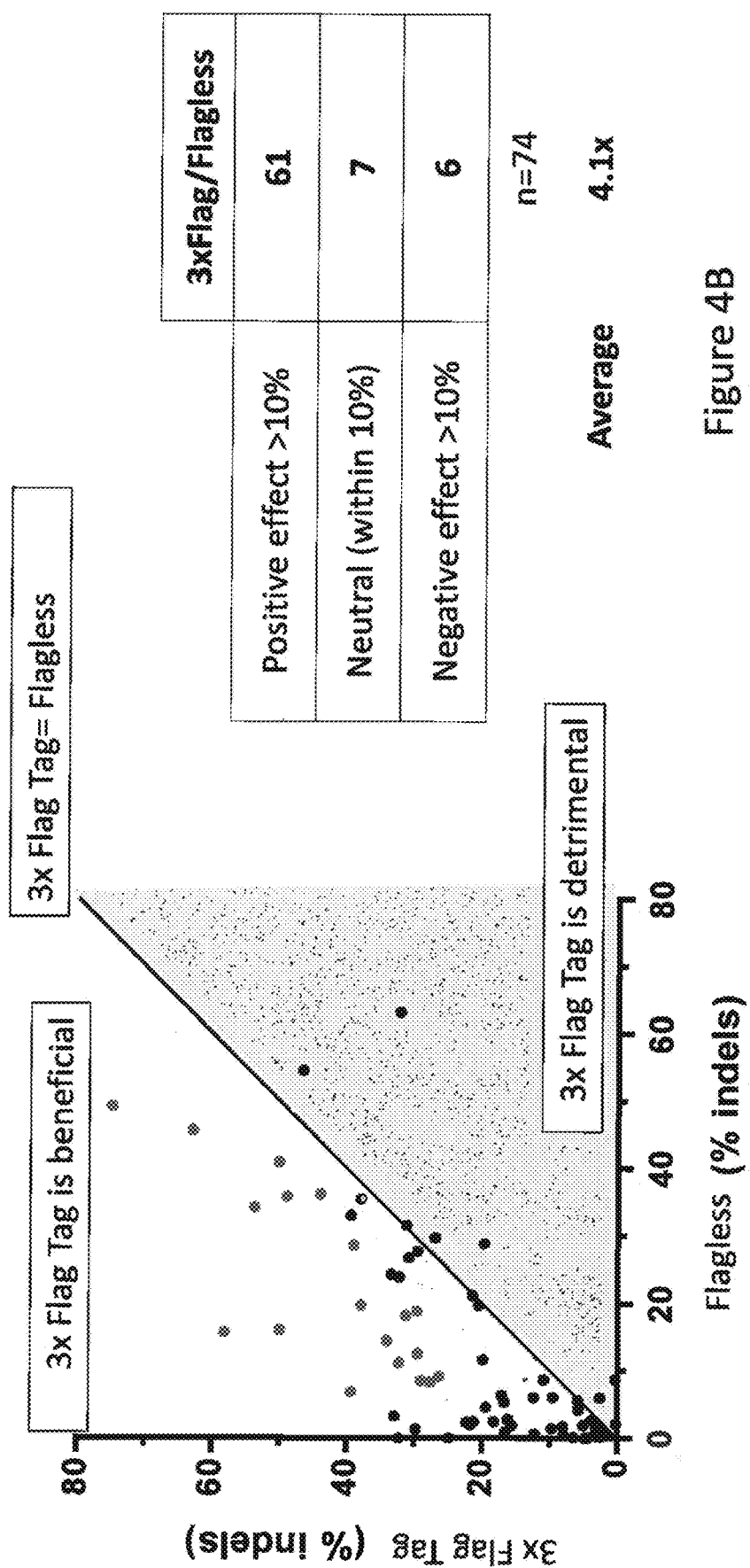
FIGS. 4A through 4C show increased nuclease activity (% indels, as determined by next generation sequencing) when the nucleases are expressed from polynucleotides further comprising one or more FLAG sequences.
Figure 4C:
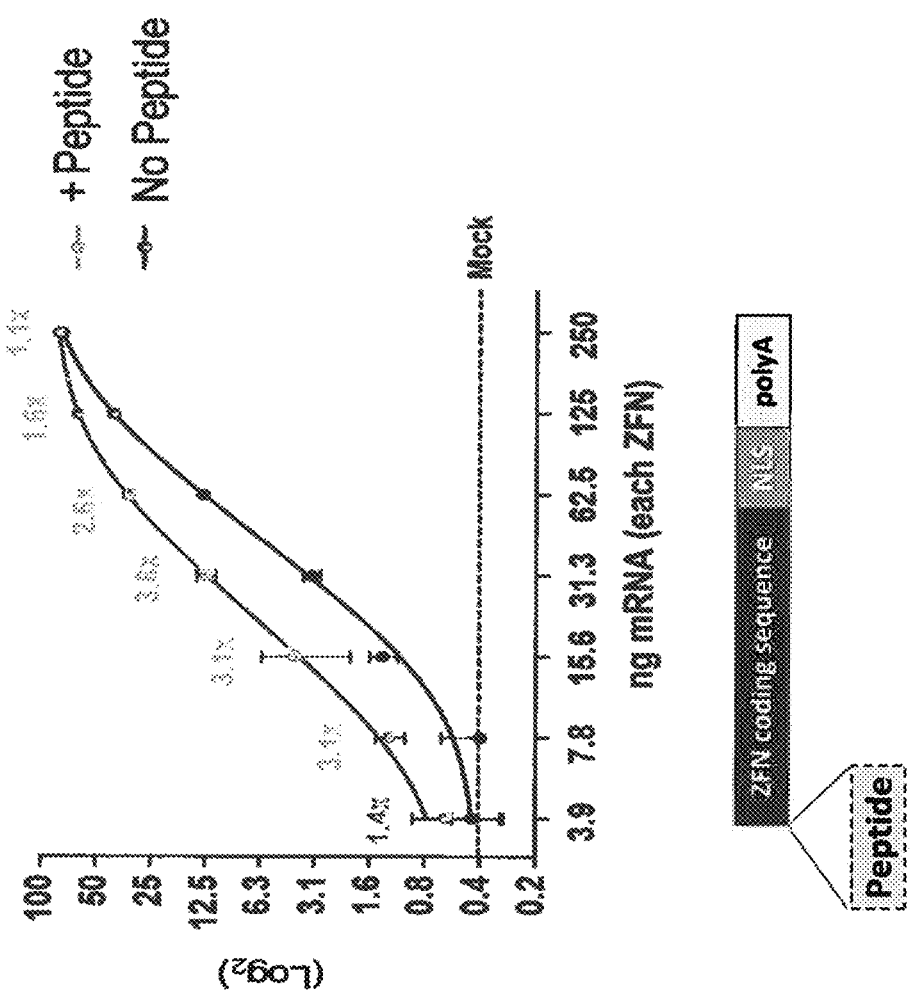

The results (FIG. 4A) demonstrate that the presence of the polycationic 3× Flag tag was very beneficial for ZFN cleavage activity (as determined by Cell assay to measure % indels), and in these ZFN pairs comprising the 3× Flag Tag, activity was increased by an average of 4.1× as compared to the ZFNs lacking the Flag Tag (FIG. 4B). As shown in FIG. 4C, addition of the 3× Flag Tag led to a 2-3× increase in ZFN activity.

Example 4

Addition of a WPRE Regulatory Element

Figure 5B:
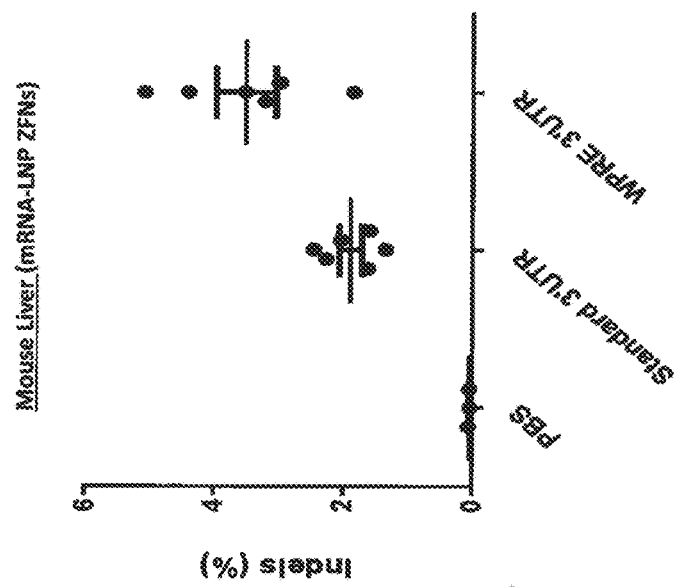
Figure 5C:
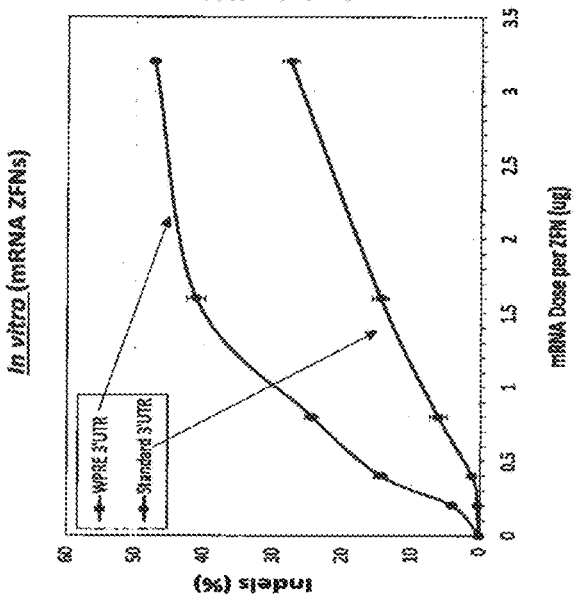

WPRE has been found to increase the activity of ZFNs, both in vitro (FIG. 5A, see U.S. Patent Publication 2016-0326548) and in vivo after delivery by LNPs (FIG. 5B, see U.S. Patent Publication No. US-2018-0185516-A1) or by AAV (FIG. 5C, see U.S. Patent Publication 2016-0326548).

In its natural form WPRE contains a partial open reading frame (ORF) for the WHV-X protein. The fully expressed WHV-X protein in the context of other viral elements like the WHV (We2) enhancer has been associated with a higher risk of hepatocarcinoma in woodchucks and mice (Hohne et. al (1990) EMBO J 9(4):1137-45; Flajolet et. al (1998) J Virol 72(7):6175-80). The WHV-X protein does not appear to be directly oncogenic, but some studies suggest that under certain circumstances it can act as a weak cofactor for the generation of liver cancers associated with infection by hepadnaviruses (hepatitis B virus for man; woodchuck hepatitis virus for woodchucks). The WPRE sequence used contains a partial open reading frame for WHV-X protein, but does not contain the We2 enhancer, which is thought to amplify expression of the WHV-X protein. Further, the WPRE sequence is placed 3' of the stop codon and out of frame with promoter and therapeutic transgene; thus no translation of this sequence is expected even if stop codon read-through occurred.

Figure 7A:
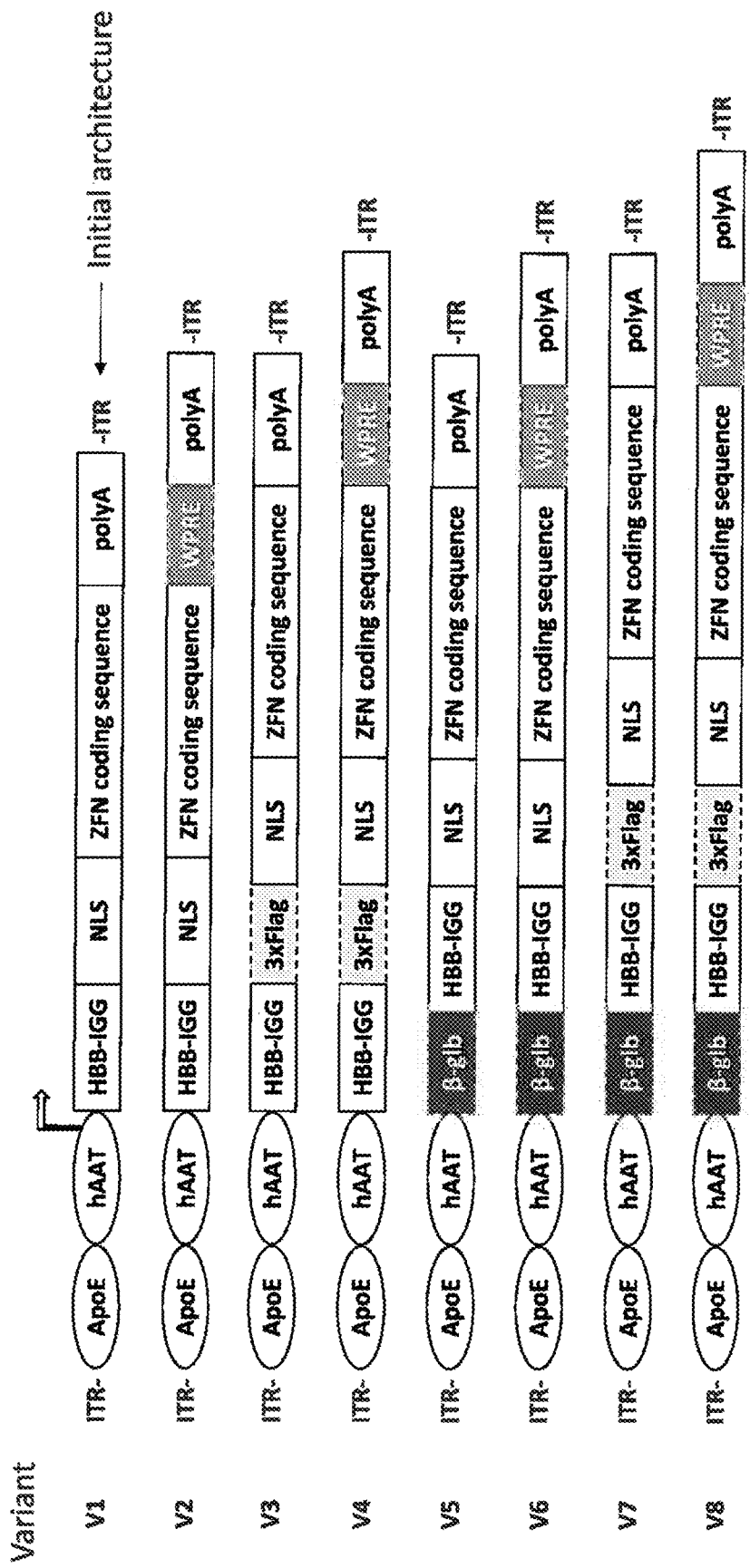
FIGS. 7A and 7B are illustrations of exemplary different variant constructs made and tested.

Thus, the WPRE element was added to the polynucleotides described herein, typically 3' to the nuclease coding sequence (FIG. 7). The WPRE element that is used can be WPREmut6 (Zanta-Boussif, ibid), derived from the J02442 variant, shown below:

J02442 WPREmut6:

(SEQ ID NO: 42)
5' AATCAACCTCTGGATTACAAAATTTGTGAAAGATTGACTGATATTCTT
AACTATGTTGCTCCTTTTACGCTGTGTGGATATGCTGCTTTAATGCCTCTG
TATCATGCTATTGCTTCCCGTACGGCTTTCGTTTTCTCCTCCTTGTATAAA
TCCTGGTTGCTGTCTCTTTATGAGGAGTTGTGGCCCGTTGTCCGTCAACGT
GGCGTGGTGTGCTCTGTGTTTGCTGACGCAACCCCACTGGCTGGGGCATT
GCCACCACCTGTCAACTCCTTTCTGGGACTTTCGCTTTCCCCCTCCCGATC
GCCACGGCAGAACTCATCGCCGCCTGCCTTGCCCGCTGCTGGACAGGGGCT
AGGTTGCTGGGCACTGATAATTCCGTGGTGTTGTCGGGGAAATCATCGTCC
TTTCCTTGGCTGCTCGCCTGTGTTGCCAACTGGATCCTGCGCGGGACGTCC
TTCTGCTACGTCCCTTCGGCTCTCAATCCAGCGGACCTCCCTTCCCGAGGC
CTTCTGCCGGTTCTGCGGCCTCTCCCGCGTCTTCGCTTTCGGCCTCCGACG
AGTCGGATCTCCCTTTGGGCCGCCTCCCCGCCTG.

In some embodiments, the WPRE elements is a truncated construct comprising only the gamma and alpha elements. The sequence of WPRE3 is shown below:

WPRE3:

(SEQ ID NO: 68)
GATAATCAACCTCTGGATTACAAAATTTGTGAAAGATTGACTGGTATTCTT
AACTATGTTGCTCCTTTTACGCTATGTGGATACGCTGCTTTAATGCCTTTG
TATCATGCTATTGCTTCCCGTATGGCTTTCATTTTCTCCTCCTTGTATAAA
TCCTGGTTAGTTCTTGCCACGGCGGAACTCATCGCCGCCTGCCTTGCCCGC
TGCTGGACAGGGGCTCGGCTGTTGGGCACTGACAATTCCGTGG.

In some embodiments, the J04514.1 variant is used and the mut6 variants are added into the sequence, as shown below:

J04514.1 WPREmut6:

(SEQ ID NO: 69)
AATCAACCTCTGGATTACAAAATTTGTGAAAGATTGACTGGTATTCTTAA
CTATGTTGCTCCTTTTACGCTATGTGGATACGCTGCTTTAATGCCTTTGT
ATCATGCTATTGCTTCCCGTATGGCTTTCATTTTCTCCTCCTTGTATAAA
TCCTGGTTGCTGTCTCTTTATGAGGAGTTGTGGCCCGTTGTCAGGCAACG
TGGCGTGGTGTGCACTGTGTTTGCTGACGCAACCCCACTGGTTGGGGCA
TTGCCACCACCTGTCAGCTCCTTTCCGGGACTTTCGCTTTCCCCCTCCCT
ATTGCCACGGCGGAACTCATCGCCGCCTGCCTTGCCCGCTGCTGGACAGG
GGCTCGGCTGTTGGGCACTGACAATTCCGTGGTGTTGTCGGGGAAATCAT
CGTCCTTTCCTTGGCTGCTCGCCTGTGTTGCCACCTGGATTCTGCGCGGG
ACGTCCTTCTGCTACGTCCCTTCGGCCCTCAATCCAGCGGACCTTCCTTC
CCGCGGCCTGCTGCCGGCTCTGCGGCCTCTTCCGCGTCTTCGCCTTCGCC
CTCAGACGAGTCGGATCTCCCTTTGGGCCGCCTCCCCGCCTG

All three of the WPRE variants lack the ability to express the WHV X gene, and may be used interchangeably in the expression constructs described herein.

Example 5

Addition of a 5' UTR

In 1994, Krieg and Melton (*Nucl. Acid. Res* 12(18):7057) described the 5' untranslated region of the *Xenopus* beta-globin gene and recognized its potential as an mRNA stabilizing sequence. Thus, the sequence for this element ([TG]CTTGTTCTTTTTGCAGAAGCTCAGAATAAACGCTCAACTTTGGCAGAT (SEQ ID NO:1), wherein TG is optional abbreviated βglb) was tested in the 5' untranslated region of the nuclease-encoding expression cassette. Constructs were tested in K562 cells as described above except that cells were assayed at 24 hours post transfection.

Figure 9:
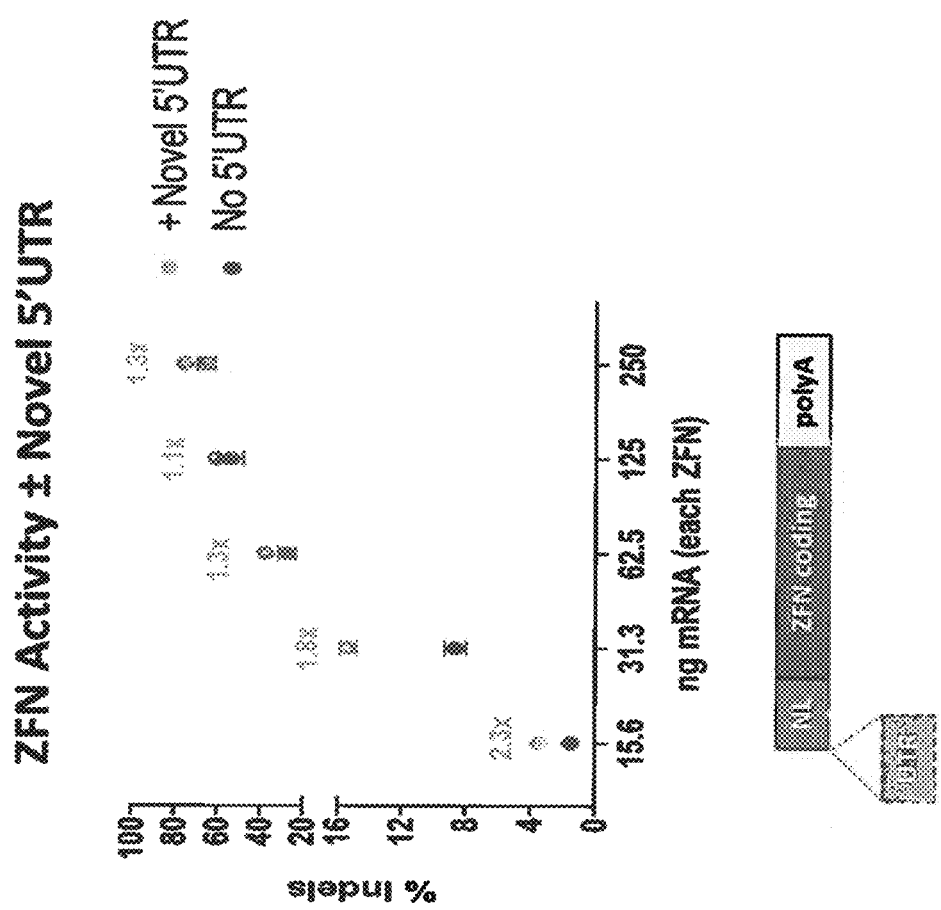
FIG. 9 is a graph showing nuclease activity (% indels, as determined by deep sequencing) in K562 cells transfected at the indicated mRNA amounts with mRNA encoding albumin-targeting ZFNs with (light shaded circles shown as "+Novel 5' UTR") or without (dark shaded circles shown as "No 5'UTR") a 5'UTR sequence (Xenopus β-globin UTR as shown in SEQ ID NO:1). Cells were assessed for ZFN activity 24 hours after transfection. The numbers above the light shaded circles (mRNA including the 5'UTR) indicate the fold increase as compared to mRNA without the 5'UTR.

As shown in FIG. 9, addition of a novel 5'UTR led to 2-3× increase in ZFN activity.

Example 6

Combinations of Enhancements

ZFNs including a 3× Flag tag ("3× Flag"), a *Xenopus* β-glb ("XBG") and/or a WPRE element were tried in various combinations in iPSC derived human hepatocytes. The ZFNs used were 42877/47931 and they were delivered via AAV6. The cells were harvested 6 days post transduction and activity measured against the albumin target.

Figure 6:
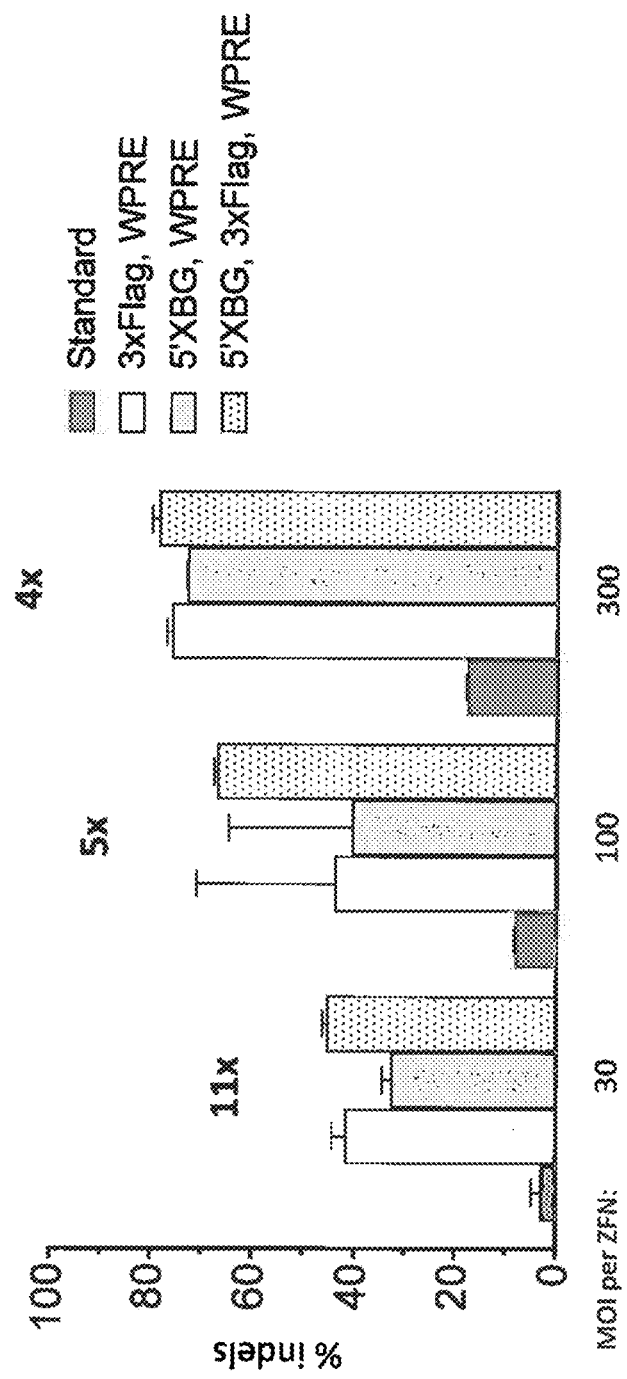
FIG. 6 is a graph showing increased nuclease activity (% indels, as determined by next generation sequencing) using the indicated combinations of polynucleotide components at the indicated MOIs. The left-most bar ("standard") under each condition shows results where the nuclease-encoding polynucleotide did not include 3× FLAG, a WPRE sequence or a poly A sequence. The bar second from the left ("3× Flag, WPRE") shows results where the nuclease-encoding polynucleotide included a 3× FLAG peptide sequence and a WPRE sequence. The bar second from the right ("5'XBG, WPRE") shows results where the nuclease-encoding polynucleotide included a bovine growth hormone ("BG") poly A sequence and a WPRE sequence. The right-most bar ("SXBG, 3× FLAG, WPRE") shows results where the nuclease-encoding polynucleotide included a BG poly A sequence, a 3× FLAG peptide sequence and a WPRE sequence. Shown above each condition (MOI) is the fold increase in nuclease activity observed.

The results demonstrated that enhancement of ZFN activity in the presence of all three elements in comparison with the initial vector (see FIG. 6).

Further, a series of 8 expression constructs were thus constructed including the ZFN without or with various combinations all the different elements described above (see FIG. 7A showing variants V1 through V8). All variants were used in an AAV 6 vector and used with an ApoE-hAAT promoter (Okuyama et al (1996) *Hum Gene Ther* 7(5):637-45). These vectors also comprised a human beta-globin-immunoglobulin chimeric intron sequence described as a chimeric intron composed of the 5'-donor site from the first intron of the human β-globin gene and the branch and 3'-acceptor site from the intron of an immunoglobulin gene heavy chain variable region (Promega). The NLS used in these constructs was from SV40.

The vectors were then tested for cleavage activity of the delivered ZFN pair (42877/47931) where both ZFNs were delivered in the same variant architecture.

Figure 8:
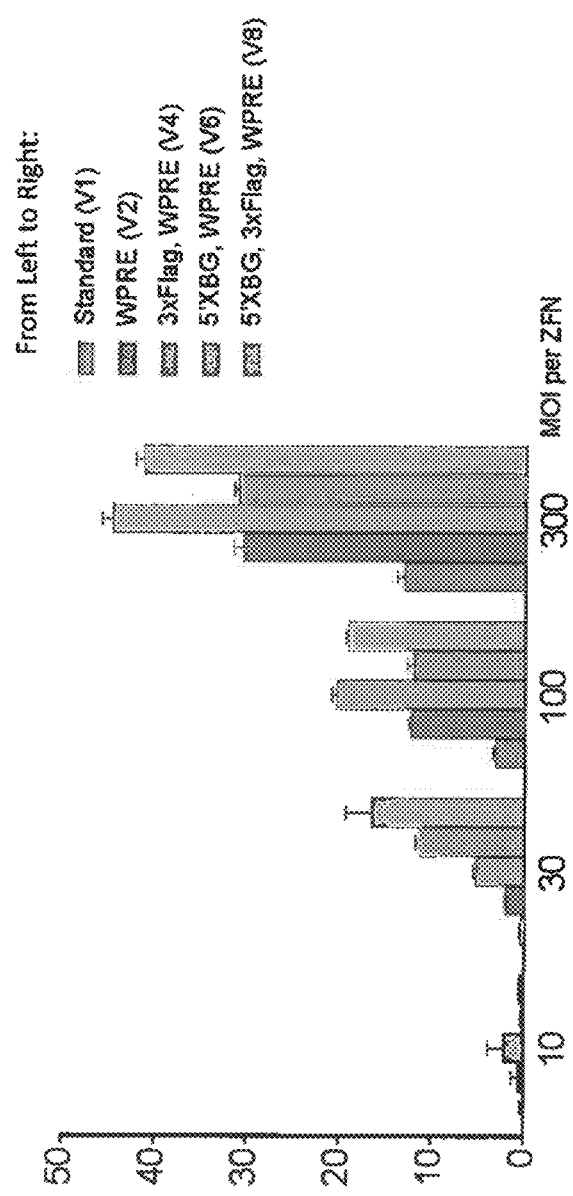
FIG. 8 is a graph showing nuclease activity (% indels, as determined by next generation sequencing) using the indicated combinations of polynucleotide components at the indicated MOIs. The left-most bar ("standard (V1)") under each condition shows results where the nuclease-encoding polynucleotide did not include 3× FLAG, a WPRE sequence or a poly A sequence, also referred to as a variant 1 (V1) or parent. The bar second from the left ("WPRE (V2)") shows results where the nuclease-encoding polynucleotide included a WPRE sequence. The middle bar ("3× Flag, WPRE (V4)") shows results with a variant (designated V4) that included a 3× FLAG sequence and a WPRE sequence. The bar second from the right ("5'XBG, WPRE (V6)") shows results where the nuclease-encoding polynucleotide (designated variant 6 or V6) included a bovine growth hormone ("BG") poly A sequence and a WPRE sequence. The right-most bar ("SXBG, 3× FLAG, WPRE") shows results where the nuclease-encoding polynucleotide (designated variant 8 or V8) that included a BG poly A sequence, a 3× FLAG peptide sequence and a WPRE sequence.

As shown in FIG. 8, two of the variant architectures, Variant 4 and Variant 8, both of which included FLAG sequences (Table 1), provided superior results as compared to the other variants, including vector architecture currently in use. These experiments were carried out in HepG2 cells using 300,000 MOI of AAV comprising the different vectors.

Figure 7B:
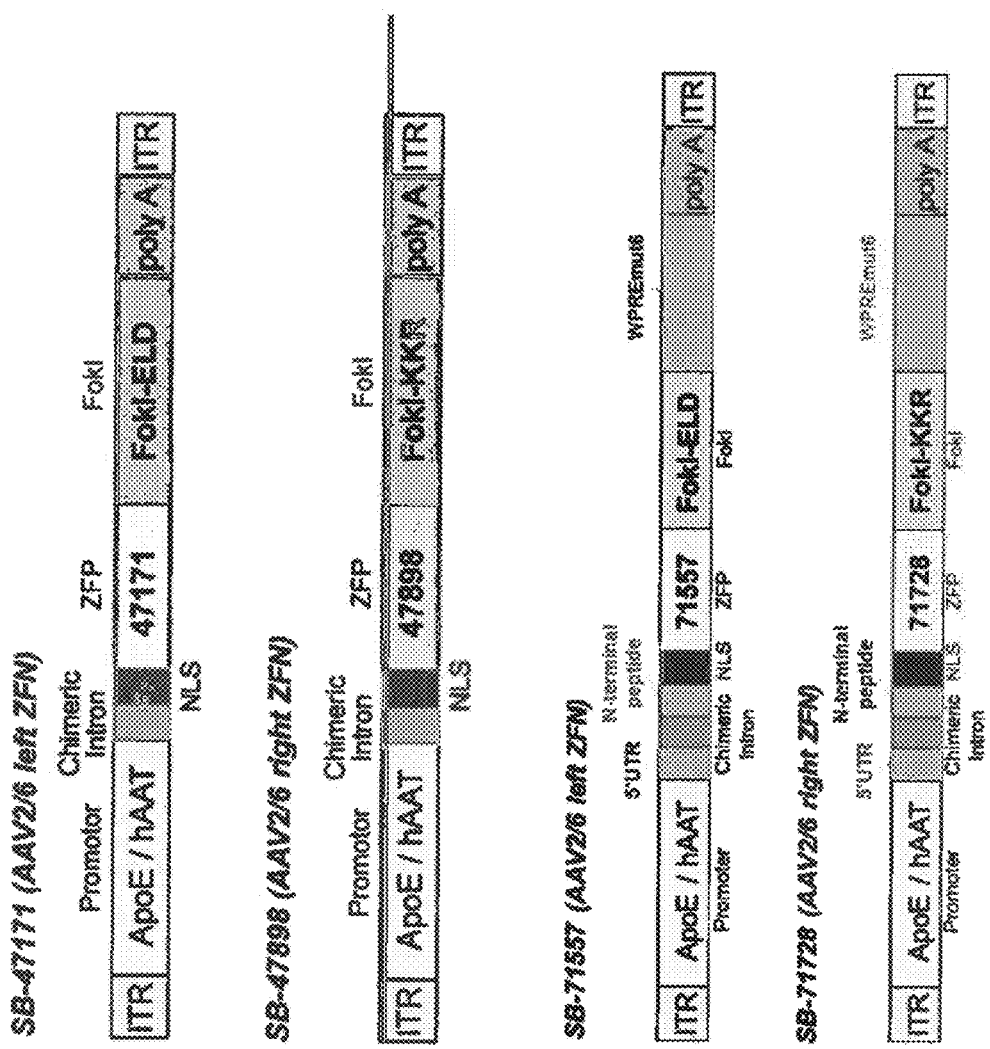

One albumin-specific ZFN pair made comprising a combination of the various enhancements is the 71557/71728 pair as described above. FIG. 7B depicts a schematic of the AAVs that encode these ZFNs. The elements of the pair are shown in the tables and sequences below. It will be apparent that any of the elements may be substitute with analogous sequences, for example a WPRE sequence known in the art or as shown in Example 4 above in place of the WPRE sequence below.

TABLE 4

| Elements of SB71557AAV (SEQ ID NO:43) | | | |
|---|---|---|---|
| Nucleotide Position-annotation | Feature/ Description | SEQ ID NO: | Sequence |
| I-130 | 5' ITR [plain text in brackets] | 44 | CTGCGCGCTCGCTCGCTCACTGAGGCCGCCCGGGCAAAGCCCGGG CGTCGGGCGACCTTTGGTCGCCCGGCCTCAGTGAGCGAGCGAGCG CGCAGAGAGGGAGTGGCCAACTCCATCACTAGGGGTTCCT |
| 156-476 | ApoE (Enhancer) underlined | 45 | AGGCTCAGAGGCACACAGGAGTTTCTGGGCTCACCCTGCCCCCTT CCAACCCCTCAGTTCCCATCCTCCAGCAGCTGTTTGTGTGCTGCC TCTGAAGTCCACACTGAACAAACTTCAGCCTACTCATGTCCCTAA AATGGGCAAACATTGCAAGCAGCAAACAGCAAACACACAGCCCTC CCTGCCTGCTGACCTTGGAGCTGGGGCAGAGGTCAGAGACCTCTC TGGGCCCATGCCACCTCCAACATCCACTCGACCCCTTGGAATTTC GGTGGAGAGGAGCAGAGGTTGTCCTGGCGTGGTTTAGGTAGTGTG AGAGGG |
| 485-877 | hAAT (Promoter) *italics* | 46 | GATCTTGCTACCAGTGGAACAGCCACTAAGGATTCTGCAGTGAGA GCAGAGGGCCAGCTAAGTGGTACTCTCCCAGAGACTGTCTGACTC ACGCCACCCCCTCCACCTTGGACACAGGACGCTGTGGTTTCTGAG CCAGGTACAATGACTCCTTTCGGTAAGTGCAGTGGAAGCTGTACA CTGCCCAGGCAAAGCGTCCGGGCAGCGTAGGCGGGCGACTCAGAT CCCAGCCAGTGGACTTAGCCCCTGTTTGCTCCTCCGATAACTGGG GTGACCTTGGTTAATATTCACCAGCAGCCTCCCCCGTTGCCCCTC TGGATCCACTGCTTAAATACGGACGAGGACAGGGCCCTGTCTCCT CAGCTTCAGGCACCACCACTGACCTGGGACAGT |
| 886-933 | 5' UTR Bold | 47 | CTTGTTCTTTTTGCAGAAGCTCAGAATAAACGCTCAACTTTGGCA GAT |
| 943-1075 | Human β globin/ IgG chimeric intron (Intron) double underlined | 48 | GTAAGTATCAAGGTTACAAGACAGGTTTAAGGAGACCAATAGAAA CTGGGCTTGTCGAGACAGAGAAGACTCTTGCGTTTCTGATAGGCA CCTATTGGTCTTACTGACATCCACTTTGCCTTTCTCTCCACAG |

TABLE 4-continued

Elements of SB71557AAV (SEQ ID NO:43)

| 1086-1154 | N-terminal peptide | 49 | GACTACAAAGACCATGACGGTGATTATAAAGATCATGACATCGAT<br>TACAAGGATGACGATGACAAG |
|---|---|---|---|
| 1161-1181 | Nuclear localization signal Bold italic | 50 | CCAAGAAGAAGAGGAAGGTC |
| 1200-1631 | ZFP 71557 DNA-binding domain lower case | 51 | GCCGCTATGGCTGAGAGGCCCTTCCAGTGTCGAATCTGCATGCAG<br>AACTTCAGTCAGTCCGGCAACCTGGCCCGCCACATCCGCACCCAC<br>ACCGGCGAGAAGCCTTTTGCCTGTGACATTTGTGGGAGGAAATTT<br>GCCCTGAAGCAGAACCTGTGTATGCATACCAAGATACACACGGGC<br>GAGAAGCCCTTCCAGTGTCGAATCTGCATGCAGAAGTTTGCCTGG<br>CAGTCCAACCTGCAGAACCATACCAAGATACACACGGGCGAGAAG<br>CCCTTCCAGTGTCGAATCTGCATGCGTAACTTCAGTACCTCCGGC<br>AACCTGACCCGCCACATCCGCACCCACACCGGCGAGAAGCCTTTT<br>GCCTGTGACATTTGTGGGAGGAAATTTGCCCGCCGCTCCCACCTG<br>ACCTCCCATACCAAGATACACCTGCGG |
| 1638-2237 | FokI-ELD nuclease domain Dashed underlined | 52 | CAGCTGGTGAAGAGCGAGCTGGAGGAGAAGAAGTCCGAGCTGCGG<br>CACAAGCTGAAGTACGTGCCCCACGAGTACATCGAGCTGATCGAG<br>ATCGCCAGGAACAGCACCCAGGACCGCATCCTGGAGATGAAGGTG<br>ATGGAGTTCTTCATGAAGGTGTACGGCTACAGGGGAAAGCACCTG<br>GGCGGAAGCAGAAAGCCTGACGGCGCCATCTATACAGTGGGCAGC<br>CCCATCGATTACGGCGTGATCGTGGACACAAAGGCCTACAGCGGC<br>GGCTACAATCTGCCTATCGGCCAGGCCGACGAGATGGAGAGATAC<br>GTGGAGGAGAACCAGACCCGGGATAAGCACCTCAACCCCAACGAG<br>TGGTGGAAGGTGTACCCTAGCAGCGTGACCGAGTTCAAGTTCCTG<br>TTCGTGAGCGGCCACTTCAAGGGCAACTACAAGGCCCAGCTGACC<br>AGGCTGAACCACATCACCAACTGCGACGGCGCCGTGCTGAGCGTG<br>GAGGAGCTGCTGATCGGCGGCGAGATGATCAAAGCCGGCACCCTG<br>ACACTGGAGGAGGTGCGGCGCAAGTTCAACAACGGCGAGATCAAC<br>TTCAGATCTTGATAA |
| 2250-2841 | WPREmut6 3' UTR Dotted underlined | 53 | AATCAACCTCTGGATTACAAAATTTGTGAAAGATTGACTGATATT<br>CTTAACTATGTTGCTCCTTTTACGCTGTGTGGATATGCTTTA<br>ATGCCTCTGTATCATGCTATTGCTTCCCGTACGGCTTTCGTTTTC<br>TCCTCCTTGTATAAATCCTGGTTGCTGTCTCTTTATGAGGAGTTG<br>TGGCCCGTTGTCCGTCAACGTGGCGTGGTGTGCTCTGTGTTTGCT<br>GACGCAACCCCCACTGGCTGGGGCATTGCCACCACCTGTCAACTC<br>CTTTCTGGGACTTTCGCTTTCCCCCTCCCGATCGCCACGGCAGAA<br>CTCATCGCCGCCTGCCTTGCCCGCTGCTGGACAGGGGCTAGGTTG<br>CTGGGCACTGATAATTCCGTGGTGTTGTCGGGGAAATCATCGTCC<br>TTTCCTTGGCTGCTCGCCTGTGTTGCCAACTGGATCCTGCGCGGG<br>ACGTCCTTCTGCTACGTCCCTTCGGCTCTCAATCCAGCGGACCTC<br>CCTTCCCGAGGCCTTCTGCCGGTTCTGCGGCCTCTCCCGCGTCTT<br>CGCTTTCGGCCTCCGACGAGTCGGATCTCCCTTTGGGCCGCCTCC<br>CCGCCTG |
| 2848-3070 | Polyadenylation signal | 54 | CTGTGCCTTCTAGTTGCCAGCCATCTGTTGTTTGCCCCTCCCCCG<br>TGCCTTCCTTGACCCTGGAAGGTGCCACTCCCACTGTCCTTTCCT<br>AATAAAATGAGGAAATTGCATCGCATTGTCTGAGTAGGTGTCATT<br>CTATTCTGGGGGGTGGGGTGGGGCAGGACAGCAAGGGGGAGGATT<br>GGGAAGACAATAGCAGGCATGCTGGGGATGCGGTGGGCTCTAT |
| 3088-3195 | 3' ITR [Bold text in brackets] | 55 | AGGAACCCCTAGTGATGGAGTTGGCCACTCCCTCTCTGCGCGCTC<br>GCTCGCTCACTGAGGCCGCCCGGGCTTTGCCCGGGCGGCCTCAGT<br>GAGCGAGCGAGCGCGCAG |

Complete Sequence of 71557 AAV:

(SEQ ID NO: 43)

[CTGCGCGCTC GCTCGCTCAC TGAGGCCGCC CGGGCAAAGC CCGGGCGTCG     50

GGCGACCTTT GGTCGCCCGG CCTCAGTGAG CGAGCGAGCG CGCAGAGAGG     100

GAGTGGCCAA CTCCATCACT AGGGGTTCCT] GCGGCCTAAG CTTGAGCTCT    150

TCGAAAGGCT CAGAGGCACA CAGGAGTTTC TGGGCTCACC CTGCCCCCTT    200

TABLE 4-continued

Elements of SB71557AAV (SEQ ID NO:43)

CCAACCCCTC AGTTCCCATC CTCCAGCAGC TGTTTGTGTG CTGCCTCTGA  250

AGTCCACACT GAACAAACTT CAGCCTACTC ATGTCCCTAA AATGGGCAAA  300

CATTGCAAGC AGCAAACAGC AAACACACAG CCCTCCCTGC CTGCTGACCT  350

TGGAGCTGGG GCAGAGGTCA GAGACCTCTC TGGGCCCATG CCACCTCCAA  400

CATCCACTCG ACCCCTTGGA ATTTCGGTGG AGAGGAGCAG AGGTTGTCCT  450

GGCGTGGTTT AGGTAGTGTG AGAGGGGTCC CGGGGATCTT *GCTACCAGTG*  500

*GAACAGCCAC TAAGGATTCT GCAGTGAGAG CAGAGGGCCA GCTAAGTGGT*  550

*ACTCTCCCAG AGACTGTCTG ACTCACGCCA CCCCCTCCAC CTTGGACACA*  600

*GGACGCTGTG GTTTCTGAGC CAGGTACAAT GACTCCTTTC GGTAAGTGCA*  650

*GTGGAAGCTG TACACTGCCC AGGCAAAGCG TCCGGGCAGC GTAGGCGGGC*  700

*GACTCAGATC CCAGCCAGTG GACTTAGCCC CTGTTTGCTC CTCCGATAAC*  750

*TGGGGTGACC TTGGTTAATA TTCACCAGCA GCCTCCCCCG TTGCCCCTCT*  800

*GGATCCACTG CTTAAATACG GACGAGGACA GGGCCCTGTC TCCTCAGCTT*  850

*CAGGCACCAC CACTGACCTG GGACAGTCCT AGGTG*CTTGT TCTTTTTGCA  900

GAAGCTCAGA ATAAACGCTC AACTTTGGCA GATACTAGTC AGGTAAGTAT  950

CAAGGTTACA AGACAGGTTT AAGGAGACCA ATAGAAACTG GCTTGTCGA  1000

GACAGAGAAG ACTCTTGCGT TTCTGATAGG CACCTATTGG TCTTACTGAC  1050

ATCCACTTTG CCTTTCTCTC CACAGGACCG GTGCCATGGA CTACAAAGAC  1100

CATGACGGTG ATTATAAAGA TCATGACATC GATTACAAGG ATGACGATGA  1150

CAAGATGGCC *CCCAAGAAGA AGAGGAAGGT C*GGCATTCAT GGGTACCCg  1200 ccgctatggc tgagaggccc ttccagtgtc gaatctgcat gcagaacttc  1250
agtcagtccg gcaacctggc ccgccacatc cgcacccaca ccggcgagaa  1300
gccttttgcc tgtgacattt gtgggaggaa atttgccctg aagcagaacc  1350
tgtgtatgca taccaagata cacacgggcg agaagccctt ccagtgtcga  1400
atctgcatgc agaagtttgc ctggcagtcc aacctgcaga accataccaa  1450
gatacacacg ggcgagaagc ccttccagtg tcgaatctgc atgcgtaact  1500
tcagtacctc cggcaacctg acccgccaca tccgcaccca caccggcgag  1550
aagccttttg cctgtgacat ttgtgggagg aaatttgccc gccgctccca  1600

TABLE 4-continued

Elements of SB71557AAV (SEQ ID NO:43)

| | |
|---|---|
| cctgacctcc cataccaaga tacacctgcg gGGATCCCAG CTGGTGAAGA | 1650 |
| GCGAGCTGGA GGAGAAGAAG TCCGAGCTGC GGCACAAGCT GAAGTACGTG | 1700 |
| CCCCACGAGT ACATCGAGCT GATCGAGATC GCCAGGAACA GCACCCAGGA | 1750 |
| CCGCATCCTG GAGATGAAGG TGATGGAGTT CTTCATGAAG GTGTACGGCT | 1800 |
| ACAGGGGAAA CGACCTGGGC GGAAGCAGAA AGCCTGACGG CGCCATCTAT | 1850 |
| ACAGTGGGCA GCCCCATCGA TTACGGCGTG ATCGTGGACA CAAAGGCCTA | 1900 |
| CAGCGGCGGC TACAATCTGC CTATCGGCCA GGCCGACGAG ATGGAGAGAT | 1950 |
| ACGTGGAGGA GAACCAGACC CGGGATAAGC ACCTCAACCC CAACGAGTGG | 2000 |
| TGGAAGGTGT ACCCTAGCAG CGTGACCGAG TTCAAGTTCC TGTTCGTGAG | 2050 |
| CGGCCACTTC AAGGGCAACT ACAAGGCCCA GCTGACCAGG CTGAACCACA | 2100 |
| TCACCAACTG CGACGGCGCC GTGCTGAGCG TGGAGGAGCT GCTGATCGGC | 2150 |
| GGCGAGATGA TCAAAGCCGG CACCCTGACA CTGGAGGAGG TGCGGCGCAA | 2200 |
| GTTCAACAAC GGCGAGATCA ACTTCAGATC TTGATAACTC GAGTCTAGAA | 2250 |
| ATCAACCTCT GGATTACAAA ATTTGTGAAA GATTGACTGA TATTCTTAAC | 2300 |
| TATGTTGCTC CTTTTACGCT GTGTGGATAT GCTGCTTTAA TGCCTCTGTA | 2350 |
| TCATGCTATT GCTTCCCGTA CGGCTTTCGT TTTCTCCTCC TTGTATAAAT | 2400 |
| CCTGGTTGCT GTCTCTTTAT GAGGAGTTGT GGCCCGTTGT CCGTCAACGT | 2450 |
| GGCGTGGTGT GCTCTGTGTT TGCTGACGCA ACCCCCACTG GCTGGGGCAT | 2500 |
| TGCCACCACC TGTCAACTCC TTTCTGGGAC TTTCGCTTTC CCCCTCCCGA | 2550 |
| TCGCCACGGC AGAACTCATC GCCGCCTGCC TTGCCCGCTG CTGGACAGGG | 2600 |
| GCTAGGTTGC TGGGCACTGA TAATTCCGTG GTGTTGTCGG GGAAATCATC | 2650 |
| GTCCTTTCCT TGGCTGCTCG CCTGTGTTGC CAACTGGATC CTGCGCGGGA | 2700 |
| CGTCCTTCTG CTACGTCCCT TCGGCTCTCA ATCCAGCGGA CCTCCCTTCC | 2750 |
| CGAGGCCTTC TGCCGGTTCT GCGGCCTCTC CCGCGTCTTC GCTTTCGGCC | 2800 |
| TCCGACGAGT CGGATCTCCC TTTGGGCCGC CTCCCCGCCT GGCTAGCCTG | 2850 |
| TGCCTTCTAG TTGCCAGCCA TCTGTTGTTT GCCCCTCCCC CGTGCCTTCC | 2900 |
| TTGACCCTGG AAGGTGCCAC TCCCACTGTC CTTTCCTAAT AAAATGAGGA | 2950 |
| AATTGCATCG CATTGTCTGA GTAGGTGTCA TTCTATTCTG GGGGGTGGGG | 3000 |
| TGGGGCAGGA CAGCAAGGGG GAGGATTGGG AAGACAATAG CAGGCATGCT | 3050 |

TABLE 4-continued

Elements of SB71557AAV (SEQ ID NO:43)

<u>GGGGATGCGG TGGGCTCTAT GCGGCCGCGT CGAGCGC</u>[AGG AACCCCTAGT      3100

GATGGAGTTG GCCACTCCCT CTCTGCGCGC TCGCTCGCTC ACTGAGGCCG      3150

CCCGGGCTTT GCCCGGGCGG CCTCAGTGAG CGAGCGAGCG CGCAG      3195

TABLE 5

Elements of SB71728 AAV (SEQ ID NO:56)

| Nucleotide Position-annotation | Feature/Description | SEQ ID NO: | Sequence |
|---|---|---|---|
| 1-130 | 5' ITR [plain text in brackets] | 44 | CTGCGCGCTCGCTCGCTCACTGAGGCCGCCCGGGCAAAGCCCGGGCGTCG GGCGACCTTTGGTCGCCCGGCCTCAGTGAGCGAGCGAGCGCGCAGAGAGG GAGTGGCCAACTCCATCACTAGGGGTTCCT |
| 156-476 | ApoE (Enhancer) <u>underlined</u> | 45 | AGGCTCAGAGGCACACAGGAGTTTCTGGGCTCACCCTGCCCCCTTCCAAC CCCTCAGTTCCCATCCTCCAGCAGCTGTTTGTGTGCTGCCTCTGAAGTCC ACACTGAACAAACTTCAGCCTACTCATGTCCCTAAAATGGGCAAACATTG CAAGCAGCAAACAGCAAACACACAGCCCTCCCTGCCTGCTGACCTTGGAG CTGGGGCAGAGGTCAGAGACCTCTCTGGGCCCATGCCACCTCCAACATCC ACTCGACCCCTTGGAATTTCGGTGGAGAGGAGCAGAGGTTGTCCTGGCGT GGTTTAGGTAGTGTGAGAGGG |
| 485-877 | hAAT (Promoter) *italics* | 46 | GATCTTGCTACCAGTGGAACAGCCACTAAGGATTCTGCAGTGAGAGCAGA GGGCCAGCTAAGTGGTACTCTCCCAGAGACTGTCTGACTCACGCCACCCC CTCCACCTTGGACACAGGACGCTGTGGTTTCTGAGCCAGGTACAATGACT CCTTTCGGTAAGTGCAGTGGAAGCTGTACACTGCCCAGGCAAAGCGTCCG GGCAGCGTAGGCGGGCGACTCAGATCCCAGCCAGTGGACTTAGCCCCTGT TTGCTCCTCCGATAACTGGGGTGACCTTGGTTAATATTCACCAGCAGCCT CCCCCGTTGCCCCTCTGGATCCACTGCTTAAATACGGACGAGGACAGGGC CCTGTCTCCTCAGCTTCAGGCACCACCACTGACCTGGGACAGT |
| 886-933 | 5' UTR Bold | 47 | CTTGTTCTTTTTGCAGAAGCTCAGAATAAACGCTCAACTTTGGCAGAT |
| 943-1075 | Human β globin/IgG chimeric intron (Intron) <u><u>double underlined</u></u> | 48 | GTAAGTATCAAGGTTACAAGACAGGTTTAAGGAGACCAATAGAAACTGGG CTTGTCGAGACAGAGAAGACTCTTGCGTTTCTGATAGGCACCTATTGGTC TTACTGACATCCACTTTGCCTTTCTCTCCACAG |
| 1086-1154 | N-terminal peptide | 49 | GACTACAAAGACCATGACGGTGATTATAAAGATCATGACATCGATTACAA GGATGACGATGACAAG |
| 1161-1181 | Nuclear localization signal *Bold italic* | 50 | CCCAAGAAGAAGAGGAAGGTC |
| 1200-1715 | ZFP 71728 DNA-binding domain lower case | 57 | GCCGCTATGGCTGAGAGGCCCTTCCAGTGTCGAATCTGCATGCGTAACTT CAGTCAGTCCTCCGACCTGTCCCGCCACATCCGCACCCACACCGGCGAGA AGCCTTTTGCCTGTGACATTTGTGGGAGGAAATTTGCCCTGAAGCACAAC CTGCTGACCCATACCAAGATACACACGGGCGAGAAGCCCTTCCAGTGTCG AATCTGCATGCAGAACTTCAGTGACCAGTCCAACCTGCGCGCCCACATCC GCACCCACACCGGCGAGAAGCCTTTTGCCTGTGACATTTGTGGGAGGAAA TTTGCCCGCAACTTCTCCCTGACCATGCATACCAAGATACACACCGGAGA GCGCGGCTTCCAGTGTCGAATCTGCATGCGTAACTTCAGTCTGCGCCACG ACCTGGAGCGCCACATCCGCACCCACACCGGCGAGAAGCCTTTTGCCTGT GACATTTGTGGGAGGAAATTTGCCCACCGCTCCAACCTGAACAAGCATAC CAAGATACACCTGCGG |

TABLE 5-continued

Elements of SB71728 AAV (SEQ ID NO:56)

| | | | |
|---|---|---|---|
| 1722-2315 | FokI-KKR nuclease domain<br>Dashed underlined | 58 | CAGCTGGTGAAGAGCGAGCTGGAGGAGAAGAAGTCCGAGCTGCGGCACAA<br>GCTGAAGTACGTGCCCCACGAGTACATCGAGCTGATCGAGATCGCCAGGA<br>ACAGCACCCAGGACCGCATCCTGGAGATGAAGGTGATGGAGTTCTTCATG<br>AAGGTGTACGGCTACAGGGGAAAGCACCTGGGCGGAAGCAGAAAGCCTGA<br>CGGCGCCATCTATACAGTGGGCAGCCCCATCGATTACGGCGTGATCGTGG<br>ACACAAAGGCCTACAGCGGCGGCTACAATCTGAGCATCGGCCAGGCCGAC<br>GAGATGCAGAGATACGTGAAGGAGAACCAGACCCGGAATAAGCACATCAA<br>CCCCAACGAGTGGTGGAAGGTGTACCCTAGCAGCGTGACCGAGTTCAAGT<br>TCCTGTTCGTGAGCGGCCACTTCAAGGGCAACTACAAGGCCCAGCTGACC<br>AGGCTGAACCGCAAAACCAACTGCAATGGCGCCGTGCTGAGCGTGGAGGA<br>GCTGCTGATCGGCGGCGAGATGATCAAAGCCGGCACCCTGACACTGGAGG<br>AGGTGCGGCGCAAGTTCAACAACGGCGAGATCAACTTCTGATAA |
| 2328-2919 | WPREmut6<br>3'UTR<br>Dotted underlined | 53 | AATCAACCTCTGGATTACAAAATTTGTGAAAGATTGACTGATATTCTTAA<br>CTATGTTGCTCCTTTTACGCTGTGTGGATATGCTGCTTTAATGCCTCTGT<br>ATCATGCTATTGCTTCCCGTACGGCTTTCGTTTTCTCCTCCTTGTATAAA<br>TCCTGGTTGCTGTCTCTTTATGAGGAGTTGTGGCCCGTTGTCCGTCAACG<br>TGGCGTGGTGTGCTCTGTGTTTGCTGACGCAACCCCCACTGGCTGGGGCA<br>TTGCCACCACCTGTCAACTCCTTTCTGGGACTTTCGCTTTCCCCCTCCCG<br>ATCGCCACGGCAGAACTCATCGCCGCCTGCCTTGCCCGCTGCTGGACAGG<br>GGCTAGGTTGCTGGGCACTGATAATTCCGTGGTGTTGTCGGGGAAATCAT<br>CGTCCTTTCCTTGGCTGCTCGCCTGTGTTGCCAACTGGATCCTGCGCGGG<br>ACGTCCTTCTGCTACGTCCCTTCGGCTCTCAATCCAGCGGACCTCCCTTC<br>CCGAGGCCTTCTGCCGGTTCTGCGGCCTCTCCCGCGTCTTCGCTTTCGGC<br>CTCCGACGAGTCGGATCTCCCTTTGGGCCGCCTCCCCGCCTG |
| 2926-3148 | Polyadenyl<br>ation signal | 54 | CTGTGCCTTCTAGTTGCCAGCCATCTGTTGTTTGCCCCTCCCCCGTGCCT<br>TCCTTGACCCTGGAAGGTGCCACTCCCACTGTCCTTTCCTAATAAAATGA<br><br>GGAAATTGCATCGCATTGTCTGAGTAGGTGTCATTCTATTCTGGGGGGTG<br>GGGTGGGGCAGGACAGCAAGGGGGAGGATTGGGAAGACAATAGCAGGCAT<br>GCTGGGGATGCGGTGGGCTCTAT |
| 3166-3273 | 3' ITR<br>[Bold text in brackets] | 55 | AGGAACCCCTAGTGATGGAGTTGGCCACTCCCTCTCTGCGCGCTCGCTCG<br>CTCACTGAGGCCGCCCGGGCTTTGCCCGGGCGGCCTCAGTGAGCGAGCGA<br>GCGCGCAG |

Complete Sequence of 71728 AAV:

(SEQ ID NO: 56)

[CTGCGCGCTC GCTCGCTCAC TGAGGCCGCC CGGGCAAAGC CCGGGCGTCG      50

GGCGACCTTT GGTCGCCCGG CCTCAGTGAG CGAGCGAGCG CGCAGAGAGG     100

GAGTGGCCAA CTCCATCACT AGGGGTTCCT] GCGGCCTAAG CTTGAGCTCT    150

TCGAAAGGCT CAGAGGCACA CAGGAGTTTC TGGGCTCACC CTGCCCCCTT     200

CCAACCCCTC AGTTCCCATC CTCCAGCAGC TGTTTGTGTG CTGCCTCTGA     250

AGTCCACACT GAACAAACTT CAGCCTACTC ATGTCCCTAA AATGGGCAAA     300

CATTGCAAGC AGCAAACAGC AAACACACAG CCCTCCCTGC CTGCTGACCT     350

TGGAGCTGGG GCAGAGGTCA GAGACCTCTC TGGGCCCATG CCACCTCCAA     400

CATCCACTCG ACCCCTTGGA ATTTCGGTGG AGAGGAGCAG AGGTTGTCCT     450

GGCGTGGTTT AGGTAGTGTG AGAGGGGTCC CGGGGATCTT *GCTACCAGTG*   500

*GAACAGCCAC TAAGGATTCT GCAGTGAGAG CAGAGGGCCA GCTAAGTGGT*   550

*ACTCTCCCAG AGACTGTCTG ACTCACGCCA CCCCCTCCAC CTTGGACACA*   600

*GGACGCTGTG GTTTCTGAGC CAGGTACAAT GACTCCTTTC GGTAAGTGCA*   650

*GTGGAAGCTG TACACTGCCC AGGCAAAGCG TCCGGGCAGC GTAGGCGGGC*   700

TABLE 5-continued

Elements of SB71728 AAV (SEQ ID NO:56)

| | |
|---|---|
| *GACTCAGATC CCAGCCAGTG GACTTAGCCC CTGTTTGCTC CTCCGATAAC* | 750 |
| *TGGGGTGACC TTGGTTAATA TTCACCAGCA GCCTCCCCCG TTGCCCCTCT* | 800 |
| *GGATCCACTG CTTAAATACG GACGAGGACA GGGCCCTGTC TCCTCAGCTT* | 850 |
| *CAGGCACCAC CACTGACCTG GGACAGTCCT AGGTG*CTTGT TCTTTTTGCA | 900 |
| GAAGCTCAGA ATAAACGCTC AACTTTGGCA GATACTAGTC AGGTAAGTAT | 950 |
| CAAGGTTACA AGACAGGTTT AAGGAGACCA ATAGAAACTG GCTTGTCGA | 1000 |
| GACAGAGAAG ACTCTTGCGT TTCTGATAGG CACCTATTGG TCTTACTGAC | 1050 |
| ATCCACTTTG CCTTTCTCTC CACAGGACCG GTGCCATGGA CTACAAAGAC | 1100 |
| CATGACGGTG ATTATAAAGA TCATGACATC GATTACAAGG ATGACGATGA | 1150 |
| CAAGATGGCC *CCCAAGAAGA AGAGGAAGGT C*GGCATTCAT GGGGTACCCg | 1200 |
| ccgctatggc tgagaggccc ttccagtgtc gaatctgcat gcgtaacttc | 1250 |
| agtcagtcct ccgacctgtc cgccacatc cgcacccaca ccggcgagaa | 1300 |
| gccttttgcc tgtgacattt gtgggaggaa atttgccctg aagcacaacc | 1350 |
| tgctgaccca taccaagata cacacgggcg agaagccctt ccagtgtcga | 1400 |
| atctgcatgc agaacttcag tgaccagtcc aacctgcgcg cccacatccg | 1450 |
| cacccacacc ggcgagaagc cttttgcctg tgacatttgt gggaggaaat | 1500 |
| ttgcccgcaa cttctccctg accatgcata ccaagataca caccggagag | 1550 |
| cgcggcttcc agtgtcgaat ctgcatgcgt aacttcagtc tgcgccacga | 1600 |
| cctggagcgc cacatccgca cccacaccgg cagaagcct tttgcctgtg | 1650 |
| acatttgtgg gaggaaattt gcccaccgct ccaacctgaa caagcatacc | 1700 |
| aagatacacc tgcggGGATC CCAGCTGGTG AAGAGCGAGC TGGAGGAGAA | 1750 |
| GAAGTCCGAG CTGCGGCACA AGCTGAAGTA CGTGCCCCAC GAGTACATCG | 1800 |
| AGCTGATCGA GATCGCCAGG AACAGCACCC AGGACCGCAT CCTGGAGATG | 1850 |
| AAGGTGATGG AGTTCTTCAT GAAGGTGTAC GGCTACAGGG GAAAGCACCT | 1900 |
| GGGCGGAAGC AGAAAGCCTG ACGGCGCCAT CTATACAGTG GGACGCCCCA | 1950 |
| TCGATTACGG CGTGATCGTG GACACAAAGG CCTACAGCGG CGGCTACAAT | 2000 |
| CTGAGCATCG GCCAGGCCGA CGAGATGCAG AGATACGTGA AGGAGAACCA | 2050 |
| GACCCGGAAT AAGCACATCA ACCCCAACGA GTGGTGGAAG GTGTACCCTA | 2100 |

TABLE 5-continued

Elements of SB71728 AAV (SEQ ID NO:56)

| | |
|---|---|
| GCAGCGTGAC CGAGTTCAAG TTCTGTTCG TGAGCGGCCA CTTCAAGGGC | 2150 |
| AACTACAAGG CCCAGCTGAC CAGGCTGAAC CGCAAAACCA ACTGCAATGG | 2200 |
| CGCCGTGCTG AGCGTGGAGG AGCTGCTGAT CGGCGGCGAG ATGATCAAAG | 2250 |
| CCGGCACCCT GACACTGGAG GAGGTGCGGC GCAAGTTCAA CAACGGCGAG | 2300 |
| ATCAACCTCT GATAACTCGA GTCTAGAAAT CAACCTCTGG ATTACAAAAT | 2350 |
| TTGTGAAAGA TTGACTGATA TTCTTAACTA TGTTGCTCCT TTTACGCTGT | 2400 |
| GTGGATATGC TGCTTTAATG CCTCTGTATC ATGCTATTGC TTCCCGTACG | 2450 |
| GCTTTCGTTT TCTCCTCCTT GTATAAATCC TGGTTGCTGT CTCTTTATGA | 2500 |
| GGAGTTGTGG CCCGTTGTCC GTCAACGTGG CGTGGTGTGC TCTGTGTTTG | 2550 |
| CTGACGCAAC CCCCACTGGC TGGGGCATTG CCACCACCTG TCAACTCCTT | 2600 |
| TCTGGGACTT TCGCTTTCCC CCTCCCGATC GCCACGGCAG AACTCATCGC | 2650 |
| CGCCTGCCTT GCCCGCTGCT GGACAGGGGC TAGGTTGCTG GGCACTGATA | 2700 |
| ATTCCGTGGT GTTGTCGGGG AAATCATCGT CCTTTCCTTG GCTGCTCGCC | 2750 |
| TGTGTTGCCA ACTGGATCCT GCGCGGGACG TCCTTCTGCT ACGTCCCTTG | 2800 |
| GGCTCTCAAT CCAGCGGACC TCCCTTCCCG AGGCCTTCTG CCGGTTCTGC | 2850 |
| GGCCTCTCCC GCGTCTTCGC TTTCGGCCTC CGACGAGTCG GATCTCCCTT | 2900 |
| TGGGCCGCCT CCCCGCCTGG CTAGCCTGTG CCTTCTAGTT GCCAGCCATC | 2950 |
| TGTTGTTTGC CCCTCCCCCG TGCCTTCCTT GACCCTGGAA GGTGCCACTC | 3000 |
| CCACTGTCCT TTCCTAATAA AATGAGGAAA TTGCATCGCA TTGTCTGAGT | 3050 |
| AGGTGTCATT CTATTCTGGG GGGTGGGGTG GGGCAGGACA GCAAGGGGGA | 3100 |
| GGATTGGGAA GACAATAGCA GGCATGCTGG GGATGCGGTG GCTCTATGC | 3150 |
| GGCCGCGTCG AGCGC**[AGGAA CCCTAGTGA TGGAGTTGGC CACTCCCTCT** | 3200 |
| CTGCGCGCTC GCTCGCTCAC TGAGGCCGCC CGGGCTTTGC CCGGGCGGCC | 3250 |
| TCAGTGAGCG AGCGAGCGCG CAG] | 3273 |

A series of transgene vectors (F9, IDS and IDUA) were made to insert into the albumin gene using the ZFN pair shown above (71557/71728), see FIG. 11 depicting the results for the hIDS insertion. The vectors were AAV vectors and all comprised regions of homology flanking the ZFN cleavage site (left homology arm: LA, and right homology arm: RA). The vectors further comprised splice acceptor sequences (SA) and polyA signal sequences (polyA). Finally, all comprised 5' and 3' AAV ITR sequences. The elements and sequences of the Factor 9 exon 2-9 AAV transgene donor are shown below.

TABLE 6

| | Elements of Factor 9 AAV (SEQ ID NO:59) | | |
|---|---|---|---|
| Position | Feature Description | SEQ ID NO | Seqence |
| 1-130 | 5' ITR [plain text in brackets] | 44 | CTGCGCGCTCGCTCGCTCACTGAGGCCGCCCGGGCAAAGCCCGGGCGTCG GGCGACCTTTGGTCGCCCGGCCTCAGTGAGCGAGCGAGCGCGCAGAGAGG GAGTGGCCAACTCCATCACTAGGGGTTCCT |
| 271-550 | LA: Left homology arm *italics* | 60 | TTTATTCTATTTTCCCAGTAAAATAAAGTTTTAGTAAACTCTGCATCTTT AAAGAATTATTTTGGCATTTATTTCTAAAATGGCATAGTATTTTGTATTT GTGAAGTCTTACAAGGTTATCTTATTAATAAAATTCAAACATCCTAGGTA AAAAAAAAGGTCAGAATTGTTTAGTGACTGTAATTTTCTTTTGCGC ACTAAGGAAAGTGCAAAGTAACTTAGAGTGACTGAAACTTCACAGAATAG GGTTGAAGATTGAATTCATAACTATCCCAA |
| 557-584 | SA: Splice acceptor Bold | 61 | ACTAAAGAATTATTCTTTTACATTTCAG |
| 585-1882 | hF9 exons 2-8, codon optimized underlined | 62 | TTTTTCTTGATCATGAAAACGCCAACAAAATCCTGAACCGGCCCAAGCGG TACAACTCAGGCAAGCTGGAAGAGTTCGTGCAGGGCAACCTGGAACGGGA GTGCATGGAAGAGAAGTGCAGCTTCGAGGAAGCCCGGGAGGTGTTCGAGA ACACCGAGCGGACCACCGAGTTCTGGAAGCAGTACGTGGACGGCGACCAG TGCGAGTCAAACCCCTGCCTGAACGGCGGCAGCTGCAAGGACGATATCAA CAGCTACGAGTGCTGGTGCCCCTTCGGCTTCGAGGGCAAGAACTGCGAGC TGGACGTGACCTGCAACATCAAGAACGGCCGCTGCGAGCAGTTCTGCAAG AACAGCGCCGACAACAAGGTGGTGTGCTCATGCACTGAGGGCTACCGGCT GGCCGAGAACCAGAAGAGCTGCGAGCCCGCCGTGCCCTTCCCCTGCGGCA GAGTGTCCGTGAGCCAGACCAGCAAGCTGACCAGGGCCGAGGCCGTGTTC CCTGACGTGGACTACGTGAACTCAACCGAGGCCGAGACAATCCTGGACAA CATCACCCAGAGCACCCAGTCCTTCAACGACTTCACCCGGGTGGTGGGCG GCGAGGACGCCAAGCCCGGCCAGTTCCCTTGGCAGGTGGTGCTGAACGGC AAGGTGGACGCCTTCTGCGGCGGCTCAATCGTGAACGAGAAGTGGATCGT GACAGCCGCCCACTGCGTGGAGACAGGCGTGAAGATCACCGTGGTGGCCG GCGAACACAATATCGAGGAAACCGAGCACACCGAGCAGAAACGGAACGTG ATCCGGATTATCCCCCACCACAACTACAACGCCGCCATCAACAAGTACAA CCACGATATCGCCCTGCTGGAACTGGACGAGCCTCTGGTGCTGAATTCAT ACGTGACCCCCATCTGTATCGCCGACAAAGAGTACACCAACATCTTTCTG AAGTTCGGCAGCGGCTACGTGTCCGGCTGGGGCAGGGTGTTCCACAAGGG CCGCAGCGCCCTGGTGCTGCAGTACCTGCGGGTGCCCCTGGTGGACAGAG CCACCTGCCTGCGGTCAACCAAGTTCACCATCTACAACAACATGTTCTGC GCCGGCTTCCACGAGGGCGGCAGGGACAGCTGCCAGGGCGACAGCGGCGG ACCCCACGTGACCGAGGTGGAGGGCACCAGCTTTCTGACCGGCATCATCT CATGGGGCGAGGAATGCGCCATGAAGGGCAAGTACGGAATCTACACTAAG GTGTCAAGATACGTGAACTGGATCAAAGAGAAAACCAAGCTGACCTGA |
| 1890-2114 | poly A lowercase | 63 | CTGTGCCTTCTAGTTGCCAGCCATCTGTTGTTTGCCCCTCCCCCGTGCCT TCCTTGACCCTGGAAGGTGCCACTCCCACTGTCCTTTCCTAATAAAATGA GGAAATTGCATCGCATTGTCTGAGTAGGTGTCATTCTATTCTGGGGGGTG GGGTGGGGCAGGACAGCAAGGGGGAGGATTGGGAAGACAATAGCAGGCAT GCTGGGGATGCGGTGGGCTCTATGG |
| 2121-2220 | RA: Right homology arm Double underlined | 64 | CTATCCATTGCACTATGCTTTATTTAAAAACCACAAAACCTGTGCTGTTG ATCTCATAAATAGAACTTGTATTTATATTTATTTTCATTTTAGTCTGTCT |
| 2367-2474 | 3' ITR [Bold bracketed] | 55 | AGGAACCCCTAGTGATGGAGTTGGCCACTCCCTCTCTGCGCGCTCGCTCG CTCACTGAGGCCGCCCGGGCTTTGCCCGGGCGGCCTCAGTGAGCGAGCGA GCGCGCAG |

Sequence of F9 AAV:

(SEQ ID NO: 59)

[CTGCGCGCTC GCTCGCTCAC TGAGGCCGCC CGGGCAAAGC CCGGGCGTCG    50

GGCGACCTTT GGTCGCCCGG CCTCAGTGAG CGAGCGAGCG CGCAGAGAGG    100

TABLE 6-continued

Elements of Factor 9 AAV (SEQ ID NO:59)

| | |
|---|---|
| GAGTGGCCAA CTCCATCACT AGGGGTTCCT] GCGGCCTAAG CTTGAGCGGA | 150 |
| GTTCCAATTG TACTGTACAG AACCATGGTC ACATGTTTAA CGCTAGCGTG | 200 |
| CCGACCTGGT AAACTGATCA GTGGGTGCAC TTAGGACTGC GTCTTACGCT | 250 |
| AATCACATGC GTGCGGCCGC *TTTATTCTAT TTTCCCAGTA AAATAAAGTT* | 300 |
| *TTAGTAAACT CTGCATCTTT AAAGAATTAT TTTCCGATTT ATTTCTAAAA* | 350 |
| *TGGCATAGTA TTTTGTATTT GTGAAGTCTT ACAAGGTTAT CTTATTAATA* | 400 |
| *AAATTCAAAC ATCCTAGGTA AAAAAAAAA AAGGTCAGAA TTGTTTAGTG* | 450 |
| *ACTGTAATTT TCTTTTGCGC ACTAAGGAAA GTGCAAAGTA ACTTAGAGTG* | 500 |
| *ACTGAAACTT CACAGAATAG GGTTGAAGAT TGAATTCATA ACTATCCCAA* | 550 |
| GGTACCACTA AAGAATTATT CTTTTACATT TCAG<u>TTTTTC TTGATCATGA</u> | 600 |
| <u>AAACGCCAAC AAAATCCTGA ACCGGCCCAA GCGGTACAAC TCAGGCAAGC</u> | 650 |
| <u>TGGAAGAGTT CGTGCAGGGC AACCTGGAAC GGGAGTGCAT GGAAGAGAAG</u> | 700 |
| <u>TGCAGCTTCG AGGAAGCCCG GGAGGTGTTC GAGAACACCG AGCGGACCAC</u> | 750 |
| <u>CGAGTTCTGG AAGCAGTACG TGGACGGCGA CCAGTGCGAG TCAAACCCCT</u> | 800 |
| <u>GCCTGAACGG CGGCAGCTGC AAGGACGATA TCAACAGCTA CGAGTGCTGG</u> | 850 |
| <u>TGCCCCTTCG GCTTCGAGGG CAAGAACTGC GAGCTGGACG TGACCTGCAA</u> | 900 |
| <u>CATCAAGAAC GGCCGCTGCG AGCAGTTCTG CAAGAACAGC GCCGACAACA</u> | 950 |
| <u>AGGTGGTGTG CTCATGCACT GAGGGCTACC GGCTGGCCGA GAACCAGAAG</u> | 1000 |
| <u>AGCTGCGAGC CCGCCGTGCC CTTCCCCTGC GGCAGAGTGT CCGTGAGCCA</u> | 1050 |
| <u>GACCAGCAAG CTGACCAGGG CCGAGGCCGT GTTCCCTGAC GTGGACTACG</u> | 1100 |
| <u>TGAACTCAAC CGAGGCCGAG ACAATCCTGG ACAACATCAC CCAGAGCACC</u> | 1150 |
| <u>CAGTCCTTCA ACGACTTCAC CCGGGTGGTG GGCGGCGAGG ACGCCAAGCC</u> | 1200 |
| <u>CGGCCAGTTC CCTTGGCAGG TGGTGCTGAA CGGCAAGGTG GACGCCTTCT</u> | 1250 |
| <u>GCGGCGGCTC AATCGTGAAC GAGAAGTGGA TCGTGACAGC CGCCCACTGC</u> | 1300 |
| <u>GTGGAGACAG GCGTGAAGAT CACCGTGGTG GCCGGCGAAC ACAATATCGA</u> | 1350 |
| <u>GGAAACCGAG CACACCGAGC AGAAACGGAA CGTGATCCGG ATTATCCCCC</u> | 1400 |
| <u>ACCACAACTA CAACGCCGCC ATCAACAAGT ACAACCACGA TATCGCCCTG</u> | 1450 |
| <u>CTGGAACTGG ACGAGCCTCT GGTGCTGAAT TCATACGTGA CCCCCATCTG</u> | 1500 |
| <u>TATCGCCGAC AAAGAGTACA CCAACATCTT TCTGAAGTTC GGCAGCGGCT</u> | 1550 |

TABLE 6-continued

Elements of Factor 9 AAV (SEQ ID NO:59)

```
ACGTGTCCGG CTGGGGCAGG GTGTTCCACA AGGGCCGCAG CGCCCTGGTG    1600

CTGCAGTACC TGCGGGTGCC CCTGGTGGAC AGAGCCACCT GCCTGCGGTC    1650

AACCAAGTTC ACCATCTACA ACAACATGTT CTGCGCCGGC TTCAACGAGG    1700

GCGGCAGGGA CAGCTGCCAG GGCGACAGCG GCGGACCCCA CGTGACCGAG    1750

TGGGAGGGCA CCAGCTTTCT GACCGGCATC ATCTCATGGG GCGAGGAATG    1800

CGCCATGAAG GGCAAGTACG GAATCTACAC TAAGGTGTCA AGATACGTGA    1850

ACTGGATCAA AGAGAAAACC AAGCTGACCT GAGTTTAAAc tgtgccttct    1900
agttgccagc catctgttgt ttgcccctcc cccgtgcctt ccttgaccct    1950
ggaaggtgcc actcccactg tcctttccta ataaaatgag gaaattgcat    2000
cgcattgtct gagtaggtgt cattctattc tggggggtgg ggtgggcag    2050 gacagcaagg gggaggattg ggaagacaat agcaggcatg ctggggatgc    2100
ggtgggctct atggACCGGT CTATCCATTG CACTATGCTT TATTTAAAAA    2150

CCACAAAACC TGTGCTGTTG ATCTCATAAA TAGAACTTGT ATTTATATTT    2200

ATTTTCATTT TAGTCTGTCT GGATCCACAA ATTAATCGAA CCTGCAGCTG    2250

ATATCGACGC TTAAGTAGGG CTTAGCAAAC GCGTCTCCAA CGTTTCGCCG    2300

TTAACACCCC ACATAGTGAG TGGTCTTAGT AGTCCGGGTG TTTAAACTGA    2350

AAGATAACTC GAGCGC[AGGA ACCCCTAGTG ATGGAGTTGG CCACTCCCTC    2400

TCTGCGCGCT CGCTCGCTCA CTGAGGCCGC CCGGGCTTTG CCCGGCGGC    2450

CTCAGTGAGC GAGCGAGCGC GCAG]                              2474
```

The elements and sequences of the IDS AAV transgene donor are shown below:

TABLE 7

| Position | Feature Description | SEQ ID NO | Sequence |
|---|---|---|---|
| 1-130 | 5' ITR [plain text in brackets] | 44 | CTGCGCGCTCGCTCGCTCACTGAGGCCGCCCGGGCAAAGCCCGGGCGTCG GGCGACCTTTGGTCGCCCGGCCTCAGTGAGCGAGCGAGCGCGCAGAGAGG GAGTGGCCAACTCCATCACTAGGGGTTCCT |
| 271-550 | LA: Left homology arm *italics* | 60 | TTTATTCTATTTTCCCAGTAAAATAAAGTTTTAGTAAACTCTGCATCTTT AAAGAATTATTTTGGCATTTATTTCTAAAATGGCATAGTATTTTGTATTT GTGAAGTCTTACAAGGTTATCTTATTAATAAAATTCAAACATCCTAGGTA GGTCAGAATTGTTTAGTGACTGTAATTTTCTTTTGCGC ACTAAGGAAAGTGCAAAGTAACTTAGAGTGACTGAAACTTCACAGAATAG GGTTGAAGATTGAATTCATAACTATCCCAA |
| 557-584 | SA: Splice acceptor Bold | 61 | ACTAAAGAATTATTCTTTTACATTTCAG |

TABLE 7-continued

Elements of IDS AAV (SEQ ID NO:65)

| 587-2161 | hIDS codon optimized <u>underlined</u> | 66 | AGCGAAACCCAGGCCAACTCAACTACAGATGCGCTTAACGTCCTGCTCAT<br>CATCGTGGACGATTTGCGGCCGTCGCTTGGCTGCTATGGAGATAAGCTCG<br>TCCGCTCGCCGAACATCGATCAGTTGGCCTCACACTCACTGCTTTTCCAA<br>AATGCGTTTGCGCAGCAGGCTGTCTGTGCACCTTCAAGAGTCTCATTCTT<br>GACCGGGCGACGCCCTGACACAACGCGGCTGTACGACTTCAACAGCTACT<br>GGAGAGTCCACGCGGGTAACTTTTCAACTATCCCACAGTACTTTAAAGAG<br>AACGGATACGTGACAATGAGCGTGGGAAAGGTCTTTCACCCCGGCATCTC<br>CTCGAATCACACCGACGATTCGCCCTACTCGTGGTCGTTTCCTCCCTACC<br>ATCCTTCGAGCGAGAAGTATGAGAACACGAAAACTTGTCGCGGACCCGAC<br>GGAGAGCTGCACGCTAATCTGCTGTGTCCGGTGGATGTCTTGGACGTGCC<br>CGAGGGAACGCTCCCCGACAAGCAGTCAACGGAGCAGGCGATTCAGTTGC<br>TGGAGAAGATGAAAACAAGCGCGTCGCCTTTCTTCCTCGCCGTGGGGTAT<br>CACAAGCCCCATATTCCTTTCCGCTACCCGAAGGAGTTCCAGAAACTTTA<br>TCCTTTGGAAAACATCACTTTGGCACCGGACCCGGAAGTCCCCGACGGTC<br>TGCCACCCGTGGCCTACAATCCCTGGATGGATATCAGGCAGAGGGAAGAT<br>GTGCAGGCACTCAACATCTCAGTCCCCTACGGGCCTATTCCAGTCGATTT<br>TCAACGCAAGATTCGGCAGTCGTATTTTGCGTCGGTGTCCTACCTCGATA<br>CGCAAGTAGGTCGACTTCTGAGCGCGCTTGATGACCTTCAGCTGGCAAAT<br>TCCACAATCATCGCCTTTACGTCGGACCATGGGTGGGCGTTGGGAGAGCA<br>TGGAGAGTGGGCAAAGTATAGCAATTTTGATGTAGCAACGCACGTGCCCC<br>TGATTTTCTACGTGCCGGGTAGAACGGCCTCGCTTCCCGAGGCAGGCGAA<br>AAACTTTTTCCCTATCTCGATCCATTCGACTCGGCGAGCCAGCTTATGGA<br>ACCGGGCAGACAATCCATGGACTTGGTAGAATTGGTGTCCCTTTTTCCGA<br>CCCTCGCCGGGTTGGCGGGCTTGCAAGTACCCCCTAGATGCCCTGTACCG<br>AGCTTCCATGTGGAACTCTGCCGCGAAGGGAAAAACCTCCTCAAACACTT<br>TCGGTTCAGGGACCTTGAGGAGGACCCCTATCTGCCAGGGAATCCGCGAG<br>AGTTGATTGCCTATTCCCAGTATCCGGACCCAGCGATATTCCTCAATGG<br>AACTCCGATAAGCCCTCCCTCAAAGACATCAAGATTATGGGGTACTCGAT<br>CAGGACCATCGACTATCGCTACACAGTGTGGGTAGGGTTCAATCCTGACG<br>AATTCCTCGCGAACTTTTCGGACATCCACGCTGGTGAGCTGTATTTCGTA<br>GACTCGGACCCGTTGCAAGATCACAATATGTATAATGATTCCCAAGGAGG<br>AGATTTGTTCCAGCTGCTCATGCCG |
| 2174-2398 | poly A lowercase | 63 | CTGTGCCTTCTAGTTGCCAGCCATCTGTTGTTTGCCCCTCCCCCGTGCCT<br>TCCTTGACCCTGGAAGGTGCCACTCCCACTGTCCTTTCCTAATAAAATGA<br>GGAAATTGCATCGCATTGTCTGAGTAGGTGTCATTCTATTCTGGGGGGTG<br>GGGTGGGGCAGGACAGCAAGGGGGAGGATTGGGAAGACAATAGCAGGCAT<br>GCTGGGGATGCGGTGGGCTCTATGG |
| 2405-2504 | RA: Right homology arm <u>Double underlined</u> | 64 | CTATCCATTGCACTATGCTTTATTTAAAAACCACAAAACCTGTGCTGTTG<br>ATCTCATAAATAGAACTTGTATTTATATTTATTTTCATTTTAGTCTGTCT |
| 2651-2758 | 3' ITR [Bold bracketed] | 55 | AGGAACCCCTAGTGATGGAGTTGGCCACTCCCTCTCTGCGCGCTCGCTCG<br>CTCACTGAGGCCGCCCGGGCTTTGCCCGGGCGGCCTCAGTGAGCGAGCGA<br>GCGCGCAG |

Sequence of hIDS AAV:

(SEQ ID NO: 65)

[CTGCGCGCTC GCTCGCTCAC TGAGGCCGCC CGGGCAAAGC CCGGGCGTCG    50

GGCGACCTTT GGTCGCCCGG CCTCAGTGAG CGAGCGAGCG CGCAGAGAGG    100

GAGTGGCCAA CTCCATCACT AGGGGTTCCT] GCGGCCTAAG CTTGAGCGGA    150

GTTCCAATTG TACTGTACAG AACCATGGTC ACATGTTTAA CGCTAGCGTG    200

CCGACCTGGT AAACTGATCA GTGGGTGCAC TTAGGACTGC GTCTTACGCT    250

AATCACATGC GTGCGGCCGC *TTTATTCTAT TTTCCCAGTA AAATAAAGTT*    300

*TTAGTAAACT CTGCATCTTT AAAGAATTAT TTTGGCATTT ATTTCTAAAA*    350

*TGGCATAGTA TTTTGTATTT GTGAAGTCTT ACAAGGTTAT CTTATTAATA*    400

*AAATTCAAAC ATCCTAGGTA AAAAAAAAA AAGGTCAGAA TTGTTTAGTG*    450

*ACTGTAATTT TCTTTTGCGC ACTAAGGAAA GTGCAAAGTA ACTTAGAGTG*    500

TABLE 7-continued

Elements of IDS AAV (SEQ ID NO:65)

| | |
|---|---|
| *ACTGAAACTT CACAGAATAG GGTTGAAGAT TGAATTCATA ACTATCCCAA* | 550 |
| GGTACCACTA AAGAATTATT CTTTTACATT TCAGTTAGCG AAACCCAGGC | 600 |
| CAACTCAACT ACAGTGCGC TTAACGTCCT GCTCATCATC GTGGACGATT | 650 |
| TGCGGCCGTC GCTTGGCTGC TATGGAGATA AGCTCGTCCG CTCGCCGACC | 700 |
| ATCGATCAGT TGGCCTCACA CTCACTGCTT TTCAAAATG CGTTTGCGCA | 750 |
| GCAGGCTGTC TGTGCACCTT CAAGAGTCTC ATTCTTGACC GGGCCACGCC | 800 |
| CTGACACAAC GCGGCTGTAC GACTTCAACA GCTACTGGAG AGTCCACGCG | 850 |
| GGTAACTTTT CAACTATCCC ACAGTACTTT AAAGAGAACG GATACGTGAC | 900 |
| AATGAGCGTG GGAAAGGTCT TTCACCCCGG CATCTCCTCG AATCACACCG | 950 |
| ACGATTCGCC CTACTCGTGG TCGTTTCCTC CCTACCATCC TTCGAGCGAG | 1000 |
| AAGTATGAGA ACACGAAAAC TTGTCGCGGA CCCGACGGAG AGCTGCACGC | 1050 |
| TAATCTGCTG TGTCCGGTGG ATGTCTTGGA CGTGCCCGAG GGAACGCTCC | 1100 |
| CCGACAAGCA GTCAACGGAG CAGGCGATTC AGTTGCTGGA GAAGATGAAA | 1150 |
| ACAAGCGCGT CGCCTTTCTT CCTCGCCGTG GGGTATCACA AGCCCCATAT | 1200 |
| TCCTTTCCGC TACCCGAAGG AGTTCCAGAA ACTTTATCCT TTGGAAAACA | 1250 |
| TCACTTTGGC ACCGGACCCG GAAGTCCCCG ACGGTCTGCC ACCCGTGGCC | 1300 |
| TACAATCCCT GGATGGATAT CAGGCAGAGG GAAGATGTGC AGGCACTCAA | 1350 |
| CATCTCAGTC CCCTACGGGC CTATTCCAGT CGATTTTCAA CGCAAGATTC | 1400 |
| GGCAGTCGTA TTTTGCGTCG GTGTCCTACC TCGATACGCA AGTAGGTCGA | 1450 |
| CTTCTGAGCG CGCTTGATGA CCTCAGCTG GCAAATTCCA CAATCATCGC | 1500 |
| CTTTACGTCG GACCATGGGT GGGCGTTGGG AGAGCATGGA GAGTGGGCAA | 1550 |
| AGTATAGCAA TTTTGATGTA GCAACGCACG TGCCCCTGAT TTTCTACGTG | 1600 |
| CCGGGTAGAA CGGCCTCGCT TCCCGAGGCA GGCGAAAAAC TTTTTCCCTA | 1650 |
| TCTCGATCCA TTCGACTCGG CGAGCCAGCT TATGGAACCG GGCAGACAAT | 1700 |
| CCATGGACTT GGTAGAATTG GTGTCCCTTT TTCCGACCCT CGCCGGGTTG | 1750 |
| GCGGGCTTGC AAGTACCCCC TAGATGCCCT GTACCGAGCT TCCATGTGGA | 1800 |
| ACTCTGCCGC GAAAGGGAAAA ACCTCCTCAA ACACTTTCGG TTCAGGGACC | 1850 |
| TTGAGGAGGA CCCCTATCTG CCAGGGAATC CGCGAGAGTT GATTGCCTAT | 1900 |
| TCCCAGTATC CGCGACCCAG CGATATTCCT CAATGGAACT CCGATAAGCC | 1950 |

TABLE 7-continued

Elements of IDS AAV (SEQ ID NO:65)

| | |
|---|---|
| <u>CTCCCTCAAA GACATCAAGA TTATGGGGTA CTCGATCAGG ACCATCGACT</u> | 2000 |
| <u>ATCGCTACAC AGTGTGGGTA GGGTTCAATC CTGACGAATT CCTCGCGAAC</u> | 2050 |
| <u>TTTTCGGACA TCCACGCTGG TGAGCTGTAT TTCGTAGACT CGGACCCGTT</u> | 2100 |
| <u>GCAAGATCAG AATATGTATA ATGATTCCCA AGGAGGAGAT TTGTTCCAGC</u> | 2150 |
| <u>TGCTCATGCC</u> GTGATAAAGA TCTctgtgcc ttctagttgc cagccatctg | 2200 |
| ttgtttgccc ctcccccgtg ccttccttga ccctggaagg tgccactccc | 2250 |
| actgtccttt cctaataaaa tgaggaaatt gcatcgcatt gtctgagtag | 2300 |
| gtgtcattct attctggggg gtggggtggg gcaggacagc aaggggagg | 2350 |
| attgggaaga caatagcagg catgctgggg atgcggtggg ctctatggAC | 2400 |
| CGGTCTATCC ATTGCACTAT GCTTTATTTA AAAACCACAA AACCTGTGCT | 2450 |
| GTTGATCTCA TAAATAGAAC TTGTATTTAT ATTTATTTTC ATTTTAGTCT | 2500 |
| <u>GTCTGGATCC</u> ACAAATTAAT CGAACCTGCA GCTGATATCG ACGCTTAAGT | 2550 |
| AGGGCTTAGC AAACGCGTCT CCAACGTTTC GCCGTTAACA CCCCACATAG | 2600 |
| TGAGTGGTCT TAGTAGTCCG GGTGTTTAAA CTGAAAGATA ACTCGAGCGC | 2650 |
| [AGGAACCCCT AGTGATGGAG TTGGCCACTC CCTCTCTGCT GCGCTCGCTCG | 2700 |
| CTCACTGAGG CCGCCCGGGC TTTGCCCGGG CGGCCTCAGT GAGCGAGCGA | 2750 |
| GCGCGCAG] | 2758 |

The elements and sequences of the IDUA AAV transgene donor are shown below:

TABLE 8

Elements of IDUA AAV (SEQ ID NO: 72)

| Position | Feature Description | SEQ ID NO | Sequence |
|---|---|---|---|
| 1-130 | 5' ITR [plain text in brackets] | 44 | CTGCGCGCTCGCTCGCTCACTGAGGCCGCCCGGGCAAAGCCCGGGCGTCG GGCGACCTTTGGTCGCCCGGCCTCAGTGAGCGAGCGAGCGCGCAGAGAGG GAGTGGCCAACTCCATCACTAGGGGTTCCT |
| 271-560 | LA: Left homology arm *italics* | 60 | TTTATTCTATTTTCCCAGTAAAATAAAGTTTTAGTAAAACTCTGCATCTTT AAAGAATTATTTTGGCATTTATTTCTAAAATGGCATAGTATTTTGTATTT GTGAAGTCTTACAAGGTTATCTTATTAATAAAATTCAAACATCCTAGGTA AAAAAAAAAGGTCAGAATTGTTTAGTGACTGTAATTTTCTTTTGCGC ACTAAGGAAAGTGCAAAGTAACTTAGAGTGACTGAAACTTCACAGAATAG GGTTGAAGATTGAATTCATAACTATCCCAA |
| 557-584 | SA: Splice acceptor Bold | 61 | ACTAAAGAATTATTCTTTTACATTTCAG |
| 587-2458 | hIDUA, codon optimized <u>underlined</u> | 67 | CACTTGGTCCACGTCGACGCTGCCAGAGCCCTGTGGCCGCTTCGAAGATT TTGGAGGTCAACGGGTTTCTGTCCTCCCCTTCCCCACTCGCAAGCAGATC AGTATGTACTGTCATGGGATCAACAGCTTAACCTCGCCTATGTCGGAGCA GTGCCTCACCGCGGGATCAAGCAAGTAAGGACACATTGGCTCCTTGAACT CGTCACCACGAGAGGATCGACGGGAAGGGGGCTTTCGTACAACTTCACTC ATCTCGATGGCTATTTGGATCTCCTCCGCGAGAATCAGTTGTTGCCAGGC |

TABLE 8-continued

Elements of IDUA AAV (SEQ ID NO: 72)

|   |   |   |   |
|---|---|---|---|
|   |   |   | TTCGAATTGATGGGATCGGCGAGCGGGCACTTTACAGACTTCGAGGACAA GCAGCAAGTGTTTGAGTGGAAGGACCTCGTGTCGTCGCTCGCGAGGAGAT ACATTGGTCGCTACGGTTTGGCGCATGTGTCAAAGTGGAACTTCGAAACG TGGAACGAGCCCGATCATCACGATTTTGACAACGTGTCAATGACCATGCA GGGTTTCCTTAACTATTACGACGCCTGTTCCGAGGGATTGAGGGCAGCAT CACCGGCGCTTCGGCTGGGAGGGCCTGGTGATAGCTTTCATACACCACCT CGATCGCCACTTTCGTGGGGGCTGCTGCGCCATTGTCACGATGGTACGAA CTTCTTCACCGGGGAAGCGGGGGTACGGCTTGATTACATCAGCCTCCACC GAAAGGGAGCGCGGTCAAGCATCTCGATTCTGGAGCAGGAGAAGGTAGTC GCTCAGCAGATCCGGCAACTCTTTCCCAAGTTCGCAGACACACCTATCTA CAATGATGAGGCAGACCCACTTGTGGGATGGTCCCTTCCGCAGCCATGGC GCGCAGATGTGACTTATGCCGCGATGGTAGTGAAAGTCATCGCCCAGCAC CAGAATCTGCTTCTTGCGAATACGACCAGCGCGTTTCCTTACGCGCTTTT GTCGAACGATAATGCCTTCCTGTCATATCACCCCCATCCGTTTGCGCAGA GGACTCTTACGGCGCGATTCCAAGTGAATAACACCAGACCGCCGCACGTG CAGCTGTTGCGAAAACCCGTGTTGACTGCGATGGGGCTTCTGGCGTTGCT TGATGAGGAACAACTCTGGGCTGAAGTGTCCCAGGCGGGGACAGTACTTG ATAGCAATCATACAGTAGGCGTGTTGGCGTCGGCGCACCGACCGCAGGGA CCCGCGGATGCTTGGAGGGCAGCGGTCCTGATCTACGCCTCGGACGATAC TAGGGCACATCCCAACAGATCGGTCGCTGTCACCCTTCGCCTCAGAGGGG TCCCGCCTGGTCCCGGCTTGGTATACGTCACTAGATATCTCGACAATGGA CTGTGCAGCCCCGACGGAGAGTGGCGGAGGCTGGGACGGCCGGTGTTTCC GACAGCCGAGCAGTTTAGACGGATGAGGGCCGCTGAGGACCCCGTGGCAG CGGCACCGAGGCCCCTCCCGGCAGGAGGTCGCCTCACTCTTCGACCGGCA CTGCGGCTGCCGTCCCTTCTGCTCGTACACGTCTGCGCGCGACCCGAAAA GCCGCCTGGACAGGTAACCAGGCTCAGGGCGCTCCCCTTGACGCAGGGGC AGTTGGTACTTGTCTGGTCGGACGAACACGTGGGGTCCAAATGCTTGTGG ACGTATGAAATTCAGTTTTCCCAAGACGGGAAAGCGTACACTCCGGTGTC GCGCAAACCCTCCACGTTCAACCTCTTCGTCTTTTCCCCAGACACGGGAG CCGTATCAGGGTCGTACCGAGTCAGAGCCCTCGATTATTGGGCGAGGCCT GGGCCGTTCTCGGACCCTGTACCATACTTGGAAGTGCCGGTGCCCAGGGG ACCGCCCTCGCCTGGTAATCCT |
| 2471-2695 | poly A lowercase | 63 | CTGTGCCTTCTAGTTGCCAGCCATCTGTTGTTTGCCCCTCCCCCGTGCCT TCCTTGACCCTGGAAGGTGCCACTCCCACTGTCCTTTCCTAATAAAATGA GGAAATTGCATCGCATTGTCTGAGTAGGTGTCATTCTATTCTGGGGGGTG GGGTGGGGCAGGACAGCAAGGGGGAGGATTGGGAAGACAATAGCAGGCAT GCTGGGGATGCGGTGGGCTCTATGG |
| 2702-2801 | RA: Right homology arm <u><u>Double underlined</u></u> | 64 | CTATCCATTGCACTATGCTTTATTTAAAAACCACAAAACCTGTGCTGTTG ATCTCATAAATAGAACTTGTATTTATATTTATTTTCATTTTAGTCTGTCT |
| 2948-3055 | 3' ITR [Bold bracketed] | 55 | AGGAACCCCTAGTGATGGAGTTGGCCACTCCCTCTCTGCGCGCTCGCTCG CTCACTGAGGCCGCCCGGGCTTTGCCCGGGCGGCCTCAGTGAGCGAGCGA GCGCGCAG |

Sequence of IDUA AAV:

(SEQ ID NO: 72)

[CTGCGCGCTC GCTCGCTCAC TGAGGCCGCC CGGGCAAAGC CCGGGCGTCG      50

GGCGACCTTT GGTCGCCCGG CCTCAGTGAG CGAGCGAGCG CGCAGAGAGG     100

GAGTGGCCAA CTCCATCACT AGGGGTTCCT] GCGGCCTAAG CTTGAGCGGA     150

GTTCCAATTG TACTGTACAG AACCATGGTC ACATGTTTAA CGCTAGCGTG     200

CCGACCTGGT AAACTGATCA GTGGGTGCAC TTAGGACTGC GTCTTACGCT     250

AATCACATGC GTGCGGCCGC *TTTATTCTAT TTTCCCAGTA AAATAAAGTT*     300

*TTAGTAAACT CTGCATCTTT AAAGAATTAT TTTGGCATTT ATTTCTAAAA*     350

*TGGCATAGTA TTTTGTATTT GTGAAGTCTT ACAAGGTTAT CTTATTAATA*     400

*AAATTCAAAC ATCCTAGGTA AAAAAAAAAA AAGGTCAGAA TTGTTTAGTG*     450

*ACTGTAATTT TCTTTTGCGC ACTAAGGAAA GTGCAAAGTA ACTTAGAGTG*     500

TABLE 8-continued

Elements of IDUA AAV (SEQ ID NO: 72)

| | |
|---|---|
| *ACTGAAACTT CACAGAATAG GGTTGAAGAT TGAATTCATA ACTATCCCAA* | 550 |
| GGTACCACTA AAGAATTATT CTTTTACATT TCAGCGCACT TGGTCCACGT | 600 |
| CGACGCTGCC AGAGCCCTGT GGCCGCTTCG AAGATTTTGG AGGTCAACGG | 650 |
| GTTTCTGTCC TCCCCTTCCC CACTCGCAAG CAGATCAGTA TGTACTGTCA | 700 |
| TGGGATCAAC AGCTTAACCT CGCCTATGTC GGAGCAGTGC CTCACCGCGG | 750 |
| GATCAAGCAA GTAAGGACAC ATTGGCTCCT TGAACTCGTC ACCACGAGAG | 800 |
| GATCGACGGG AAGGGGGCTT TCGTACAACT TCACTCATCT CGATGGCTAT | 850 |
| TTGGATCTCC TCCGCGAGAA TCAGTTGTTG CCAGGCTTCG AATTGATGGG | 900 |
| ATCGGCGAGC GGGCACTTTA CAGACTTCGA GGACAAGCAG CAAGTGTTTG | 950 |
| AGTGGAAGGA CCTCGTGTCG TCGCTCGCGA GGAGATACAT TGGTCGCTAC | 1000 |
| GGTTTGGCGC ATGTGTCAAA GTGGAACTTC GAAACGTGGA ACGAGCCCGA | 1050 |
| TCATCACGAT TTTGACAAGC TGTCAATGAC CATGCAGGGT TTCCTTAACT | 1100 |
| ATTACGACGC CTGTTCCGAG GGATTGAGGG CAGCATCACC GGCGCTTCGG | 1150 |
| CTGGGAGGGC CTGGTGATAG CTTTCATACA CCACCTCGAT CGCCACTTTC | 1200 |
| GTGGGGCTG CTGCGCCATT GTCACGATGG TACGAACTTC TTCACCGGGG | 1250 |
| AAGCGGGGGT ACGGCTTGAT TACATCAGCC TCCACCGAAA GGGAGCGCGG | 1300 |
| TCAAGCATCT CGATTCTGGA GCAGGAGAAG GTAGTCGCTC AGCAGATCCG | 1350 |
| GCAACTCTTT CCCAAGTTCG CAGACACACC TATCTACAAT GATGAGGCAG | 1400 |
| ACCCACTTGT GGGATGGTCC CTTCCGCAGC CATGGCGCGC AGATGTGACT | 1450 |
| TATGCCGCGA TGGTAGTGAA AGTCATCGCC CAGCACCAGA ATCTGCTTCT | 1500 |
| TGCGAATACG ACCAGCGCGT TTCCTTACGC GCTTTTGTCG AACGATAATG | 1550 |
| CCTTCCTGTC ATATCACCCC CATCCGTTTG CGCAGAGGAC TCTTACGGCG | 1600 |
| CGATTCCAAG TGAATAACAC CAGACCGCCG CACGTGCAGC TGTTGCGAAA | 1650 |
| ACCCGTGTTG ACTGCGATGG GGCTTCTGGC GTTGCTTGAT GAGGAACAAC | 1700 |
| TCTGGGCTGA AGTGTCCCAG GCGGGGACAG TACTTGATAG CAATCATACA | 1750 |
| GTAGGCGTGT TGGCGTCGGC GCACCGACCG CAGGGACCCG CGGATGCTTG | 1800 |
| GAGGGCAGCG GTCCTGATCT ACGCCTCGGA CGATACTAGG GCACATCCCA | 1850 |
| ACAGATCGGT CGCTGTCACC CTTCGCCTCA GAGGGGTCCC GCCTGGTCCC | 1900 |
| GGCTTGGTAT ACGTCACTAG ATATCTCGAC AATGGACTGT GCAGCCCCGA | 1950 |

TABLE 8-continued

Elements of IDUA AAV (SEQ ID NO: 72)

| | |
|---|---|
| CGGAGAGTGG CGGAGGCTGG GACGGCCGGT GTTTCCGACA GCCGAGCAGT | 2000 |
| TTAGACGGAT GAGGGCCGCT GAGGACCCCG TGGCAGCGGC ACCGAGGCCC | 2050 |
| CTCCCGGCAG GAGGTCGCCT CACTCTTCGA CCGGCACTGC GGCTGCCGTC | 2100 |
| CCTTCTGCTC GTACACGTCT GCGCGCGACC CGAAAAGCCG CCTGGACAGG | 2150 |
| TAACCAGGCT CAGGGCGCTC CCCTTGACGC AGGGGCAGTT GGTACTTGTC | 2200 |
| TGGTCGGACG AACACGTGGG GTCCAAATGC TTGTGGACGT ATGAAATTCA | 2250 |
| GTTTTCCCAA GACGGGAAAG CGTACACTCC GGTGTCGCGC AAACCCTCCA | 2300 |
| CGTTCAACCT CTTCGTCTTT TCCCCAGACA CGGGAGCCGT ATCAGGGTCG | 2350 |
| TACCGAGTCA GAGCCCTCGA TTATTGGGCG AGGCCTGGGC CGTTCTCGGA | 2400 |
| CCCTGTACCA TACTTTGGAAG TGCCGGTGCC CAGGGACCG CCCTCGCCTG | 2450 |
| GTAATCCTTG ATAAAGATCT ctgtgccttc tagttgccag ccatctgttg | 2500 |
| tttgccccct ccccgtgcct tccttgaccc tggaaggtgc cactcccact | 2550 |
| gtcctttcct aataaaatga ggaattgca tcgcattgtc tgagtaggtg | 2600 |
| tcattctatt ctgggggtg gggtggggca ggacagcaag ggggaggatt | 2650 |
| gggaagacaa tagcaggcat gctggggatg cggtgggctc tatggACCGG | 2700 |
| TCTATCCATT GCACTATGCT TTATTTAAAA ACCACAAAAC CTGTGCTGTT | 2750 |
| GATCTCATAA ATAGAACTTG TATTTATATT TATTTTCATT TTAGTCTGTC | 2800 |
| TGGATCCACA AATTAATCGA ACCTGCAGCT GATATCGACG CTTAAGTAGG | 2850 |
| GCTTAGCAAA CGCGTCTCCA ACGTTTCGCC GTTAACACCC CACATAGTGA | 2900 |
| GTGGTCTTAG TAGTCCGGGT GTTTAAACTG AAAGATAACT CGAGCGC[AGG | 2950 |
| AACCCCTAGT GATGGAGTTG GCCACTCCCT CTCTGCGCGC TCGCTCGCTC | 3000 |
| ACTGAGGCCG CCCGGGCTTT GCCCGGGCGG CCTCAGTGAG CGAGCGAGCG | 3050 |
| CGCAG] | 3055 |

The albumin-specific 71557/71728 pair is used to cleave the albumin locus in the target human cells such that in the presence of one of the transgene donor AAVs (AAV-F.IX, AAV-IDS, AAV-IDUA), the transgene will integrate into the albumin locus through homology directed targeted integration. Upon integration, expression of the transgene is regulated by the albumin promoter.

The 71557/71728 ZFNs were compared to the 47171/47898 ZFN pair for cleaving the albumin locus in HepG2 cells and inserting the FIX transgene according to standard protocols. In brief, HepG2 cells were transduced with ZFN lots, each at an MOI of $1.25 \times 10^6$ vg/cell in a total volume of 500 μL. The cells were incubated at 37° C./5% CO2 incubator overnight (12 to 24 hours). The next day, the FIX donor was transduced with FIX Donor at an MOI of $2.5 \times 10^6$ vg/cell in a total volume of 500 μL. At day 9, the media was tested for FIX protein by ELISA using a VisuLize FIX Antigen Kit (Affinity Biologicals) according to manufacturer's instructions.

The results (see FIG. 10C) indicate that in this assay, insertion of the FIX donor using the 71557/71728 ZFNs resulted in nearly 3 times more FIX production than when the 47171/47898 pair was used.

In a similar manner, the 71557/71728 ZFNs were compared to the 47171/47898 ZFN pair for cleaving the albumin locus in HepG2 cells and inserting the IDUA transgene according to standard protocols. The results (FIG. 14) demonstrate that both pairs are able to cause ZFN-directed targeted integration of the IDUA transgene into the albumin locus, and the transgene is able to be expressed such that IDUA activity is present in the cell supernatant.

Example 7

In Vivo Cleavage and Targeted Integration

The constructs described herein were also tested in vivo.
Animal Study Design 42 male wild type C57BL/6 mice at least 6-8 weeks old were purchased from Charles River Laboratories, Inc., Wilmington, Mass. Mice handling, injection and samples collection were performed by Experimur (Chicago Ill.) according to standard protocols related to animal husbandry. Mice were held in quarantine at Experimur for at least 1 week prior to treatment initiation.

The AAV were prepared by Sangamo Therapeutics and were stored as received at −70° C. until use. Five engineered AAV2/6 vectors were used in this study; two AAV vectors encoding two ZFNs with standard architecture ("ZFN Standard"); two AAV vectors encode the two ZFNs with improved architecture ("ZFN Improved", e.g. ZFN standard+5'UTR, 3× FLAG and WPREmut6); and one AAV vector encoding the promoterless hIDS transgene DNA template (donor) flanked by mouse albumin intron 1 homology arms.

The AAV2/6 vectors were diluted into formulation buffer (PBS supplemented with 35 mM NaCl and 5% glycerol [pH 7.1]) to the doses shown in Table 1. The mice between 6 and 9 weeks of age were randomly assigned to groups 1-7. The mice in groups 1 were injected i.v. with vehicle, i.e., formulation buffer, and mice in groups 2-7 were injected i.v. with a combination of vectors at different doses as shown in Table 9 below. The total dose volume injection was 200 µL per mouse.

TABLE 9

Group designation and dose

| Group | Group Designation | No of animals | Each ZFN Dose level (vg/ mouse) | Donor Dose level (vg/ mouse) |
|---|---|---|---|---|
| 1 | Formulation buffer | 6 | 0 | 0 |
| 2 | ZFN Std Low Dose | 6 | 2.00E+10 | 1.60E+11 |
| 3 | ZFN Std Mid Dose | 6 | 6.00E+10 | 4.80E+11 |
| 4 | ZFN Std High Dose | 6 | 2.00E+11 | 1.60E+12 |
| 5 | ZFN Improved Low Dose | 6 | 2.00E+10 | 1.60E+11 |
| 6 | ZFN Improved Mid Dose | 6 | 6.00E+10 | 4.80E+11 |
| 7 | ZFN Improved High Dose | 6 | 2.00E+11 | 1.60E+12 |

AAV Vector Constructs and Packaging

The heterodimeric ZFNs targeting intron 1 of the mouse albumin locus containing the obligate heterodimer ELD/KKR mutations in the FokI domain1. For the mouse in vivo study, standard ZFNs (48641 and 31523) or improved ZFNs (48641 and 31523 with 5'UTR, N-terminal 3× FLAG and 3'WPREmut6) were used. For human in vitro study, standard ZFNs (47171 and 47898) or ZFN2.0 (71557 and 71728 with 5'UTR, N-terminal 3× FLAG and 3'WPREmut6) were used. The hIDS donor construct has been previously described (Sharma et al (2015) Blood 126, 1777-1784). The hIDS donor construct contains an hIDS cDNA lacking the endogenous IDS signal peptide, a hF9 splice acceptor sequence, and arms of homology to the mouse or human albumin target site of approximately 600 bp in length in total. Recombinant AAV2/6 vectors (comprised of AAV2 ITRs and the AAV6 capsid) were produced by triple transfection of 293 cells in 10-chamber CELLSTACK culture chambers (Corning), purified by cesium chloride density gradient centrifugation followed by dialysis, and titered as previously described (Sharma, ibid).

Tissue Collection

Mice were euthanized on day 56 in a $CO_2$ fume chamber at a flow rate of 2 L/min for 3 min. Liver samples were collected and dissected into 3 parts: one part for histopathologic analysis in 10% neutral-buffered formalin and the remaining parts were snap frozen and stored at −70° C. until processing for assessment of IDS enzymatic activity, RNA extraction, western blotting and gene modification.

Indel Detection in Liver by Next-Generation Sequencing

Genomic DNA from mouse liver samples was extracted using AllPrep DNA/RNA/Protein Mini Kit (Qiagen) following manufacture's protocol. iPS-derived hepatocytes gDNA was extracted using QIAamp DNA Micro Kit (Qiagen) following manufacture's protocol. ZFN target site was amplified by PCR using primers described in Table 10. PCR products were sequenced using MiSeq (Illumina) and analyzed as described previously (Laoharawee, K. et al. (2018) Mol. Ther. 26, 1127-1136).

TABLE 10

Primers for MiSeq analysis

| Designation | Sequence | SEQ. ID NO: |
|---|---|---|
| Mouse Alb Fw | ACACGACGCTCTTCCGATCTNN NNTTGAGTTTGAATGCACAGAT | 34 |
| Mouse Alb Rev | GACGTGTGCTCTTCCGATCTNN NNGAAACAGGGAGAGAAAAACC | 35 |
| Human Alb Fw | ACACGACGCTCTTCCGATCTNN NNGCACTAAGGAAAGTGCAAAG | 36 |
| Human Alb Rev | GACGTGTGCTCTTCCGATCTNN NNAACCAAGAAGACAGACTAAA ATG | 37 |

RT-qPCR

Total RNA from liver samples was extracted using AllPrep DNA/RNA/Protein Mini Kit (Qiagen) following manufacture's protocol. cDNA was generated using SuperScript™ III First-Strand Synthesis SuperMix (Thermo Fisher Scientific) following manufacture's protocol. qPCR was performed utilizing TaqMan Universal PCR Master Mix (Thermo Fisher Scientific). See Table 11 for primers and probes sequence. Data were normalized to the actin.

TABLE 11

RT-qPCR primers and probes

| Designation | Sequence | SEQ. ID NO: |
|---|---|---|
| Mouse ALB ex 1 Fw | CAGGGGTGTGTTTCGTCGAG | 38 |
| Human IDS Rev | ATGAGCAGGACGTTAAGCGC | 39 |
| Human IDS TaqMan | FAM-AAACCCAGGCCAACTC AACT-BHQ | 40 |

TABLE 11 -continued

RT-qPCR primers and probes

| Designation | Sequence | SEQ. ID NO: |
|---|---|---|
| Mouse Actin | NA (Thermo Fisher, Mm01205647_g1) | NA |

Western Blotting

Total protein extract was prepared from liver samples as described before3. Protein concentration was determined using the Pierce bicinchoninic acid (BCA) Protein Assay Kit (Thermo Fisher Scientific) prior to IDS detection by western blot. Antibody used were IDS (AF2449; R&D Systems) and glyceraldehyde 3-phosphate dehydrogenase (GAPDH) (A00191-40, GeneScript).

IDS Assay 1 ug of total liver protein extract or 1:3 dilution of iPS-derived hepatocytes conditional medium were used for the assay as described previously (Laoharawee, K. et al., ibid).

Liver samples were collected from the treated animals 56 days post injection and albumin cleavage activity measured as described above. In addition, transgene expression was analyzed by reverse-transcribing liver mRNA and subjecting the product to qPCR using TaqMan primer-probe pair covering junction between endogenous mouse Albumin exon 1 and transgenic human IDS. Western blot of IDS was also conducted where liver total protein extract was hybridized with human-specific IDS antibody (GAPDH served as loading control).

Figure 10A:
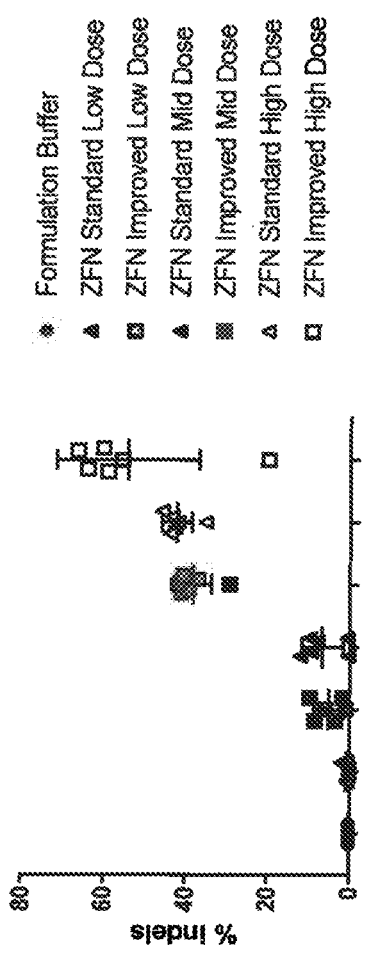
Figure 10B:
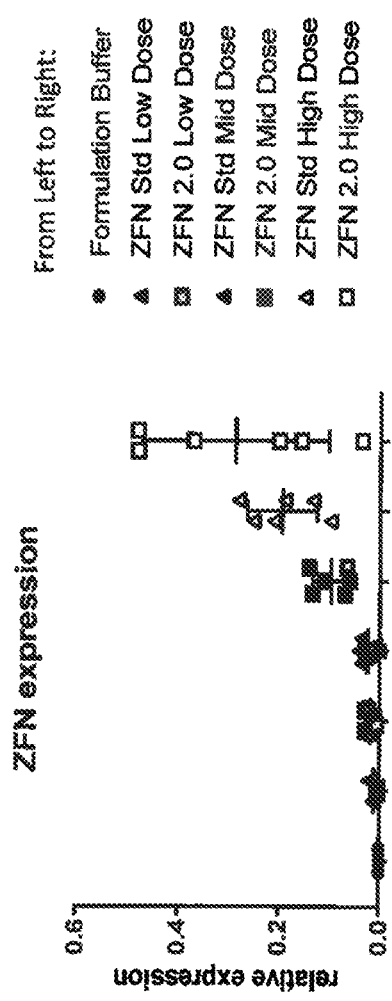

As shown in FIGS. 10A and 10B, the AAV vectors including the modifications (5'UTR, FLAG, mut6WPRE) described herein cleaved the albumin gene in vivo up to a 7-fold increase as compared to AAV vectors without the modifications. Similarly, the modified ZFNs were able to cause an increase in the integration of a F.IX donor (see FIG. 10C).

Figure 11A:
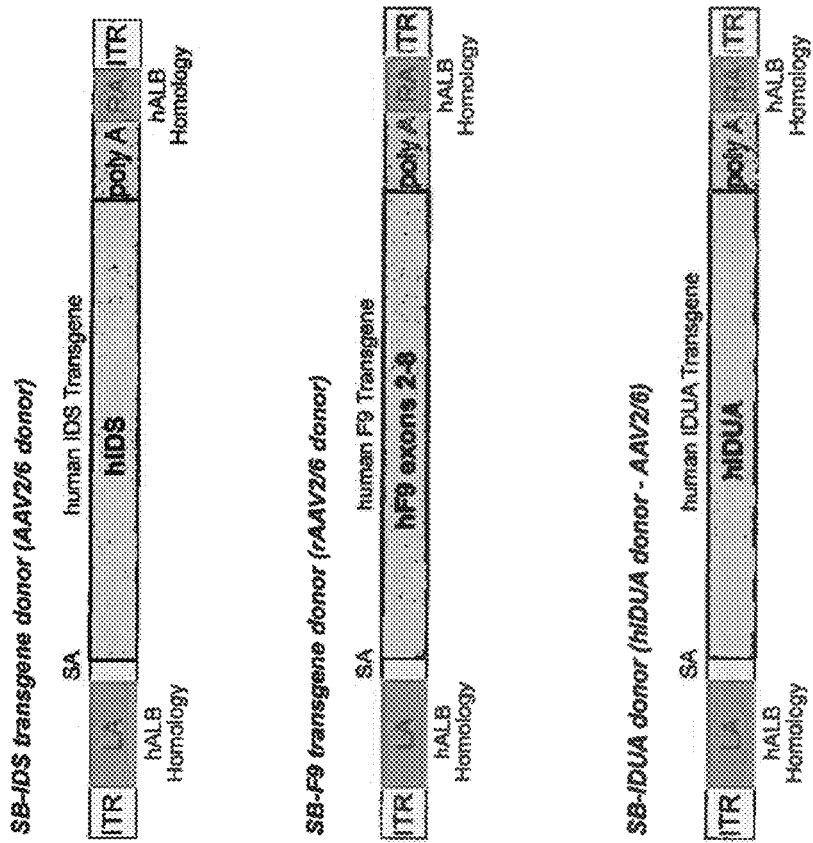
FIGS. 11A through 11C depict the donor designs used in these studies.
Figure 11B:
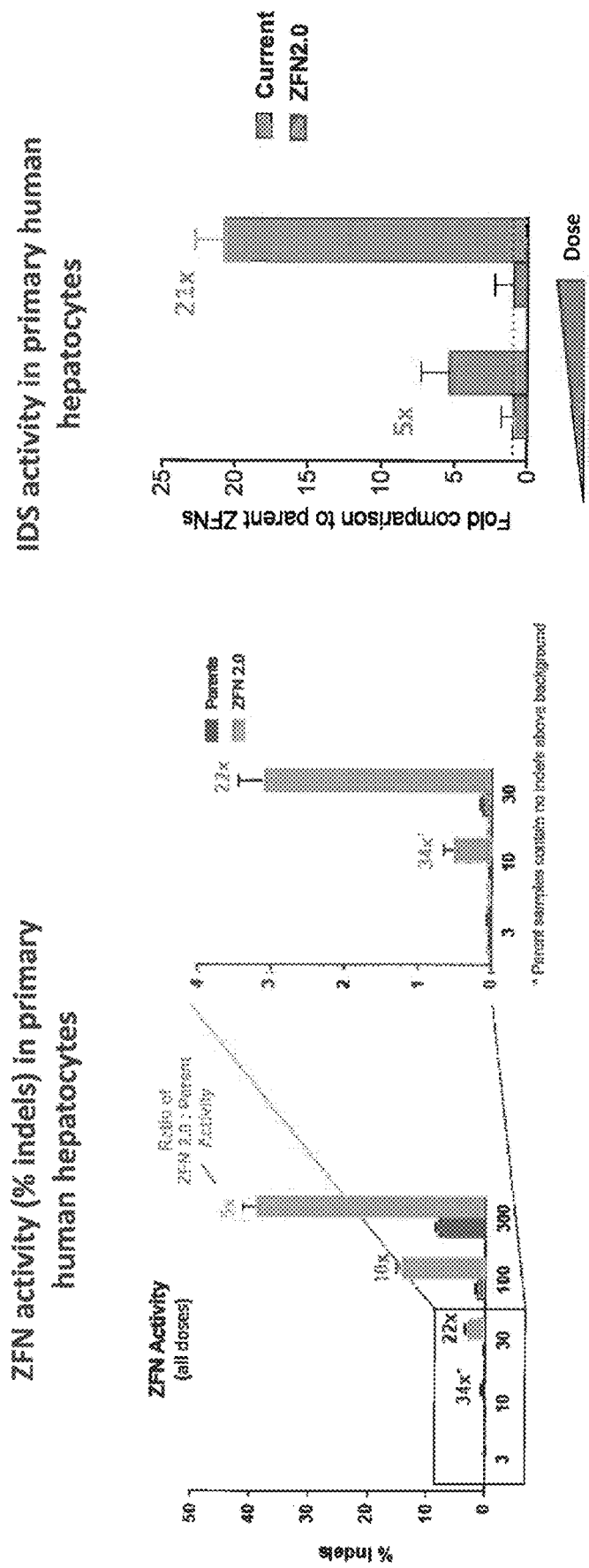
Figure 11C:
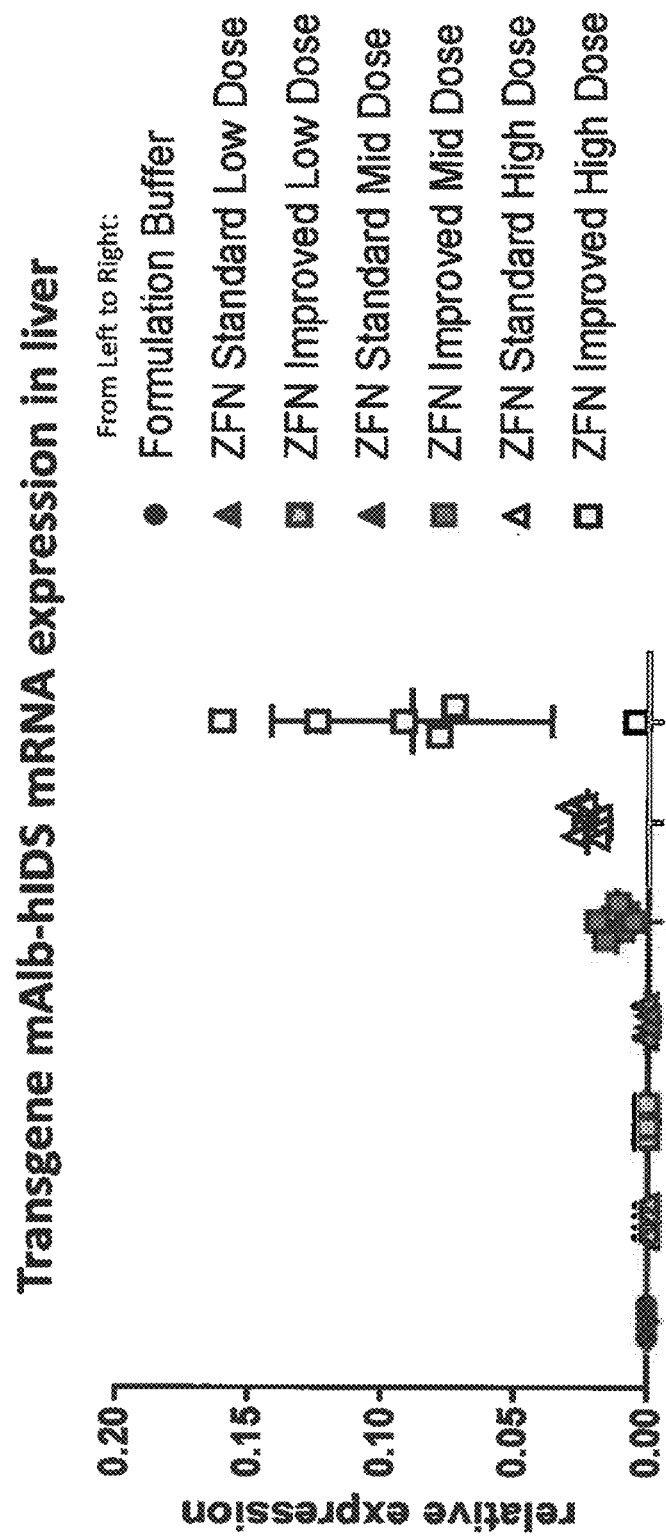
Figure 12:
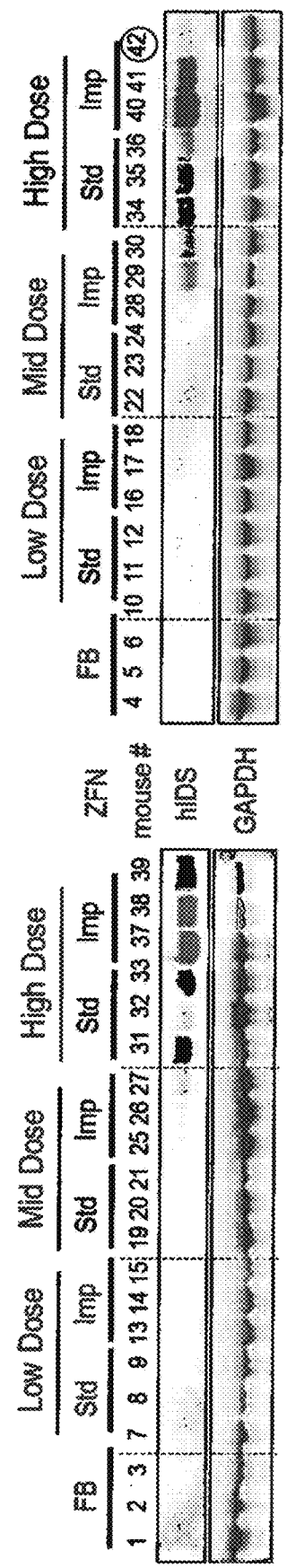
FIG. 12 shows results of Western blot analysis of IDS expression in liver samples of the subjects treated as described in Example 7 and FIGS. 10 and 11.
Figure 13:
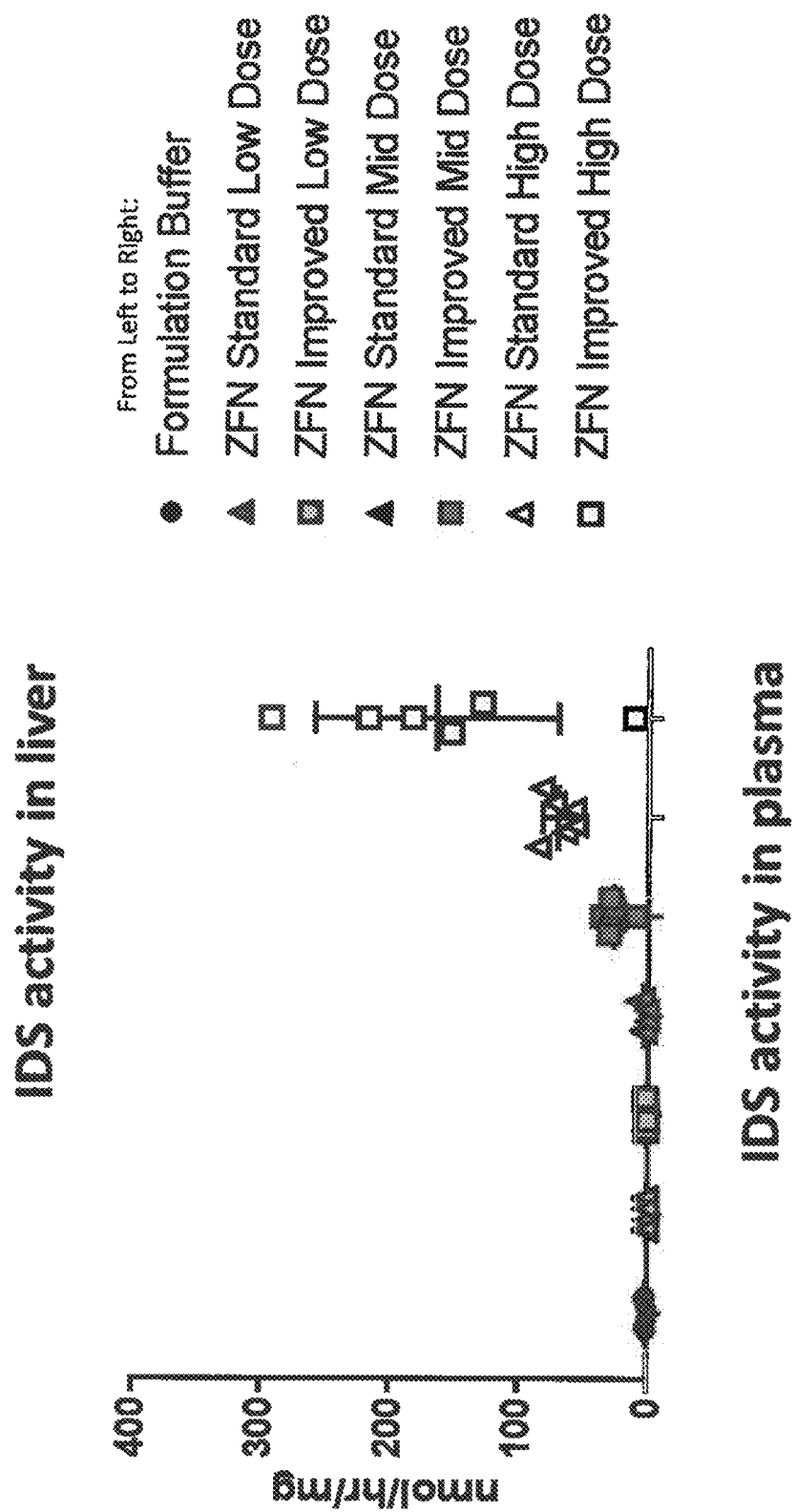
FIG. 13 is a graph showing enzymatic activity of the IDS protein encoded by the donor administered with the modified and unmodified ZFNs (at low, mid and high doses) for targeted integration (see Example 7). Enzymatic activity was measured as described in the Examples. From left to right, shown are results following administration of formulation buffer, low dose unmodified (standard) ZFN-encoding vectors, low dose AAV ZFN-encoding vectors modified as described herein, unmodified (standard) mid dose, mid dose AAV ZFN-encoding vectors ZFNs modified as described herein, unmodified (standard) high dose, and high dose AAV ZFN-encoding vectors ZFNs modified as described herein.

Furthermore, as shown in FIGS. 11 to 13, the donor IDS transgene when the modified ZFN-encoding AAV vectors were used for targeted integration, the expression of the donor transgene (IDS) was increased 18-fold in vivo as compared to integration mediated by unmodified ZFN-encoding AAV vectors (FIGS. 11 and 12) and enzymatic activity (of IDS) in plasma also increased. FIG. 11A shows a schematic of the three different donors used in this study: SB-IDS, SB-F9 and SB-IDUA. The modified ZFNs caused an increased activity against the albumin target in primary hepatocytes as shown in FIG. 11B, where the improved ZFNs ("ZFN 2.0") caused an 34 fold increase in indel percent at the mid dose and a 22 fold increase in activity at the high dose as compared to the original ZFN pair ("Current"). When these ZFNs are paired with the IDS donor, an increase in IDS activity was detected in the cell supernatant by 5 fold in a medium dose and 21 fold at a higher dose for the improved ("ZFN 2.0") ZFNs as compared to the standard ZFNs ("Current").

IDUA Activity Assay

IDUA activity is measured according to methods known in the art. For example, one exemplary assay is as follows: The activity of α-L-iduronidase was determined by a fluorometric assay using 4-methylumbelliferyl α-L-iduronide (Glycosynth) as the substrate according to the established assay condition (Whitley 1987 ibid, (Whitley 1986, ibid). The 4MU-iduronide substrate was diluted with sodium formate buffer, 0.4 M, pH 3.5 in the narrow, well-established optimal range of pH (Hopwood et al (1979), *Clin Chim Acta.* 92:257-265, Whitley 1986 ibid), and at selected substrate concentrations. Then, 25 µL aliquots of substrate were mixed with 25 µL of biological sample (e.g. plasma, leukocytes, tissue homogenates). The mixture was incubated at 37° C. for 30 min, and 200 µL glycine carbonate buffer (pH 10.4) was added to quench the reaction. α-L-iduronidase catalyzed the cleavage of the non-fluorescent substrate (4MU-iduronide) into a fluorescent product (4-MU). 4-Methylumbelliferone (4-MU, Sigma) was used to make the standard curve. The resulting fluorescence was measured using a Bio-Tek plate reader with excitation at 355 nm and emission at 460 nm. α-L-iduronidase enzyme activity was expressed in units (nmol converted to product per hour) per mg protein as determined with a Pierce protein assay kit (Fisher). All reactions were run in triplicate.

The data demonstrate that optimization of the AAV-ZFN expression constructs produces surprising and unexpected advantages in genome editing (including up to 7-fold increase in cleavage and up to an 18-fold increase in transgene expression), both in vitro and in in vivo genome editing constructs for correction of monogenic disease. Thus, by optimizing the elements that make up the ZFN expression vector, enhancements in overall ZFN activity and/or specificity are realized in vitro and in vivo. These methods can be used with any transgene donor (for example, IDS, IDUA and F.IX) for insertion into the albumin locus. Expression and secretion of the protein encoded by the transgene allows for in vivo production for a subject in need thereof.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A zinc finger nuclease (ZFN) comprising a heterodimer of a first ZFN and a second ZFN, wherein:
   (a) the first ZFN comprises:
      (i) five zinc finger domains order from F1 to F5 wherein F1 is QSGNLAR(SEQ ID NO:19), F2 is LKQNLCM (SEQ ID NO:15), F3 is WQSNLQN(SEQ ID NO:20), F4 is TSGNLTR(SEQ ID NO:17), and F5 is RRSHLTS (SEQ ID NO:21) and
      (ii) a first engineered FokI cleavage domain; and
   (b) the second ZFN comprises:
      (i) six zinc finger domains order from F1 to F6 wherein F1 is QSSDLSR(SEQ ID NO:30), F2 is LKHNLLT(SEQ ID NO:25), F3 is DQSNLRA(SEQ ID NO:31), F4 is RNFSLTM(SEQ ID NO:27), F5 is LRHDLER(SEQ ID NO:32), F6 is HRSNLNK(SEQ ID NO:29) and
      (ii) a second engineered FokI cleavage domain.

2. A polynucleotide encoding a first zing finger nuclease comprising:
   (i) five zinc finger domains order from F1 to F5 wherein F1 is QSGNLAR(SEQ ID NO:19), F2 is LKQNLCM (SEQ ID NO:15), F3 is WQSNLQN(SEQ ID NO:20), F4 is TSGNLTR(SEQ ID NO:17), and F5 is RRSHLTS (SEQ ID NO:21) and
   (ii) a first engineered FokI cleavage domain; and/or
   a second ZFN comprising:
   (i) six zinc finger domains order from F1 to F6 wherein F1 is QSSDLSR(SEQ ID NO:30), F2 is LKHNLLT(SEQ ID NO:25), F3 is DQSNLRA(SEQ ID NO:31), F4 is RNFSLTM(SEQ ID NO:27), F5 is LRHDLER(SEQ ID NO:32), F6 is HRSNLNK(SEQ ID NO:29) and
   (ii) a second engineered FokI cleavage domain.

3. An adeno associated virus (AAV) vector encoding a first zinc finger nuclease (ZFN) comprising:
   (i) five zinc finger domains order from F1 to F5 wherein F1 is QSGNLAR(SEQ ID NO:19), F2 is LKQNLCM (SEQ ID NO:15), F3 is WQSNLQN(SEQ ID NO:20), F4 is TSGNLTR(SEQ ID NO:17), and F5 is RRSHLTS (SEQ ID NO:21) and
   (ii) a first engineered FokI cleavage domain; and/or
   a second ZFN comprising:
   (i) six zinc finger domains order from F1 to F6 wherein F1 is QSSDLSR(SEQ ID NO:30), F2 is LKHNLLT(SEQ ID NO:25), F3 is DQSNLRA(SEQ ID NO:31), F4 is RNFSLTM(SEQ ID NO:27), F5 is LRHDLER(SEQ ID NO:32), F6 is HRSNLNK(SEQ ID NO:29) and
   (ii) a second engineered FokI cleavage domain.

4. The AAV vector of claim 3, wherein the AAV vector encoding the first ZFN comprises the nucleic acid sequences of SEQ ID NOs: 44 to 55 and the AAV vector encoding the second ZFN comprises nucleic acid sequences of SEQ ID NOs: 44 to 50, 57, 58, 53, 54, and 55.

5. The AAV vector of claim 4, wherein the AAV vector encoding the first ZFN comprises the sequence shown in SEQ ID NO: 43.

6. The AAV vector of claim 4, wherein the AAV vector encoding the second ZFN comprises the sequence shown in SEQ ID NO: 56.

7. A pharmaceutical composition comprising
   (a) an adeno associated virus (AAV) vector encoding a first zinc finger nuclease (ZFN) comprising:
      (i) five zinc finger domains order from F1 to F5 wherein F1 is QSGNLAR(SEQ ID NO:19), F2 is LKQNLCM (SEQ ID NO:15), F3 is WQSNLQN(SEQ ID NO:20), F4 is TSGNLTR(SEQ ID NO:17), and F5 is RRSHLTS (SEQ ID NO:21) and
      (ii) a first engineered FokI cleavage domain; and/or
   (b) an adeno associated virus (AAV) vector encoding a second ZFN comprising:
      (i) six zinc finger domains order from F1 to F6 wherein F1 is QSSDLSR(SEQ ID NO:30), F2 is LKHNLLT(SEQ ID NO:25), F3 is DQSNLRA(SEQ ID NO:31), F4 is RNFSLTM(SEQ ID NO:27), F5 is LRHDLER(SEQ ID NO:32), F6 is HRSNLNK(SEQ ID NO:29) and
      (ii) a second engineered FokI cleavage domain,
   wherein the adeno associated virus (AAV) vector encoding the first ZFN and the second ZFN can be a single vector or separate vectors.

8. The pharmaceutical composition of claim 7, further comprising a donor polynucleotide encoding a Factor IX (FIX) protein.

9. The pharmaceutical composition of claim 8, wherein
   (a) the AAV vector encoding the first ZFN comprises SEQ ID NO: 43;
   (b) the AAV vector encoding the second ZFN comprises SEQ ID NO: 56; and
   (c) the donor polynucleotide is an AAV vector comprising the sequences as shown in SEQ ID NO: 59.

10. The pharmaceutical composition of claim 9, wherein the AAV vectors encoding the first ZFN, the second ZFN, and the FIX are separate vectors.

11. The pharmaceutical composition of claim 7, further comprising a donor polynucleotide encoding an iduronate-2-sulfatase (IDS) protein.

12. The pharmaceutical composition of claim 11, wherein
(a) the AAV vector encoding the first ZFN comprises SEQ ID NO: 43;
(b) the AAV vector encoding the second ZFN comprises SEQ ID NO: 56; and
(c) the donor polynucleotide is an AAV vector comprising the sequences as shown in SEQ ID NO: 65.

13. The pharmaceutical composition of claim 12, wherein the AAV vectors encoding the first ZFN, the second ZFN, and the IDS are separate vectors.

14. The pharmaceutical composition of claim 7, further comprising a donor polynucleotide encoding an alpha-L iduronidase (IDUA) protein.

15. The pharmaceutical composition of claim 14, wherein
(a) the AAV vector encoding the first ZFN comprises SEQ ID NO: 43;
(b) the AAV vector encoding the second ZFN comprises SEQ ID NO: 56; and
(c) the donor polynucleotide is an AAV vector comprising the sequences as shown in SEQ ID NO: 72.

16. The pharmaceutical composition of claim 15, wherein the AAV vectors encoding the first ZFN, the second ZFN, and the IDUA are separate vectors.

17. A kit comprising the one or more polynucleotides of claim 2.

18. A cell comprising the one or more polynucleotides of claim 2.

19. The cell of claim 17, wherein the cell is a liver cell, a stem cell, or a precursor cell.

20. A method of cleaving an endogenous albumin gene in a cell of a subject, the method comprising administering the pharmaceutical composition of claim 7 to the subject.

21. The method of claim 20, further comprising administering a donor sequence to the subject such that the donor is integrated into the cleaved albumin gene.

22. A method of expressing a FIX protein in a subject in need thereof, the method comprising administering the pharmaceutical composition of claim 8 to the subject such that that the FIX protein is expressed in the cell.

23. A method of expressing a FIX protein in a subject in need thereof, the method comprising administering the pharmaceutical composition of claim 9 to the subject such that that the FIX protein is expressed in the cell.

24. A method of expressing a FIX protein in a subject in need thereof, the method comprising administering the pharmaceutical composition of claim 10 to the subject such that that the FIX protein is expressed in the cell.

25. The method of any one of claim 22, 23, or 24, wherein the subject has a hemophilia and expression of the FIX protein treats and/or prevents the disease.

26. A method of expressing an IDS protein in a subject in need thereof, the method comprising administering one or more pharmaceutical compositions of claim 11 to the subject such that that the IDS protein is expressed in the cell.

27. A method of expressing an IDS protein in a subject in need thereof, the method comprising administering one or more pharmaceutical compositions of claim 12 to the subject such that that the IDS protein is expressed in the cell.

28. A method of expressing an IDS protein in a subject in need thereof, the method comprising administering one or more pharmaceutical compositions of claim 13 to the subject such that that the IDS protein is expressed in the cell.

29. The method of any one of claim 26, 27, or 28, wherein the subject has MPS II disease and expression of the IDS protein treats and/or prevents the disease.

30. A method of expressing an IDUA protein in a subject in need thereof, the method comprising administering one or more pharmaceutical compositions of claim 14 to the subject such that that the IDUA protein is expressed in the cell.

31. A method of expressing an IDUA protein in a subject in need thereof, the method comprising administering one or more pharmaceutical compositions of claim 15 to the subject such that that the IDUA protein is expressed in the cell.

32. A method of expressing an IDUA protein in a subject in need thereof, the method comprising administering one or more pharmaceutical compositions of claim 16 to the subject such that that the IDUA protein is expressed in the cell.

33. The method of any one of claim 30, 31, or 32, wherein the subject has MPS I disease and expression of the IDUA protein treats and/or prevents the disease.

* * * * *

UNITED STATES PATENT AND TRADEMARK OFFICE
CERTIFICATE OF CORRECTION

PATENT NO. : 11,401,512 B2
APPLICATION NO. : 16/271250
DATED : August 2, 2022
INVENTOR(S) : Russell DeKelver et al.

It is certified that error appears in the above-identified patent and that said Letters Patent is hereby corrected as shown below:

In the Claims

Claim 2, Line 38, Column 151 should read:
2. A polynucleotide encoding a first zinc finger nuclease Claim 12, Line 4, Column 153 should read:
(b) the AAV vector encoding the second ZFN comprises Claim 25, Line 7, Column 154 should read:
The method of any one of claims 22, 23, or 24, wherein Claim 29, Line 22, Column 154 should read:
The method of any one of claims 26, 27, or 28, wherein Claim 33, Line 38, Column 154 should read:
The method of any one of claims 30, 31, or 32, wherein Signed and Sealed this
Twenty-eighth Day of February, 2023

Katherine Kelly Vidal
*Director of the United States Patent and Trademark Office*

SEQUENCE LISTING

```
<160> NUMBER OF SEQ ID NOS: 72

<210> SEQ ID NO 1
<211> LENGTH: 50
<212> TYPE: DNA
<213> ORGANISM: Xenopus sp.
<220> FEATURE:
<221> NAME/KEY: misc_feature
<222> LOCATION: (1)..(2)
<223> OTHER INFORMATION: This region may or may not be present in its
``` entirety

<400> SEQUENCE: 1
tgcttgttct ttttgcagaa gctcagaata aacgctcaac tttggcagat        50

<210> SEQ ID NO 2
<211> LENGTH: 579
<212> TYPE: PRT
<213> ORGANISM: Planomicrobium okeanokoites

<400> SEQUENCE: 2

```
Met Val Ser Lys Ile Arg Thr Phe Gly Trp Val Gln Asn Pro Gly Lys
1               5                   10                  15

Phe Glu Asn Leu Lys Arg Val Val Gln Val Phe Asp Arg Asn Ser Lys
            20                  25                  30

Val His Asn Glu Val Lys Asn Ile Lys Ile Pro Thr Leu Val Lys Glu
        35                  40                  45

Ser Lys Ile Gln Lys Glu Leu Val Ala Ile Met Asn Gln His Asp Leu
    50                  55                  60

Ile Tyr Thr Tyr Lys Glu Leu Val Gly Thr Gly Thr Ser Ile Arg Ser
65                  70                  75                  80

Glu Ala Pro Cys Asp Ala Ile Ile Gln Ala Thr Ile Ala Asp Gln Gly
                85                  90                  95

Asn Lys Lys Gly Tyr Ile Asp Asn Trp Ser Ser Asp Gly Phe Leu Arg
            100                 105                 110

Trp Ala His Ala Leu Gly Phe Ile Glu Tyr Ile Asn Lys Ser Asp Ser
        115                 120                 125

Phe Val Ile Thr Asp Val Gly Leu Ala Tyr Ser Lys Ser Ala Asp Gly
    130                 135                 140

Ser Ala Ile Glu Lys Glu Ile Leu Ile Glu Ala Ile Ser Ser Tyr Pro
145                 150                 155                 160

Pro Ala Ile Arg Ile Leu Thr Leu Leu Glu Asp Gly Gln His Leu Thr
                165                 170                 175

Lys Phe Asp Leu Gly Lys Asn Leu Gly Phe Ser Gly Glu Ser Gly Phe
            180                 185                 190

Thr Ser Leu Pro Glu Gly Ile Leu Leu Asp Thr Leu Ala Asn Ala Met
        195                 200                 205

Pro Lys Asp Lys Gly Glu Ile Arg Asn Asn Trp Glu Gly Ser Ser Asp
    210                 215                 220

Lys Tyr Ala Arg Met Ile Gly Gly Trp Leu Asp Lys Leu Gly Leu Val
225                 230                 235                 240

Lys Gln Gly Lys Lys Glu Phe Ile Ile Pro Thr Leu Gly Lys Pro Asp
                245                 250                 255

Asn Lys Glu Phe Ile Ser His Ala Phe Lys Ile Thr Gly Glu Gly Leu
            260                 265                 270

Lys Val Leu Arg Arg Ala Lys Gly Ser Thr Lys Phe Thr Arg Val Pro
        275                 280                 285

Lys Arg Val Tyr Trp Glu Met Leu Ala Thr Asn Leu Thr Asp Lys Glu
    290                 295                 300

Tyr Val Arg Thr Arg Arg Ala Leu Ile Leu Glu Ile Leu Ile Lys Ala
305                 310                 315                 320

Gly Ser Leu Lys Ile Glu Gln Ile Gln Asp Asn Leu Lys Lys Leu Gly
                325                 330                 335

Phe Asp Glu Val Ile Glu Thr Ile Glu Asn Asp Ile Lys Gly Leu Ile
            340                 345                 350
```

```
Asn Thr Gly Ile Phe Ile Glu Ile Lys Gly Arg Phe Tyr Gln Leu Lys
        355                 360                 365
Asp His Ile Leu Gln Phe Val Ile Pro Asn Arg Gly Val Thr Lys Gln
    370                 375                 380
Leu Val Lys Ser Glu Leu Glu Glu Lys Ser Glu Leu Arg His Lys
385                 390                 395                 400
Leu Lys Tyr Val Pro His Glu Tyr Ile Glu Leu Ile Glu Ile Ala Arg
                405                 410                 415
Asn Ser Thr Gln Asp Arg Ile Leu Glu Met Lys Val Met Glu Phe Phe
            420                 425                 430
Met Lys Val Tyr Gly Tyr Arg Gly Lys His Leu Gly Gly Ser Arg Lys
        435                 440                 445
Pro Asp Gly Ala Ile Tyr Thr Val Gly Ser Pro Ile Asp Tyr Gly Val
    450                 455                 460
Ile Val Asp Thr Lys Ala Tyr Ser Gly Gly Tyr Asn Leu Pro Ile Gly
465                 470                 475                 480
Gln Ala Asp Glu Met Gln Arg Tyr Val Glu Glu Asn Gln Thr Arg Asn
                485                 490                 495
Lys His Ile Asn Pro Asn Glu Trp Trp Lys Val Tyr Pro Ser Ser Val
            500                 505                 510
Thr Glu Phe Lys Phe Leu Phe Val Ser Gly His Phe Lys Gly Asn Tyr
        515                 520                 525
Lys Ala Gln Leu Thr Arg Leu Asn His Ile Thr Asn Cys Asn Gly Ala
    530                 535                 540
Val Leu Ser Val Glu Glu Leu Leu Ile Gly Gly Glu Met Ile Lys Ala
545                 550                 555                 560
Gly Thr Leu Thr Leu Glu Glu Val Arg Arg Lys Phe Asn Asn Gly Glu
                565                 570                 575
Ile Asn Phe

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Tyr Lys Asp Asp Asp Lys
1               5

<210> SEQ ID NO 4
<211> LENGTH: 23
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (1)..(1)
<223> OTHER INFORMATION: May or may not be present

<400> SEQUENCE: 4

Met Asp Tyr Lys Asp His Asp Gly Asp Tyr Lys Asp His Asp Ile Asp
1               5                   10                  15
Tyr Lys Asp Asp Asp Asp Lys
            20
```

```
<210> SEQ ID NO 5
<211> LENGTH: 7
<212> TYPE: PRT
<213> ORGANISM: Simian virus 40

<400> SEQUENCE: 5

Pro Lys Lys Lys Arg Lys Val
1               5

<210> SEQ ID NO 6
<211> LENGTH: 9
<212> TYPE: PRT
<213> ORGANISM: Unknown
<220> FEATURE:
<223> OTHER INFORMATION: Description of Unknown:
      C-myc NLS sequence

<400> SEQUENCE: 6

Pro Ala Ala Lys Arg Val Lys Leu Asp
1               5

<210> SEQ ID NO 7
<211> LENGTH: 10
<212> TYPE: PRT
<213> ORGANISM: Hepatitis delta virus

<400> SEQUENCE: 7

Glu Gly Ala Pro Pro Ala Lys Arg Ala Arg
1               5                   10

<210> SEQ ID NO 8
<211> LENGTH: 8
<212> TYPE: PRT
<213> ORGANISM: Unknown
<220> FEATURE:
<223> OTHER INFORMATION: Description of Unknown:
      polyoma T protein NLS sequence

<400> SEQUENCE: 8

Val Ser Arg Lys Arg Pro Arg Pro
1               5

<210> SEQ ID NO 9
<211> LENGTH: 18
<212> TYPE: PRT
<213> ORGANISM: Unknown
<220> FEATURE:
<223> OTHER INFORMATION: Description of Unknown:
      nucleoplasmin carboxy tail NLS sequence

<400> SEQUENCE: 9

Lys Arg Pro Ala Ala Thr Lys Lys Ala Gly Gln Ala Lys Lys Lys Lys
1               5                   10                  15

Leu Asp

<210> SEQ ID NO 10
<211> LENGTH: 38
<212> TYPE: PRT
<213> ORGANISM: Unknown
<220> FEATURE:
<223> OTHER INFORMATION: Description of Unknown:
      NLS sequence

<400> SEQUENCE: 10

Asn Gln Ser Ser Asn Phe Gly Pro Met Lys Gly Gly Asn Phe Gly Gly
```

Arg Ser Ser Gly Pro Tyr Gly Gly Gly Gln Tyr Phe Ala Lys Pro
            20                  25                  30

Arg Asn Gln Gly Gly Tyr
        35

<210> SEQ ID NO 11
<211> LENGTH: 17
<212> TYPE: PRT
<213> ORGANISM: Human T-cell leukemia virus type 1

<400> SEQUENCE: 11

Pro Lys Thr Arg Arg Pro Arg Arg Ser Gln Arg Lys Arg Pro Pro
1               5                   10                  15

Thr

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tttgggatag ttatgaattc aatcttca                                       28

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cctatccatt gcactatgct ttatttaa                                       28

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Ser Gly Asn Leu Ser Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Lys Gln Asn Leu Cys Met
1               5

<210> SEQ ID NO 16
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 16

Trp Ala Asp Asn Leu Gln Asn
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Ser Gly Asn Leu Thr Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Gln Ser His Leu Cys Leu
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ser Gly Asn Leu Ala Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Trp Gln Ser Asn Leu Gln Asn
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Arg Ser His Leu Thr Ser
1               5
```

```
<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Ile Thr Thr Leu Arg Asn
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Trp Ala Ser Asn Leu Gln Asn
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Pro Gln Leu Leu Asp Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Lys His Asn Leu Leu Thr
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Gln Ser Asn Leu Asn Ala
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 27

Arg Asn Phe Ser Leu Thr Met
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Leu Arg His Asp Leu Asp Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

His Arg Ser Asn Leu Asn Lys
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Ser Ser Asp Leu Ser Arg
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Gln Ser Asn Leu Arg Ala
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Arg His Asp Leu Glu Arg
1               5

<210> SEQ ID NO 33
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Lys Trp Asn Leu Arg Thr
1               5

<210> SEQ ID NO 34
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(24)
<223> OTHER INFORMATION: a, c, t, g, unknown or other

<400> SEQUENCE: 34
acacgacgct cttccgatct nnnnttgagt ttgaatgcac agat              44

<210> SEQ ID NO 35
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(24)
<223> OTHER INFORMATION: a, c, t, g, unknown or other

<400> SEQUENCE: 35
gacgtgtgct cttccgatct nnnngaaaca gggagagaaa aacc              44

<210> SEQ ID NO 36
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(24)
<223> OTHER INFORMATION: a, c, t, g, unknown or other

<400> SEQUENCE: 36
acacgacgct cttccgatct nnnngcacta aggaaagtgc aaag              44

<210> SEQ ID NO 37
<211> LENGTH: 47
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(24)
<223> OTHER INFORMATION: a, c, t, g, unknown or other

<400> SEQUENCE: 37
gacgtgtgct cttccgatct nnnnaaccaa gaagacagac taaaatg           47
```

```
<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cagggtgtgt tttcgtcgag                                                  20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
atgagcagga cgttaagcgc                                                  20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
aaacccaggc caactcaact                                                  20

<210> SEQ ID NO 41
<211> LENGTH: 51
<212> TYPE: DNA
<213> ORGANISM: Homo sapiens

<400> SEQUENCE: 41
attgaattca tarctatccc aaagacctat ccattgcact atgctttatt t               51

<210> SEQ ID NO 42
<211> LENGTH: 592
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
aatcaacctc tggattacaa aatttgtgaa agattgactg atattcttaa ctatgttgct      60
ccttttacgc tgtgtggata tgctgcttta atgcctctgt atcatgctat tgcttcccgt    120
acggctttcg ttttctcctc cttgtataaa tcctggttgc tgtctcttta tgaggagttg    180
tggcccgttg tccgtcaacg tggcgtggtg tgctctgtgt ttgctgacgc aaccccact    240 ggctggggca ttgccaccac ctgtcaactc ctttctggga cttttgcttt cccctcccg    300 atcgccacgg cagaactcat cgccgcctgc cttgcccgct gctggacagg ggctaggttg    360
ctgggcactg ataattccgt ggtgttgtcg gggaaatcat cgtcctttcc ttggctgctc    420
gcctgtgttg ccaactggat cctgcgcggg acgtccttct gctacgtccc ttcggctctc    480
aatccagcgg acctcccttc ccgaggcctt ctgccggttc tgcggcctct cccgcgtctt    540
cgctttcggc ctccgacgag tcggatctcc ctttgggccg cctccccgcc tg            592
```

-continued

<210> SEQ ID NO 43
<211> LENGTH: 3195
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

| | |
|---|---:|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct gcggcctaag cttgagctct tcgaaaggct cagaggcaca caggagtttc | 180 |
| tgggctcacc ctgccccctt ccaaccccte agttcccatc ctccagcagc tgtttgtgtg | 240 |
| ctgcctctga agtccacact gaacaaactt cagcctactc atgtccctaa aatgggcaaa | 300 |
| cattgcaagc agcaaacagc aaacacacag ccctccctgc ctgctgacct tggagctggg | 360 |
| gcagaggtca gagacctctc tgggcccatg ccacctccaa catccactcg acccctttgga | 420 |
| atttcggtgg agaggagcag aggttgtcct ggcgtggttt aggtagtgtg agaggggtcc | 480 |
| cggggatctt gctaccagtg aacagccac taaggattct gcagtgagag cagagggcca | 540 |
| gctaagtggt actctcccag agactgtctg actcacgcca cccctccac cttggacaca | 600 |
| ggacgctgtg gtttctgagc caggtacaat gactcctttc ggtaagtgca gtggaagctg | 660 |
| tacactgccc aggcaaagcg tccgggcagc gtaggcgggc gactcagatc ccagccagtg | 720 |
| gacttagccc ctgtttgctc ctccgataac tggggtgacc ttggttaata ttcaccagca | 780 |
| gcctcccccg ttgcccctct ggatccactg cttaaatacg gacgaggaca gggccctgtc | 840 |
| tcctcagctt caggcaccac cactgacctg ggacagtcct aggtgcttgt tctttttgca | 900 |
| gaagctcaga ataaacgctc aactttggca gatactagtc aggtaagtat caaggttaca | 960 |
| agacaggttt aaggagacca atagaaactg ggcttgtcga gacagagaag actcttgcgt | 1020 |
| ttctgatagg cacctattgg tcttactgac atccactttg cctttctctc cacaggaccg | 1080 |
| gtgccatgga ctacaaagac catgacggtg attataaaga tcatgacatc gattacaagg | 1140 |
| atgacgatga caagatggcc cccaagaaga agaggaaggt cggcattcat ggggtacccg | 1200 |
| ccgctatggc tgagaggccc ttccagtgtc gaatctgcat gcagaacttc agtcagtccg | 1260 |
| gcaacctggc ccgccacatc cgcacccaca ccggcgagaa gccttttgcc tgtgacattt | 1320 |
| gtgggaggaa atttgccctg aagcagaacc tgtgtatgca taccaagata cacacgggcg | 1380 |
| agaagccctt ccagtgtcga atctgcatgc agaagtttgc ctggcagtcc aacctgcaga | 1440 |
| accataccaa gatacacacg ggcgagaagc ccttccagtg tcgaatctgc atgcgtaact | 1500 |
| tcagtaccct cggcaacctg acccgccaca tccgcaccca caccggcgag aagccttttg | 1560 |
| cctgtgacat ttgtgggagg aaatttgccc gccgctccca cctgacctcc ataccaagga | 1620 |
| tacacctgcg gggatcccag ctggtgaaga gcgagctgga ggagaagaag tccgagctgc | 1680 |
| ggcacaagct gaagtacgtg ccccacgagt acatcgagct gatcgagatc gccaggaaca | 1740 |
| gcacccagga ccgcatcctg gagatgaagg tgatggagtt cttcatgaag gtgtacggct | 1800 |
| acagggaaa gcacctgggc ggaagcagaa agcctgacgg cgccatctat acagtgggca | 1860 |
| gccccatcga ttacggcgtg atcgtggaca caaaggccta cagcggcggc tacaatctgc | 1920 |
| ctatcggcca ggccgacgag atggagagat acgtggagga gaaccagacc cgggataagc | 1980 |
| acctcaaccc caacgagtgg tggaaggtgt accctagcag cgtgaccgag ttcaagttcc | 2040 |

```
tgttcgtgag cggccacttc aagggcaact acaaggccca gctgaccagg ctgaaccaca    2100
tcaccaactg cgacggcgcc gtgctgagcg tggaggagct gctgatcggc ggcgagatga    2160
tcaaagccgg caccctgaca ctggaggagg tgcggcgcaa gttcaacaac ggcgagatca    2220
acttcagatc ttgataactc gagtctagaa atcaacctct ggattacaaa atttgtgaaa    2280
gattgactga tattcttaac tatgttgctc cttttacgct gtgtggatat gctgctttaa    2340
tgcctctgta tcatgctatt gcttcccgta cggctttcgt tttctcctcc ttgtataaat    2400
cctggttgct gtctctttat gaggagttgt ggcccgttgt ccgtcaacgt ggcgtggtgt    2460
gctctgtgtt tgctgacgca acccccactg gctggggcat tgccaccacc tgtcaactcc    2520
tttctgggac tttcgctttc cccctcccga tcgccacggc agaactcatc gccgcctgcc    2580
ttgcccgctg ctggacaggg gctaggttgc tgggcactga taattccgtg gtgttgtcgg    2640
ggaaatcatc gtcctttcct ggctgctcg cctgtgttgc caactggatc ctgcgcggga    2700
cgtccttctg ctacgtccct tcggctctca atccagcgga cctcccttcc cgaggccttc    2760
tgccggttct gcggcctctc ccgcgtcttc gctttcggcc tccgacgagt cggatctccc    2820
tttgggccgc ctccccgcct ggctagcctg tgccttctag ttgccagcca tctgttgttt    2880
gcccctcccc cgtgccttcc ttgaccctgg aaggtgccac tcccactgtc ctttcctaat    2940
aaaatgagga aattgcatcg cattgtctga gtaggtgtca ttctattctg ggggtgggg    3000 tggggcagga cagcaagggg gaggattggg aagacaatag caggcatgct ggggatgcgg    3060
tgggctctat ggcgccgcgt cgagcgcagg aaccccctagt gatggagttg gccactccct    3120
ctctgcgcgc tcgctcgctc actgaggccg cccgggcttt gcccgggcgg cctcagtgag    3180
cgagcgagcg cgcag                                                     3195

<210> SEQ ID NO 44
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct                                                           130

<210> SEQ ID NO 45
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
aggctcagag gcacacagga gtttctgggc tcaccctgcc ccttccaac ccctcagttc      60 ccatcctcca gcagctgttt gtgtgctgcc tctgaagtcc acactgaaca aacttcagcc    120
tactcatgtc cctaaaatgg gcaaacattg caagcagcaa acagcaaaca cacagccctc    180
cctgcctgct gaccttggag ctggggcaga ggtcagagac ctctctgggc ccatgccacc    240
tccaacatcc actcgacccc ttggaatttc ggtggagagg agcagaggtt gtcctggcgt    300
```
ggtttaggta gtgtgagagg g                                          321

<210> SEQ ID NO 46
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
gatcttgcta ccagtggaac agccactaag gattctgcag tgagagcaga gggccagcta    60
agtggtactc tcccagagac tgtctgactc acgccacccc ctccaccttg gacacaggac   120
gctgtggttt ctgagccagg tacaatgact cctttcggta agtgcagtgg aagctgtaca   180
ctgcccaggc aaagcgtccg ggcagcgtag gcgggcgact cagatcccag ccagtggact   240
tagcccctgt ttgctcctcc gataactggg gtgaccttgg ttaatattca ccagcagcct   300
cccccgttgc ccctctggat ccactgctta aatacggacg aggacagggc cctgtctcct   360
cagcttcagg caccaccact gacctgggac agt                               393

<210> SEQ ID NO 47
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47 cttgttctttt ttgcagaagc tcagaataaa cgctcaactt tggcagat               48

<210> SEQ ID NO 48
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
gtaagtatca aggttacaag acaggtttaa ggagaccaat agaaactggg cttgtcgaga    60
cagagaagac tcttgcgttt ctgataggca cctattggtc ttactgacat ccactttgcc   120
tttctctcca cag                                                     133

<210> SEQ ID NO 49
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gactacaaag accatgacgg tgattataaa gatcatgaca tcgattacaa ggatgacgat    60
gacaag                                                              66

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 50
cccaagaaga agaggaaggt c                                                 21

<210> SEQ ID NO 51
<211> LENGTH: 432
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gccgctatgg ctgagaggcc cttccagtgt cgaatctgca tgcagaactt cagtcagtcc        60
ggcaacctgg cccgccacat ccgcacccac accggcgaga agccttttgc ctgtgacatt       120
tgtgggagga aatttgccct gaagcagaac ctgtgtatgc ataccaagat acacacgggc       180
gagaagccct tccagtgtcg aatctgcatg cagaagtttg cctggcagtc caacctgcag       240
aaccatacca agatacacac gggcgagaag cccttccagt gtcgaatctg catgcgtaac       300
ttcagtacct ccggcaacct gacccgccac atccgcaccc acaccggcga gaagcctttt       360
gcctgtgaca tttgtgggag gaaatttgcc cgccgctccc acctgacctc ccataccaag       420
atacacctgc gg                                                          432

<210> SEQ ID NO 52
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
cagctggtga agagcgagct ggaggagaag aagtccgagc tgcggcacaa gctgaagtac        60
gtgccccacg agtacatcga gctgatcgag atcgccagga acagcaccca ggaccgcatc       120
ctggagatga aggtgatgga gttcttcatg aaggtgtacg gctacagggg aaagcacctg       180
ggcggaagca gaaagcctga cggcgccatc tatacagtgg gcagccccat cgattacggc       240
gtgatcgtgg acacaaaggc ctacagcggc ggctacaatc tgcctatcgg ccaggccgac       300
gagatggaga gatacgtgga ggagaaccag acccgggata agcacctcaa ccccaacgag       360
tggtggaagg tgtaccctag cagcgtgacc gagttcaagt tcctgttcgt gagcggccac       420
ttcaagggca actacaaggc ccagctgacc aggctgaacc acatcaccaa ctgcgacggc       480
gccgtgctga gcgtggagga gctgctgatc ggcggcgaga tgatcaaagc cggcaccctg       540
acactggagg aggtgcggcg caagttcaac aacggcgaga tcaacttcag atcttgataa       600

<210> SEQ ID NO 53
<211> LENGTH: 592
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
aatcaacctc tggattacaa aatttgtgaa agattgactg atattcttaa ctatgttgct        60
ccttttacgc tgtgtggata tgctgcttta atgcctctgt atcatgctat tgcttcccgt       120

```
acggctttcg ttttctcctc cttgtataaa tcctggttgc tgtctcttta tgaggagttg    180
tggcccgttg tccgtcaacg tggcgtggtg tgctctgtgt ttgctgacgc aacccccact    240
ggctggggca ttgccaccac ctgtcaactc ctttctggga ctttcgcttt ccccctcccg    300
atcgccacgg cagaactcat cgccgcctgc cttgcccgct gctggacagg gctaggttg     360 ctgggcactg ataattccgt ggtgttgtcg gggaaatcat cgtcctttcc ttggctgctc    420
gcctgtgttg ccaactggat cctgcgcggg acgtccttct gctacgtccc ttcggctctc    480
aatccagcgg acctcccttc ccgaggcctt ctgccggttc tgcggcctct cccgcgtctt    540
cgctttcggc ctccgacgag tcggatctcc ctttgggccg cctccccgcc tg            592
```

<210> SEQ ID NO 54
<211> LENGTH: 223
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

```
ctgtgccttc tagttgccag ccatctgttg tttgcccctc cccgtgcct tccttgaccc    60 tggaaggtgc cactcccact gtcctttcct aataaaatga ggaaattgca tcgcattgtc    120
tgagtaggtg tcattctatt ctgggggtg gggtggggca ggacagcaag ggggaggatt    180
gggaagacaa tagcaggcat gctggggatg cggtgggctc tat                     223
```

<210> SEQ ID NO 55
<211> LENGTH: 108
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55

```
aggaacccct agtgatggag ttggccactc cctctctgcg cgctcgctcg ctcactgagg    60
ccgcccgggc tttgcccggg cggcctcagt gagcgagcga gcgcgcag                 108
```

<210> SEQ ID NO 56
<211> LENGTH: 3273
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

```
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact    120
aggggttcct gcggcctaag cttgagctct tcgaaaggct cagaggcaca caggagtttc    180
tgggctcacc ctgccccctt ccaacccctc agttcccatc ctccagcagc tgtttgtgtg    240
ctgcctctga gtccacact gaacaaactt cagcctactc atgtccctaa aatgggcaaa     300
cattgcaagc agcaaacagc aaacacacag ccctccctgc ctgctgacct tggagctggg    360
gcagaggtca gagacctctc tgggcccatg ccacctccaa catccactcg accccttgga    420
atttcggtgg agaggagcag aggttgtcct ggcgtggttt aggtagtgtg agaggggtcc    480
cggggatctt gctaccagtg gaacagccac taaggattct gcagtgagag cagagggcca    540
```

```
gctaagtggt actctcccag agactgtctg actcacgcca ccccctccac cttggacaca    600
ggacgctgtg gtttctgagc caggtacaat gactcctttc ggtaagtgca gtggaagctg    660
tacactgccc aggcaaagcg tccgggcagc gtaggcgggc gactcagatc ccagccagtg    720
gacttagccc ctgtttgctc ctccgataac tggggtgacc ttggttaata ttcaccagca    780
gcctcccccg ttgcccctct ggatccactg cttaaatacg gacgaggaca gggccctgtc    840
tcctcagctt caggcaccac cactgacctg ggacagtcct aggtgcttgt tcttttttgca   900
gaagctcaga ataaacgctc aactttggca gatactagtc aggtaagtat caaggttaca    960
agacaggttt aaggagacca atagaaactg ggcttgtcga gacagagaag actcttgcgt   1020
ttctgatagg cacctattgg tcttactgac atccactttg cctttctctc cacaggaccg   1080
gtgccatgga ctacaaagac catgacggtg attataaaga tcatgacatc gattacaagg   1140
atgacgatga caagatggcc cccaagaaga agaggaaggt cggcattcat ggggtacccg   1200
ccgctatggc tgagaggccc ttccagtgtc gaatctgcat gcgtaacttc agtcagtcct   1260
ccgacctgtc ccgccacatc cgcacccaca ccggcgagaa gccttttgcc tgtgacattt   1320
gtgggaggaa atttgccctg aagcacaacc tgctgaccca taccaagata cacacgggcg   1380
agaagccctt ccagtgtcga atctgcatgc agaacttcag tgaccagtcc aacctgcgcg   1440
cccacatccg cacccacacc ggcgagaagc cttttgcctg tgacatttgt gggaggaaat   1500
ttgcccgcaa cttctcccctg accatgcata ccaagataca caccggagag cgcggcttcc   1560
agtgtcgaat ctgcatgcgt aacttcagtc tgcgccacga cctggagcgc acatccgca   1620
cccacaccgg cgagaagcct tttgcctgtg acatttgtgg gaggaaattt gcccaccgct   1680
ccaacctgaa caagcatacc aagatacacc tgcggggatc ccagctggtg aagagcgagc   1740
tggaggagaa gaagtccgag ctgcggcaca agctgaagta cgtgccccac gagtacatcg   1800
agctgatcga gatcgccagg aacagcaccc aggaccgcat cctggagatg aaggtgatgg   1860
agttcttcat gaaggtgtac ggctacaggg aaaagcacct gggcggaagc agaaagcctg   1920
acggcgccat ctatacagtg ggcagcccca tcgattacgg cgtgatcgtg gacacaaagg   1980
cctcagcgg cggctacaat ctgagcatcg gccaggccga cgagatgcag agatacgtga   2040
aggagaacca gacccggaat aagcacatca ccccaacga gtggtggaag gtgtacccta   2100
gcagcgtgac cgagttcaag ttcctgttcg tgagcggcca cttcaagggc aactacaagg   2160
cccagctgac caggctgaac cgcaaaacca actgcaatgg cgccgtgctg agcgtggagg   2220
agctgctgat cggcggcgag atgatcaaag ccggcaccct gacactggag gaggtgcggc   2280
gcaagttcaa caacggcgag atcaacttct gataactcga gtctagaaat caacctctgg   2340
attacaaaat ttgtgaaaga ttgactgata ttcttaacta tgttgctcct tttacgctgt   2400
gtggatatgc tgctttaatg cctctgtatc atgctattgc ttcccgtacg gctttcgttt   2460
tctcctcctt gtataaatcc tggttgctgt ctctttatga ggagttgtgg cccgttgtcc   2520
gtcaacgtgg cgtggtgtgc tctgtgtttg ctgacgcaac ccccactggc tggggcattg   2580
ccaccacctg tcaactcctt tctgggactt tcgctttccc cctcccgatc gccacggcag   2640
aactcatcgc cgcctgcctt gcccgctgct ggacagggc taggttgctg ggcactgata   2700
attccgtggt gttgtcgggg aaatcatcgt cctttccttg gctgctcgcc tgtgttgcca   2760
actggatcct gcgcgggacg tccttctgct acgtcccttc ggctctcaat ccagcggacc   2820
tcccttcccg aggccttctg ccggttctgc ggcctctccc gcgtcttcgc tttcggcctc   2880
cgacgagtcg gatctcccctt tgggccgcct ccccgcctgg ctagcctgtg ccttctagtt   2940
```

```
gccagccatc tgttgtttgc ccctcccccg tgccttcctt gaccctggaa ggtgccactc    3000
ccactgtcct ttcctaataa aatgaggaaa ttgcatcgca ttgtctgagt aggtgtcatt    3060
ctattctggg gggtggggtg gggcaggaca gcaaggggga ggattgggaa gacaatagca    3120
ggcatgctgg ggatgcggtg ggctctatgc ggccgcgtcg agcgcaggaa ccctagtga    3180 tggagttggc cactccctct ctgcgcgctc gctcgctcac tgaggccgcc cgggctttgc    3240
ccgggcggcc tcagtgagcg agcgagcgcg cag                                 3273
```

<210> SEQ ID NO 57
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
gccgctatgg ctgagaggcc cttccagtgt cgaatctgca tgcgtaactt cagtcagtcc      60
tccgacctgt cccgccacat ccgcacccac accggcgaga agccttttgc ctgtgacatt     120
tgtgggagga aatttgccct gaagcacaac ctgctgaccc ataccaagat acacacgggc     180
gagaagccct tccagtgtcg aatctgcatg cagaacttca gtgaccagtc caacctgcgc     240
gcccacatcc gcacccacac cggcgagaag ccttttgcct gtgacatttg tgggaggaaa     300
tttgcccgca acttctccct gaccatgcat accaagatac accggagagc gcggcttc      360 cagtgtcgaa tctgcatgcg taacttcagt ctgcgccacg acctggagcg ccacatccgc     420
acccacaccg gcgagaagcc ttttgcctgt gacatttgtg ggaggaaatt tgcccaccgc     480
tccaacctga caagcatac caagatacac ctgcgg                                 516
```

<210> SEQ ID NO 58
<211> LENGTH: 594
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

```
cagctggtga agagcgagct ggaggagaag aagtccgagc tgcggcacaa gctgaagtac      60
gtgccccacg agtacatcga gctgatcgag atcgccagga acagcaccca ggaccgcatc     120
ctggagatga aggtgatgga gttcttcatg aaggtgtacg gctacagggg aaagcacctg     180
ggcggaagca gaaagcctga cggcgccatc tatacagtgg gcagccccat cgattacggc     240
gtgatcgtga acacaaaggc ctacagcggc ggctacaatc tgagcatcgg ccaggccgac     300
gagatgcaga gatacgtgaa ggagaaccag accggaata agcacatcaa ccccaacgag     360
tggtggaagg tgtaccctag cagcgtgacc gagttcaagt tcctgttcgt gagcggccac     420
ttcaagggca actacaaggc ccagctgacc aggctgaacc gcaaaaccaa ctgcaatggc     480
gccgtgctga gcgtggagga gctgctgatc ggcggcgaga tgatcaaagc cggcaccctg     540
acactggagg aggtgcggcg caagttcaac aacggcgaga tcaacttctg ataa            594
```

<210> SEQ ID NO 59
<211> LENGTH: 2474
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 59

```
ctgcgcgctc gctcgctcac tgaggccgcc cgggcaaagc ccgggcgtcg ggcgacctttt    60
ggtcgcccgg cctcagtgag cgagcgagcg cgcagagagg gagtggccaa ctccatcact   120
aggggttcct gcggcctaag cttgagcgga gttccaattg tactgtacag aaccatggtc   180
acatgtttaa cgctagcgtg ccgacctggt aaactgatca gtgggtgcac ttaggactgc   240
gtcttacgct aatcacatgc gtgcggccgc tttattctat tttcccagta aaataaagtt   300
ttagtaaact ctgcatcttt aaagaattat tttggcattt atttctaaaa tggcatagta   360
ttttgtattt gtgaagtctt acaaggttat cttattaata aaattcaaac atcctaggta   420
aaaaaaaaaa aaggtcagaa ttgtttagtg actgtaattt tcttttgcgc actaaggaaa   480
gtgcaaagta acttagagtg actgaaactt cacagaatag ggttgaagat tgaattcata   540
actatcccaa ggtaccacta agaattatt cttttacatt tcagttttc ttgatcatga   600
aaacgccaac aaaatcctga accggcccaa gcggtacaac tcaggcaagc tggaagagtt   660
cgtgcagggc aacctggaac gggagtgcat ggaagagaag tgcagcttcg aggaagcccg   720
ggaggtgttc gagaacaccg agcggaccac cgagttctgg aagcagtacg tggacggcga   780
ccagtgcgag tcaaacccct gcctgaacgg cggcagctgc aaggacgata tcaacagcta   840
cgagtgctgg tgcccttcg gcttcgaggg caagaactgc gagctggacg tgacctgcaa   900
catcaagaac ggccgctgcg agcagttctg caagaacagc gccgacaaca aggtggtgtg   960
ctcatgcact gagggctacc ggctggccga gaaccagaag agctgcgagc ccgccgtgcc  1020
cttcccctgc ggcagagtgt ccgtgagcca gaccagcaag ctgaccaggg ccgaggccgt  1080
gttccctgac gtggactacg tgaactcaac cgaggccgag acaatcctgg acaacatcac  1140
ccagagcacc cagtccttca cgacttcac ccgggtggtg ggcggcgagg acgccaagcc  1200
cggccagttc ccttggcagg tggtgctgaa cggcaaggtg gacgccttct cggcggctc  1260
aatcgtgaac gagaagtgga tcgtgacagc cgcccactgc gtggagacag gcgtgaagat  1320
caccgtggtg gccggcgaac acaatatcga ggaaaccgag cacaccgagc agaaacggaa  1380
cgtgatccgg attatccccc accacaacta caacgccgcc atcaacaagt acaaccacga  1440
tatcgccctg ctgaactggg acgagcctct ggtgctgaat tcatacgtga cccccatctg  1500
tatcgccgac aaagagtaca ccaacatctt tctgaagttc ggcagcggct acgtgtccgg  1560
ctggggcagg tgttccaca agggccgcag cgccctggtg ctgcagtacc tgcgggtgcc  1620
cctggtggac agagccacct gcctgcggtc aaccaagttc accatctaca acaacatgtt  1680
ctgcgccggc ttccacgagg cgggcaggga cagctgccag ggcgacagcg gcggacccca  1740
cgtgaccgag gtggagggca ccagctttct gaccggcatc atctcatggg gcgaggaatg  1800
cgccatgaag gcaagtacg gaatctacac taaggtgtca agatacgtga actggatcaa  1860
agagaaaacc aagctgacct gagtttaaac tgtgccttct agttgccagc catctgttgt  1920
ttgcccctcc cccgtgcctt ccttgaccct ggaaggtgcc actcccactg tcctttccta  1980
ataaaatgag gaaattgcat cgcattgtct gagtaggtgt cattctattc tggggggtgg  2040
ggtggggcag gacagcaagg gggaggattg ggaagacaat agcaggcatg ctggggatgc  2100
ggtgggctct atggaccggt ctatccattg cactatgctt tatttaaaaa ccacaaaacc  2160
tgtgctgttg atctcataaa tagaacttgt atttatattt attttcattt tagtctgtct  2220
```

```
ggatccacaa attaatcgaa cctgcagctg atatcgacgc ttaagtaggg cttagcaaac   2280
gcgtctccaa cgtttcgccg ttaacacccc acatagtgag tggtcttagt agtccgggtg   2340
tttaaactga agataactc gagcgcagga acccctagtg atggagttgg ccactccctc    2400
tctgcgcgct cgctcgctca ctgaggccgc ccgggctttg cccgggcggc ctcagtgagc   2460
gagcgagcgc gcag                                                    2474
```

<210> SEQ ID NO 60
<211> LENGTH: 280
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
tttattctat ttcccagta aaataaagtt ttagtaaact ctgcatcttt aaagaattat     60
tttggcattt atttctaaaa tggcatagta ttttgtattt gtgaagtctt acaaggttat   120
cttattaata aaattcaaac atcctaggta aaaaaaaaaa aaggtcagaa ttgtttagtg   180 actgtaatttt tcttttgcgc actaaggaaa gtgcaaagta acttagagtg actgaaactt   240
cacagaatag ggttgaagat tgaattcata actatcccaa                         280
```

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61

```
actaaagaat tattctttta catttcag                                      28
```

<210> SEQ ID NO 62
<211> LENGTH: 1298
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
tttttcttga tcatgaaaac gccaacaaaa tcctgaaccg gcccaagcgg tacaactcag     60
gcaagctgga agagttcgtg cagggcaacc tggaacggga gtgcatggaa gagaagtgca   120
gcttcgagga agcccgggag gtgttcgaga caccgagcg gaccaccgag ttctggaagc    180
agtacgtgga cggcgaccag tgcgagtcaa acccctgcct gaacggcggc agctgcaagg   240
acgatatcaa cagctacgag tgctggtgcc ccttcggctt cgagggcaag aactgcgagc   300
tggacgtgac ctgcaacatc aagaacggcc gctgcgagca gttctgcaag aacagcgccg   360
acaacaaggt ggtgtgctca tgcactgagg gctaccggct ggccgagaac cagaagagct   420
gcgagcccgc cgtgcccttc ccctgcggca gagtgtccgt gagccagacc agcaagctga   480
ccagggccga ggccgtgttc cctgacgtgg actacgtgaa ctcaaccgag gccgagacaa   540
tcctggacaa catcacccag agcacccagt ccttcaacga cttcacccgg gtggtgggcg   600
gcgaggacgc caagcccggc cagttcccct tggcaggtggt gctgaacggc aaggtggacg   660
ccttctgcgg cggctcaatc gtgaacgaga agtggatcgt gacagccgcc cactgcgtgg   720
```

```
agacaggcgt gaagatcacc gtggtggccg gcgaacacaa tatcgaggaa accgagcaca    780
ccgagcagaa acggaacgtg atccggatta tcccccacca caactacaac gccgccatca    840
acaagtacaa ccacgatatc gccctgctgg aactggacga gcctctggtg ctgaattcat    900
acgtgacccc catctgtatc gccgacaaag agtacaccaa catctttctg aagttcggca    960
gcggctacgt gtccggctgg ggcagggtgt tccacaaggg ccgcagcgcc ctggtgctgc   1020
agtacctgcg ggtgcccctg gtggacagag ccacctgcct gcggtcaacc aagttccacca  1080 tctacaacaa catgttctgc gccggcttcc acgagggcgg cagggacagc tgccagggcg   1140
acagcggcgg accccacgtg accgaggtgg agggcaccag ctttctgacc ggcatcatct   1200
catggggcga ggaatgcgcc atgaagggca agtacggaat ctacactaag gtgtcaagat   1260
acgtgaactg gatcaaagag aaaaccaagc tgacctga                            1298
```

<210> SEQ ID NO 63
<211> LENGTH: 225
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
ctgtgccttc tagttgccag ccatctgttg tttgcccctc ccccgtgcct tccttgaccc     60
tggaaggtgc cactcccact gtcctttcct aataaaatga ggaaattgca tcgcattgtc    120
tgagtaggtg tcattctatt ctgggggtg gggtggggca ggacagcaag ggggaggatt     180
gggaagacaa tagcaggcat gctggggatg cggtgggctc tatgg                    225
```

<210> SEQ ID NO 64
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

```
ctatccattg cactatgctt tatttaaaaa ccacaaaacc tgtgctgttg atctcataaa     60
tagaacttgt atttatattt attttcattt tagtctgtct                           100
```

<210> SEQ ID NO 65
<211> LENGTH: 2758
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120 agggggttcct gcggcctaag cttgagcgga gttccaattg tactgtacag aaccatggtc   180
acatgtttaa cgctagcgtg ccgacctggt aaactgatca gtgggtgcac ttaggactgc    240
gtcttacgct aatcacatgc gtgcggccgc tttattctat tttcccagta aaataaagtt    300
ttagtaaact ctgcatcttt aaagaattat tttggcattt atttctaaaa tggcatagta    360
ttttgtattt gtgaagtctt acaaggttat cttattaata aaattcaaac atcctaggta    420
```

-continued

| | |
|---|---|
| aaaaaaaaaa aaggtcagaa ttgtttagtg actgtaattt tcttttgcgc actaaggaaa | 480 |
| gtgcaaagta acttagagtg actgaaactt cacagaatag ggttgaagat tgaattcata | 540 |
| actatcccaa ggtaccacta aagaattatt cttttacatt tcagttagcg aaacccaggc | 600 |
| caactcaact acagatgcgc ttaacgtcct gctcatcatc gtggacgatt tgcggccgtc | 660 |
| gcttggctgc tatggagata agctcgtccg ctcgccgaac atcgatcagt tggcctcaca | 720 |
| ctcactgctt ttccaaaatg cgtttgcgca gcaggctgtc tgtgcacctt caagagtctc | 780 |
| attcttgacc gggcgacgcc ctgacacaac gcggctgtac gacttcaaca gctactggag | 840 |
| agtccacgcg ggtaactttt caactatccc acagtacttt aaagagaacg gatacgtgac | 900 |
| aatgagcgtg ggaaaggtct ttcaccccgg catctcctcg aatcacaccg acgattcgcc | 960 |
| ctactcgtgg tcgtttcctc cctaccatcc ttcgagcgag aagtatgaga acacgaaaac | 1020 |
| ttgtcgcgga cccgacggag agctgcacgc taatctgctg tgtccggtgg atgtcttgga | 1080 |
| cgtgcccgag ggaacgctcc ccgacaagca gtcaacggag caggcgattc agttgctgga | 1140 |
| gaagatgaaa acaagcgcgt cgcctttctt cctcgccgtg gggtatcaca agccccatat | 1200 |
| tcctttccgc tacccgaagg agttccagaa actttatcct ttggaaaaca tcactttggc | 1260 |
| accggacccg gaagtccccg acggtctgcc acccgtggcc tacaatccct ggatggatat | 1320 |
| caggcagagg gaagatgtgc aggcactcaa catctcagtc ccctacgggc ctattccagt | 1380 |
| cgattttcaa cgcaagattc ggcagtcgta ttttgcgtcg gtgtcctacc tcgatacgca | 1440 |
| agtaggtcga cttctgagcg cgcttgatga ccttcagctg gcaaattcca caatcatcgc | 1500 |
| ctttacgtcg gaccatgggt gggcgttggg agagcatgga gagtgggcaa gtatagcaa | 1560 |
| ttttgatgta gcaacgcacg tgcccctgat tttctacgtg ccgggtagaa cggcctcgct | 1620 |
| tcccgaggca ggcgaaaaac ttttccccta tctcgatcca ttcgactcgg cgagccagct | 1680 |
| tatggaaccg ggcagacaat ccatggactt ggtagaattg gtgtccctt ttccgaccct | 1740 |
| cgccgggttg gcgggcttgc aagtacccc tagatgccct gtaccgagct tccatgtgga | 1800 |
| actctgccgc gaagggaaaa acctcctcaa acactttcgg ttcagggacc ttgaggagga | 1860 |
| cccctatctg ccagggaatc cgcgagagtt gattgcctat tcccagtatc cgcgacccag | 1920 |
| cgatattcct caatggaact ccgataagcc ctccctcaaa gacatcaaga ttatggggta | 1980 |
| ctcgatcagg accatcgact atcgctacac agtgtgggta gggttcaatc ctgacgaatt | 2040 |
| cctcgcgaac ttttcggaca tccacgctgg tgagctgtat ttcgtagact cggacccgtt | 2100 |
| gcaagatcac aatatgtata atgattccca aggaggagat ttgttccagc tgctcatgcc | 2160 |
| gtgataaaga tctctgtgcc ttctagttgc cagccatctg ttgtttgccc ctccccgtg | 2220 |
| ccttccttga ccctggaagg tgccactccc actgtccttt cctaataaaa tgaggaaatt | 2280 |
| gcatcgcatt gtctgagtag gtgtcattct attctggggg gtggggtggg gcaggacagc | 2340 |
| aaggggagg attgggaaga caatagcagg catgctgggg atgcggtggg ctctatggac | 2400 |
| cggtctatcc attgcactat gctttatttta aaaaccacaa aacctgtgct gttgatctca | 2460 |
| taaatagaac ttgtatttat atttattttc attttagtct gtctggatcc acaaattaat | 2520 |
| cgaacctgca gctgatatcg acgcttaagt agggcttagc aaacgcgtct ccaacgtttc | 2580 |
| gccgttaaca ccccacatag tgagtggtct tagtagtccg ggtgtttaaa ctgaaagata | 2640 |
| actcgagcgc aggaacccct agtgatggag ttggccactc cctctctgcg cgctcgctcg | 2700 |
| ctcactgagg ccgcccgggc tttgcccggg cggcctcagt gagcgagcga gcgcgcag | 2758 |

<210> SEQ ID NO 66
<211> LENGTH: 1575
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66

| | | | | | |
|---|---|---|---|---|---|
| agcgaaaccc | aggccaactc | aactacagat | gcgcttaacg | tcctgctcat | catcgtggac | 60 |
| gatttgcggc | cgtcgcttgg | ctgctatgga | gataagctcg | tccgctcgcc | gaacatcgat | 120 |
| cagttggcct | cacactcact | gcttttccaa | aatgcgtttg | cgcagcaggc | tgtctgtgca | 180 |
| ccttcaagag | tctcattctt | gaccgggcga | cgccctgaca | caacgcggct | gtacgacttc | 240 |
| aacagctact | ggagagtcca | cgcgggtaac | ttttcaacta | tcccacagta | ctttaaagag | 300 |
| aacggatacg | tgacaatgag | cgtgggaaag | gtctttcacc | ccggcatctc | ctcgaatcac | 360 |
| accgacgatt | cgccctactc | gtggtcgttt | cctccctacc | atccttcgag | cgagaagtat | 420 |
| gagaacacga | aaacttgtcg | cggacccgac | ggagagctgc | acgctaatct | gctgtgtccg | 480 |
| gtggatgtct | tggacgtgcc | cgagggaacg | ctccccgaca | agcagtcaac | ggagcaggcg | 540 |
| attcagttgc | tggagaagat | gaaaacaagc | gcgtcgcctt | tcttcctcgc | cgtggggtat | 600 |
| cacaagcccc | atattccttt | ccgctacccg | aaggagttcc | agaaacttta | tcctttggaa | 660 |
| aacatcactt | tggcaccgga | cccggaagtc | cccgacggtc | tgccaccegt | ggcctacaat | 720 |
| ccctggatgg | atatcaggca | gagggaagat | gtgcaggcac | tcaacatctc | agtcccctac | 780 |
| gggcctattc | cagtcgattt | tcaacgcaag | attcggcagt | cgtattttgc | gtcggtgtcc | 840 |
| tacctcgata | cgcaagtagg | tcgacttctg | agcgcgcttg | atgaccttca | gctggcaaat | 900 |
| tccacaatca | tcgcctttac | gtcggaccat | gggtgggcgt | tgggagagca | tggagagtgg | 960 |
| gcaaagtata | gcaattttga | tgtagcaacg | cacgtgcccc | tgattttcta | cgtgccgggt | 1020 |
| agaacggcct | cgcttcccga | ggcaggcgaa | aaacttttc | cctatctcga | tccattcgac | 1080 |
| tcggcgagcc | agcttatgga | accgggcaga | caatccatgg | acttggtaga | attggtgtcc | 1140 |
| cttttttccga | ccctcgccgg | gttggcgggc | ttgcaagtac | ccctagatg | ccctgtaccg | 1200 |
| agcttccatg | tggaactctg | ccgcgaaggg | aaaaacctcc | tcaaacactt | tcggttcagg | 1260 |
| gaccttgagg | aggacccta | tctgccaggg | aatccgcgag | agttgattgc | ctattcccag | 1320 |
| tatccgcgac | ccagcgatat | tcctcaatgg | aactccgata | agccctccct | caaagacatc | 1380 |
| aagattatgg | ggtactcgat | caggaccatc | gactatcgct | acacagtgtg | ggtagggttc | 1440 |
| aatcctgacg | aattcctcgc | gaacttttcg | gacatccacg | ctggtgagct | gtatttcgta | 1500 |
| gactcggacc | cgttgcaaga | tcacaatatg | tataatgatt | cccaaggagg | agatttgttc | 1560 |
| cagctgctca | tgccg | | | | | 1575 |

<210> SEQ ID NO 67
<211> LENGTH: 1872
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

| | | | | | |
|---|---|---|---|---|---|
| cacttggtcc | acgtcgacgc | tgccagagcc | ctgtggccgc | ttcgaagatt | ttggaggtca | 60 |
| acgggtttct | gtcctcccct | tccccactcg | caagcagatc | agtatgtact | gtcatgggat | 120 |

| | |
|---|---|
| caacagctta acctcgccta tgtcggagca gtgcctcacc gcgggatcaa gcaagtaagg | 180 |
| acacattggc tccttgaact cgtcaccacg agaggatcga cgggaagggg gctttcgtac | 240 |
| aacttcactc atctcgatgg ctatttggat ctcctccgcg agaatcagtt gttgccaggc | 300 |
| ttcgaattga tgggatcggc gagcgggcac tttacagact tcgaggacaa gcagcaagtg | 360 |
| tttgagtgga aggacctcgt gtcgtcgctc gcgaggagat acattggtcg ctacggtttg | 420 |
| gcgcatgtgt caaagtggaa cttcgaaacg tggaacgagc ccgatcatca cgattttgac | 480 |
| aacgtgtcaa tgaccatgca gggtttcctt aactattacg acgcctgttc cgagggattg | 540 |
| agggcagcat caccggcgct tcggctggga gggcctggtg atagctttca tacaccacct | 600 |
| cgatcgccac tttcgtgggg gctgctgcgc cattgtcacg atggtacgaa cttcttcacc | 660 |
| ggggaagcgg gggtacggct tgattacatc agcctccacc gaaagggagc gcggtcaagc | 720 |
| atctcgattc tggagcagga gaaggtagtc gctcagcaga tccggcaact ctttcccaag | 780 |
| ttcgcagaca cacctatcta caatgatgag gcagacccac ttgtgggatg gtcccttccg | 840 |
| cagccatggc gcgcagatgt gacttatgcc gcgatggtag tgaaagtcat cgcccagcac | 900 |
| cagaatctgc ttcttgcgaa tacgaccagc gcgtttcctt acgcgctttt gtcgaacgat | 960 |
| aatgccttcc tgtcatatca cccccatccg tttgcgcaga ggactcttac ggcgcgattc | 1020 |
| caagtgaata acaccagacc gccgcacgtg cagctgttgc gaaaacccgt gttgactgcg | 1080 |
| atggggcttc tggcgttgct tgatgaggaa caactctggg ctgaagtgtc ccaggcgggg | 1140 |
| acagtacttg atagcaatca tacagtaggc gtgttggcgt cggcgcaccg accgcaggga | 1200 |
| cccgcggatg cttggagggc agcggtcctg atctacgcct cggacgatac tagggcacat | 1260 |
| cccaacagat cggtcgctgt caccctttcgc ctcagagggg tcccgcctgg tcccggcttg | 1320 |
| gtatacgtca ctagatatct cgacaatgga ctgtgcagcc ccgacggaga gtggcggagg | 1380 |
| ctgggacggc cggtgtttcc gacagccgag cagtttagac ggatgagggc cgctgaggac | 1440 |
| cccgtggcag cggcaccgag gcccctcccg gcaggaggtc gcctcactct tcgaccggca | 1500 |
| ctgcggctgc cgtcccttct gctcgtacac gtctgcgcgc gacccgaaaa gccgcctgga | 1560 |
| caggtaacca ggctcagggc gctcccccttg acgcagggcg agttggtact tgtctggtcg | 1620 |
| gacgaacacg tggggtccaa atgcttgtgg acgtatgaaa ttcagttttc ccaagacggg | 1680 |
| aaagcgtaca ctccggtgtc gcgcaaaccc tccacgttca acctcttcgt cttttcccca | 1740 |
| gacacgggag ccgtatcagg gtcgtaccga gtcagagccc tcgattattg ggcgaggcct | 1800 |
| gggccgttct cggaccctgt accatacttg gaagtgccgg tgcccagggg accgccctcg | 1860 |
| cctggtaatc ct | 1872 |

<210> SEQ ID NO 68
<211> LENGTH: 247
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

| | |
|---|---|
| gataatcaac ctctggatta caaaatttgt gaaagattga ctggtattct taactatgtt | 60 |
| gctccttta cgctatgtgg atacgctgct ttaatgcctt tgtatcatgc tattgcttcc | 120 |
| cgtatggctt tcattttctc ctccttgtat aaatcctggt tagttcttgc cacggcggaa | 180 |
| ctcatcgccg cctgccttgc ccgctgctgg acaggggctc ggctgttggg cactgacaat | 240 |

-continued

| | |
|---|---|
| tccgtgg | 247 |

<210> SEQ ID NO 69
<211> LENGTH: 592
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

| | |
|---|---|
| aatcaacctc tggattacaa aatttgtgaa agattgactg gtattcttaa ctatgttgct | 60 |
| cctttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aaccccact | 240 |
| ggttggggca ttgccaccac ctgtcagctc ctttccggga cttttcgcttt cccctccct | 300 |
| attgccacgg cggaactcat cgccgcctgc cttgcccgct gctggacagg gctcggctg | 360 |
| ttgggcactg acaattccgt ggtgttgtcg gggaaatcat cgtcctttcc ttggctgctc | 420 |
| gcctgtgttg ccacctggat tctgcgcggg acgtccttct gctacgtccc ttcggccctc | 480 |
| aatccagcgg accttccttc ccgcggcctg ctgccggctc tgcggcctct tccgcgtctt | 540 |
| cgccttcgcc ctcagacgag tcggatctcc ctttgggccg cctccccgcc tg | 592 |

<210> SEQ ID NO 70
<211> LENGTH: 9
<212> TYPE: PRT
<213> ORGANISM: Unknown
<220> FEATURE:
<223> OTHER INFORMATION: Description of Unknown:
      "LAGLIDADG" family motif peptide

<400> SEQUENCE: 70

Leu Ala Gly Leu Ile Asp Ala Asp Gly
1               5

<210> SEQ ID NO 71
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 72
<211> LENGTH: 3055
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |

```
agggggttcct gcggcctaag cttgagcgga gttccaattg tactgtacag aaccatggtc      180
acatgtttaa cgctagcgtg ccgacctggt aaactgatca gtgggtgcac ttaggactgc      240
gtcttacgct aatcacatgc gtgcggccgc tttattctat tttcccagta aaataaagtt      300
ttagtaaact ctgcatcttt aaagaattat tttggcattt atttctaaaa tggcatagta      360
ttttgtattt gtgaagtctt acaaggttat cttattaata aaattcaaac atcctaggta      420
aaaaaaaaaa aaggtcagaa ttgtttagtg actgtaattt tcttttgcgc actaaggaaa      480
gtgcaaagta acttagagtg actgaaactt cacagaatag ggttgaagat tgaattcata      540
actatcccaa ggtaccacta aagaattatt cttttacatt tcagcgcact ggtccacgt       600 cgacgctgcc agagccctgt ggccgcttcg aagattttgg aggtcaacgg gtttctgtcc      660
tccccttccc cactcgcaag cagatcagta tgtactgtca tgggatcaac agcttaacct      720
cgcctatgtc ggagcagtgc ctcaccgcgg gatcaagcaa gtaaggacac attggctcct      780
tgaactcgtc accacgagag gatcgacggg aaggggcctt tcgtacaact tcactcatct      840
cgatggctat ttggatctcc tccgcgagaa tcagttgttg ccaggcttcg aattgatggg      900
atcggcgagc gggcacttta cagacttcga ggacaagcag caagtgtttg agtggaagga      960
cctcgtgtcg tcgctcgcga ggagatacat tggtcgctac ggtttggcgc atgtgtcaaa     1020
gtggaacttc gaaacgtgga acgagcccga tcatcacgat tttgacaacg tgtcaatgac     1080
catgcagggt ttccttaact attacgacgc ctgttccgag ggattagggg cagcatcacc     1140
ggcgcttcgg ctgggagggc ctggtgatag cttttcataca ccacctcgat cgccactttc     1200
gtgggggctg ctgcgccatt gtcacgatgg tacgaacttc ttcaccgggg aagcgggggt     1260
acggcttgat tacatcagcc tccaccgaaa gggagcgcgg tcaagcatct cgattctgga     1320
gcaggagaag gtagtcgctc agcagatccg gcaactctt cccaagttcg cagacacacc      1380
tatctacaat gatgaggcag acccacttgt gggatggtcc cttccgcagc catggcgcgc     1440
agatgtgact tatgccgcga tggtagtgaa agtcatcgcc cagcaccaga atctgcttct     1500
tgcgaatacg accagcgcgt ttccttacgc gcttttgtcg aacgataatg ccttcctgtc     1560 atatcaccc catccgtttg cgcagaggac tcttacggcg cgattccaag tgaataacac      1620
cagaccgccg cacgtgcagc tgttgcgaaa acccgtgttg actgcgatgg ggcttctggc     1680
gttgcttgat gaggaacaac tctgggctga agtgtcccag gcggggacag tacttgatag     1740
caatcataca gtaggcgtgt tggcgtcggc gcaccgaccg cagggacccg cggatgcttg     1800
gagggcagcg gtcctgatct acgcctcgga cgatactagg gcacatccca acagatcggt     1860
cgctgtcacc cttcgcctca gagggtccc gcctggtccc ggcttggtat acgtcactag     1920
atatctcgac aatggactgt gcagcccga cggagagtgg cggaggctgg gacggccggt     1980
gtttccgaca gccgagcagt ttagacggat gagggccgct gaggacccccg tggcagcggc     2040 accgaggccc ctcccggcag gaggtcgcct cactcttcga ccggcactgc ggctgccgtc     2100
ccttctgctc gtacacgtct gcgcgcgacc cgaaaagccg cctggacagg taaccaggct     2160
cagggcgctc cccttgacgc aggggcagtt ggtacttgtc tggtcggacg aacacgtggg     2220
gtccaaatgc ttgtggacgt atgaaattca gttttcccaa gacgggaaag cgtacactcc     2280
ggtgtcgcgc aaaccctcca cgttcaacct cttcgtcttt tccccagaca cgggagccgt     2340
atcagggtcg taccgagtca gagccctcga ttattgggcg aggcctgggc cgttctcgga     2400
ccctgtacca tacttggaag tgccggtgcc caggggaccg ccctcgcctg gtaatccttg     2460
ataaagatct ctgtgccttc tagttgccag ccatctgttg tttgccccctc ccccgtgcct     2520
```

```
tccttgaccc tggaaggtgc cactcccact gtcctttcct aataaaatga ggaaattgca    2580
tcgcattgtc tgagtaggtg tcattctatt ctgggggggtg gggtggggca ggacagcaag    2640
ggggaggatt gggaagacaa tagcaggcat gctggggatg cggtgggctc tatggaccgg    2700
tctatccatt gcactatgct ttatttaaaa accacaaaac ctgtgctgtt gatctcataa    2760
atagaacttg tatttatatt tattttcatt ttagtctgtc tggatccaca aattaatcga    2820
acctgcagct gatatcgacg cttaagtagg gcttagcaaa cgcgtctcca acgtttcgcc    2880
gttaacaccc cacatagtga gtggtcttag tagtccgggt gtttaaactg aaagataact    2940
cgagcgcagg aaccoctagt gatggagttg gccactccct ctctgcgcgc tcgctcgctc    3000
actgaggccg cccgggcttt gcccgggcgg cctcagtgag cgagcgagcg cgcag         3055
```